US012751816B2

(12) United States Patent
Roberts et al.

(10) Patent No.: US 12,751,816 B2
(45) Date of Patent: Oct. 6, 2026

(54) HEART VALVE MANUFACTURING DEVICES AND METHODS

(71) Applicant: Edwards Lifesciences Corporation, Irvine, CA (US)

(72) Inventors: Clay Adam Roberts, Mission Viejo, CA (US); Steven E. Backer, Rancho Mission Viejo, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 978 days.

(21) Appl. No.: 17/651,736

(22) Filed: Feb. 18, 2022

(65) Prior Publication Data

US 2022/0241069 A1 Aug. 4, 2022

Related U.S. Application Data

(63) Continuation of application No. PCT/US2020/046739, filed on Aug. 18, 2020.

(Continued)

(51) Int. Cl.

*A61F 2/24* (2006.01)
*G05B 19/418* (2006.01)

(Continued)

(52) U.S. Cl.

CPC .......... *A61F 2/2415* (2013.01); *A61F 2/2427* (2013.01); *G05B 19/41875* (2013.01); *G06T 7/001* (2013.01); *A61B 34/25* (2016.02); *A61F 2/24* (2013.01); *A61F 2220/0075* (2013.01); *G05B 2219/32368* (2013.01); *G05B 2219/45172* (2013.01); *G06T 2207/20092* (2013.01); *G06T 2207/30052* (2013.01)

(58) Field of Classification Search

CPC ...................................................... A21F 2/2415
See application file for complete search history.

(56) References Cited

U.S. PATENT DOCUMENTS 3,347,190 A 10/1967 Roth
4,131,113 A * 12/1978 Fender .................. A61B 5/297 351/212

(Continued)

FOREIGN PATENT DOCUMENTS

EP 2170416 A2 4/2010
JP H1147482 A 2/1999

(Continued)

*Primary Examiner* — Erin Mcgrath
(74) *Attorney, Agent, or Firm* — Chang and Hale LLP

(57) ABSTRACT

A suturing assistance system that can be used for prosthetic heart valve manufacturing or suturing procedures. The assistance system includes an automated fixture that includes an articulating arm and a target device holder. The system also includes a vision assist system that projects a visual indicator on the surface of the target device to indicate the location of the next suture to be formed or inspected. The assistance system can include a visualization system configured to display operating procedures to an operator. The visual indicator can guide the operator in performing a sequence of steps to manufacture or inspect a target device. Properties of the visual indicator, such as color and/or shape, can be adjusted or tailored to convey information to the operator during the procedure.

19 Claims, 29 Drawing Sheets

Related U.S. Application Data

(60) Provisional application No. 62/888,986, filed on Aug. 19, 2019.

(51) Int. Cl.
*G06T 7/00* (2017.01)
*A61B 34/00* (2016.01)

(56) References Cited

U.S. PATENT DOCUMENTS

| | | | |
|---|---|---|---|
| 4,205,616 | A | 6/1980 | Sugahara |
| 4,567,882 | A | 2/1986 | Heller |
| 5,095,833 | A | 3/1992 | Darrieux |
| 6,189,747 | B1 | 2/2001 | Collingham et al. |
| 6,295,940 | B1 | 10/2001 | Shonteff |
| 6,453,062 | B1 | 9/2002 | MacNutt et al. |
| 7,739,971 | B2 | 6/2010 | Chambers et al. |
| 8,276,533 | B2 | 10/2012 | Chambers et al. |
| 9,301,835 | B2 | 4/2016 | Campbell et al. |
| 9,339,378 | B2 | 5/2016 | Quadri et al. |
| 10,119,882 | B2 | 11/2018 | Van Nest et al. |
| 2005/0013841 | A1 | 1/2005 | Phillips et al. |
| 2006/0106483 | A1 | 5/2006 | Behan et al. |
| 2006/0276889 | A1 | 12/2006 | Chambers et al. |
| 2008/0035038 | A1 | 2/2008 | Ekholm et al. |
| 2008/0121168 | A1* | 5/2008 | Ryznar ............. G05B 19/41805 116/202 |
| 2008/0223272 | A1 | 9/2008 | Hattori |
| 2010/0257735 | A1 | 10/2010 | Chambers et al. |
| 2014/0033959 | A1 | 2/2014 | Evans et al. |
| 2017/0325976 | A1 | 11/2017 | Nguyen et al. |
| 2018/0185025 | A1* | 7/2018 | Gorek .............. A61B 17/06061 |
| 2018/0250129 | A1 | 9/2018 | Koral et al. |
| 2018/0355530 | A1* | 12/2018 | Blenis, Jr. .............. D05B 19/12 |

FOREIGN PATENT DOCUMENTS

| | | | |
|---|---|---|---|
| WO | 1995030387 | A1 | 11/1995 |
| WO | 2001082781 | A2 | 11/2001 |
| WO | 2008016760 | A2 | 2/2008 |
| WO | WO-2015039246 | A1 | 3/2015 |
| WO | 2015070249 | A1 | 5/2015 |
| WO | 2018156767 | A1 | 8/2018 |
| WO | 2019140293 | A1 | 7/2019 |

* cited by examiner

FIG. 19
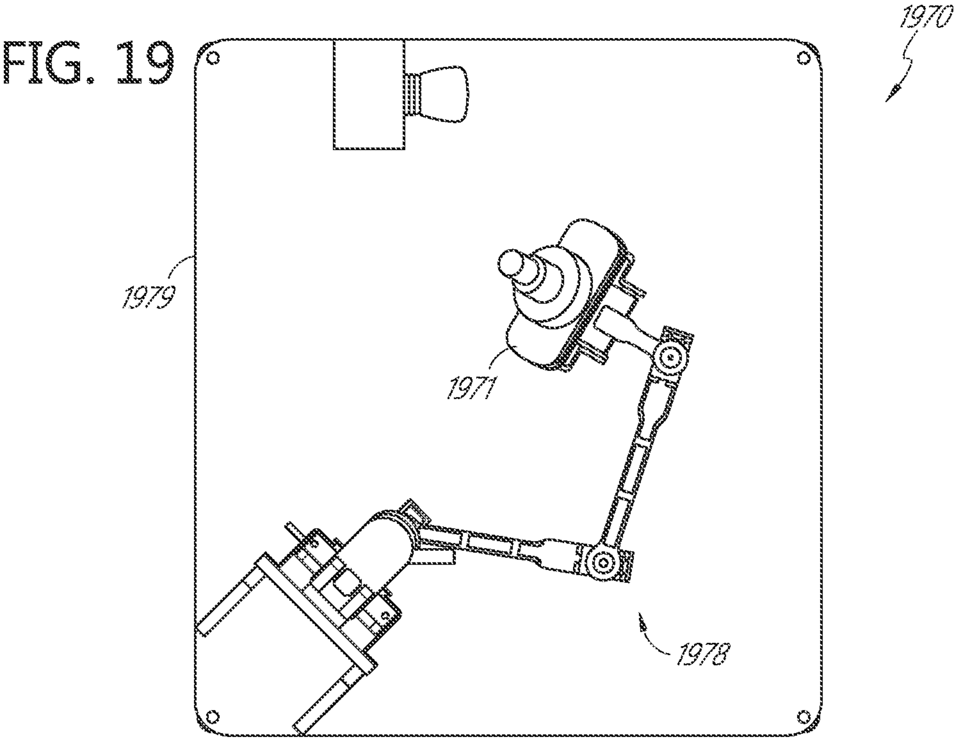
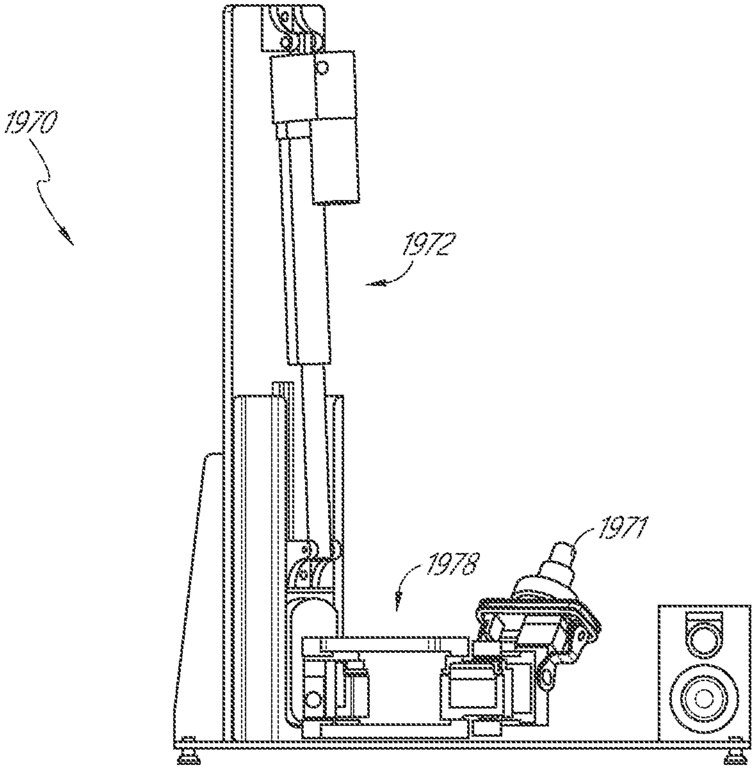
FIG. 20

FIG. 21
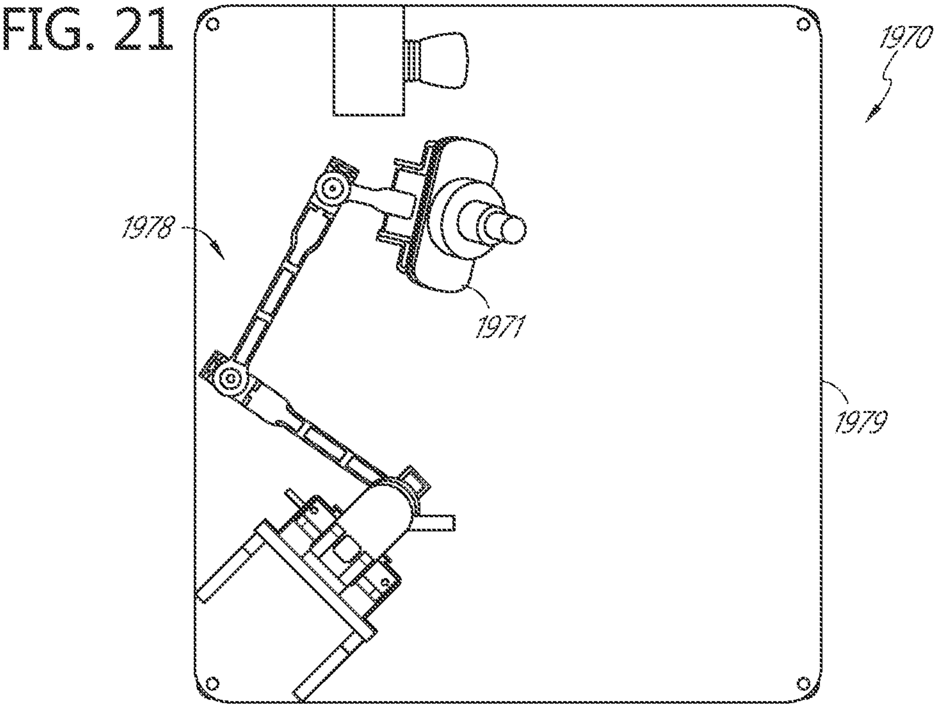
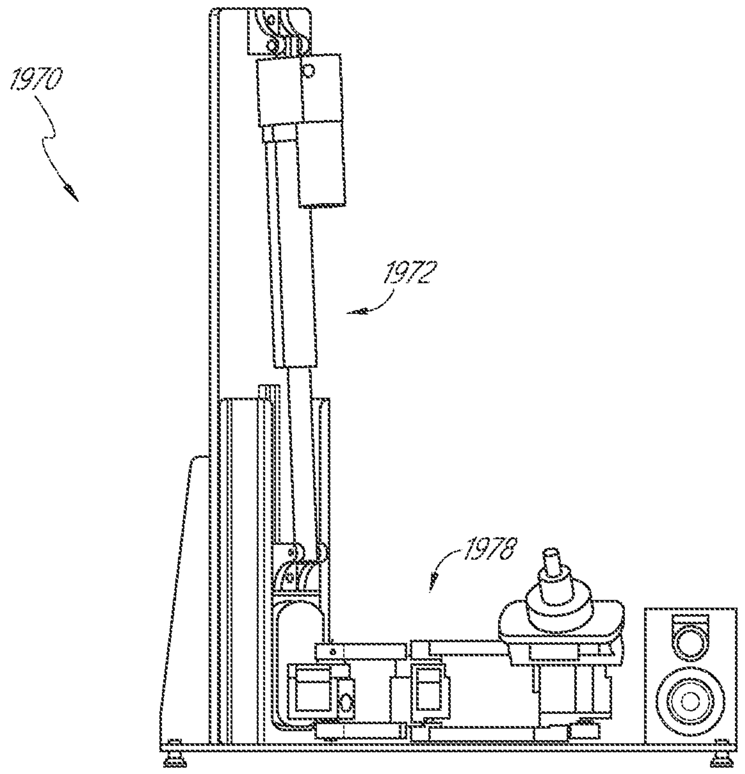
FIG. 22

FIG. 23
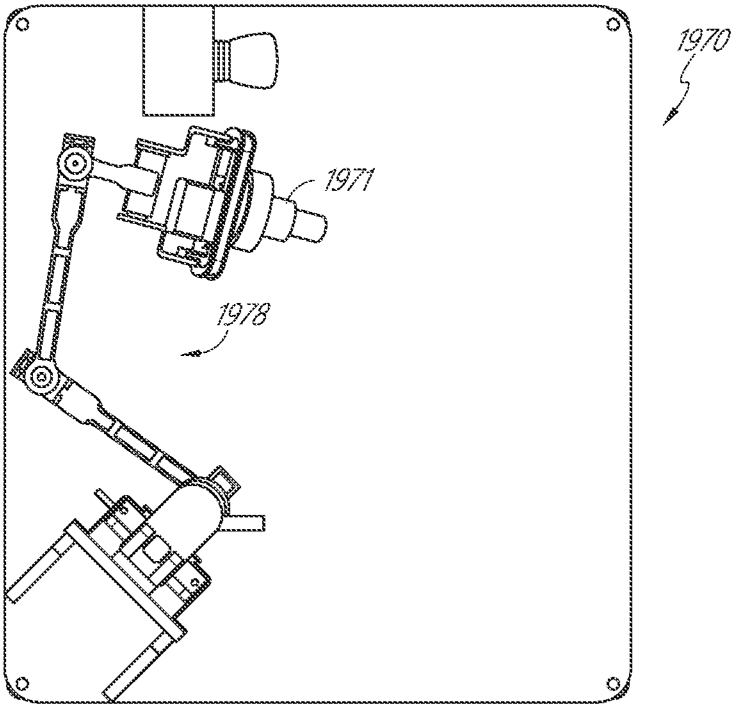
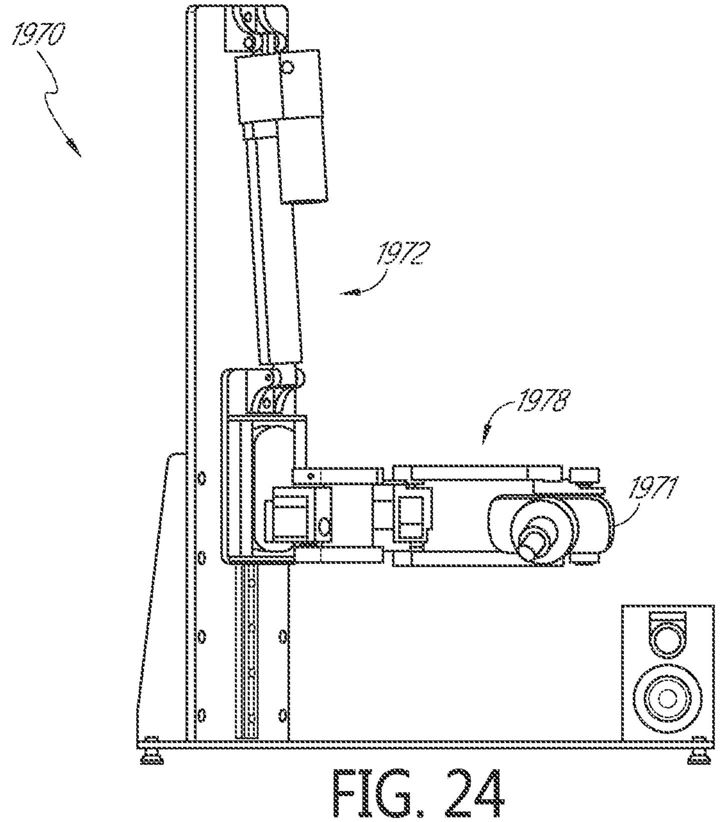
FIG. 24

HEART VALVE MANUFACTURING DEVICES AND METHODS

CROSS-REFERENCE TO RELATED APPLICATION

This application is a continuation of International Application No. PCT/US2020/046739 filed Aug. 18, 2020, and entitled "HEART VALVE MANUFACTURING DEVICES AND METHODS," which claims the benefit of priority to U.S. Prov. App. No. 62/888,986 filed Aug. 19, 2019, and entitled "HEART VALVE MANUFACTURING DEVICES AND METHODS," the entirety of which is incorporated by reference herein for all purposes.

FIELD

The present disclosure generally relates to the field of heart valve manufacturing and associated systems, devices, and methods, including heart valve suturing systems, devices, and methods.

BACKGROUND

Manufacturing prosthetic heart valves and other human prosthetic implant devices may require suturing, treatment, inspection, etc. of certain portions and/or components thereof. Accuracy and/or efficiency in execution of suturing operations or other operations for such devices can be important. Furthermore, it would be beneficial to reduce the possibility of operator strain that might arise under certain heart valve suturing operations or other operations.

SUMMARY

This summary is meant to provide some examples and is not intended to be limiting of the scope of the invention in any way. For example, any feature included in an example of this summary is not required by the claims, unless the claims explicitly recite the features. Also, the features, steps, concepts, etc. described in examples in this summary and elsewhere in this disclosure can be combined in a variety of ways. The description herein relates to devices, apparatuses, systems, assemblies, methods, combinations, etc. that can be utilized for manufacturing and processing heart valves and/or associated or related components, devices, apparatuses, etc.

In some implementations, the present disclosure relates to a method of manufacturing a target device or component (e.g., to a method of manufacturing, or suturing, a prosthetic implant device, prosthetic human implant device, prosthetic heart valve, prosthetic human heart valve, etc.). The method can comprise disposing the target device (e.g., prosthetic human implant device, etc.) on a holder component of an automated fixture (e.g., an automated suture fixture). The method can also comprise directing or providing input to cause the automated fixture (e.g., automated suture fixture) to position the target device (e.g., prosthetic human implant device, etc.) in a first position; providing a visual indicator on a surface of the target device to indicate a first target location; executing a first operation or procedure (e.g., a stitch, inspection, other operation or procedure) on the target device (e.g., prosthetic human implant device, etc.) at the first target location or receiving an indication (e.g., through user input) that the first operation has been executed; directing or providing input to cause the automated fixture (e.g., automated suture fixture) to position the target device (e.g., prosthetic human implant device, etc.) in a second position; providing the visual indicator on the surface of the target device to indicate a second target location; and executing a second operation or procedure (e.g., stitch, inspection, etc.) on the target device (e.g., prosthetic human implant device, etc.) at the second target location or receiving an indication that the second operation has been executed. This process may be repeated for any suitable number of steps in a process. In such a process, an individual step can include positioning the target device in a targeted position and providing a visual indicator on a surface of the target device at a corresponding target location. Once a corresponding operation has been executed for the current position, the method can include moving to the next position in the procedure. In some embodiments, the individual step in the process can include executing (e.g., by an automated component) a corresponding operation on the target device or receiving an indication (e.g., through user input) that the corresponding operation has been executed (e.g., by an operator) prior to moving the target device to the next position in the sequence. The target device can be a prosthetic human implant device. The prosthetic human implant device can be a heart valve or other type of implant device.

The step of directing or providing input to cause the automated fixture (e.g., automated suture fixture) to position the target device (e.g., prosthetic human implant device, etc.) in the first or second position can involve directing or providing input to cause the automated fixture to move the target device to a desired position relative to a machine vision system (e.g., a camera or other imaging system). In response, a vision assist system can adjust a location of the visual indicator to identify a location for the next step (e.g., stitch, inspection, etc.) in the manufacturing or inspection procedure. The method can also include providing user input that causes the automated fixture to move or to rotate (e.g., rotate; circumferentially rotate; flip; rotate with respect to an axis, such as an axis that passes through a center point of the device; etc.) the target device in place so that the vision assist system does not move to cause the visual indicator to be positioned at the target location on the surface of the target device. This can be done with or without moving the visualization system (e.g., without moving a camera). Operation of the automated fixture can provide for reduced physical strain on the operator, e.g., it can replicate and/or remove the need for the operator to bend, twist, turn, etc. one hand to move the target device into place for an operation (e.g., for suturing, for inspection, etc.).

The method can further include loading a procedure script (e.g., a pre-programmed suturing script, inspection script, other procedure script, etc.) using one or more processors configured to at least partially control the automated fixture. The procedure script can be used to control a vision assist system that provides the visual indicator. The procedure script can provide the targeted locations throughout the procedure for the visual indicator and the vision assist system can determine how to position components of the vision assist system to achieve projecting the visual indicator at the targeted locations. The procedure script advantageously ensures the correct sequence of operations is performed for the corresponding procedure (e.g., suturing, inspection, etc.).

The target device can comprise an outside surface and an inside surface defining an at least partially open inside cylinder cavity. The first operation can be a first stitch, and the first stitch can be an outside-to-inside stitch executed by puncturing a needle through the outside surface to the inside cylinder cavity. For the first operation, the vision assist system can provide the visual indicator on the outside surface of the target device where the needle is to puncture the target device. However, in some embodiments, the vision assist system can provide the visual indicator on the inside surface of the target device such that the visual indicator can be seen through the material of the target device. The second operation can be a second stitch, and the second stitch can be an inside-to-outside stitch executed by puncturing the inside surface. For the second operation, the vision assist system can provide the visual indicator on the inside surface of the target device where the needle is to puncture the target device. However, in some embodiments, the vision assist system can provide the visual indicator on the outside surface of the target device such that the visual indicator can be seen through the material of the target device. In some embodiments, the first position can present the outside surface (e.g., a portion of the outside surface) to the operator and the second position can present the inside surface (e.g., a portion of the inside surface) to the operator.

In some embodiments, the target device may not include an inside and outside surface. In such embodiments, the vision assist system may provide the visual indicator in the same side of the surface to be punctured by the needle. In such embodiments, the vision assist system may provide the visual indicator on the opposite side of the surface to be punctured such that the visual indicator can be seen through the material of the target device.

In certain implementations, the vision assist system includes a display whereupon the vision assist system displays a live image of the target device. The vision assist system can also be configured to superimpose a visual indicator on the live image of the target device indicating the target location. The visual indicator can be configured to provide information to the operator to facilitate performance of the step in the procedure being performed (e.g., suturing, inspecting, etc.). The vision assist system is also configured to determine a position and orientation of the target device based on the live image of the target device to determine the corrected location to superimpose the visual indicator on the live image. To determine the position and orientation, in some embodiments, the vision assist system is configured to access a computer model of the target device to analyze and compare the live image of the target device to the computer model. In some embodiments, the target device may include visual markers to more easily identify a position and orientation of the target device for the vision assist system (and/or an operator). In some embodiments, the vision assist system is also configured to provide additional information on the display such as instructions to an operator for performing the next step(s) in the procedure. In some embodiments, the visual indicator also provides information to the operator, wherein the information is correlated with the step(s) to be performed. By way of example only, the information can include instructions such as “complete sewing step 4.1.7 by completing a zig-zag stitch from the starting to the finishing point indicated on the screen.”

The methods can utilize receiving input from a user input device(s). For example, user input device(s) that can be used include a joystick device, pedal(s), button(s), electronic input(s), touchscreen control, other input device or mechanisms, or a combination of input devices and/or mechanisms. For example, the user input can involve pressing a foot pedal, button, electronic input, touchscreen control, etc.

The method can further comprise adjusting a light source (e.g., a laser, a projector, etc.) of a vision assist system on a target device held by the automated fixture to generate the visual indicator. Data from a procedural script can be used to indicate a target location on the target device for the visual indicator. In some embodiments, the vision assist system can be configured to not move the visual indicator when the automated fixture adjusts the position of the target device resulting in the visual indicator being projected on a different target location on a surface of the target device. In certain embodiments, the vision assist system adjusts the light source to be in a first orientation to project the visual indicator on the first target location when the automated fixture is in the first position, and adjusts the light source to a second orientation to project the visual indicator on the second target location when the automated fixture is in the second position. In such embodiments, the automated fixture may or may not adjust a position of the target device.

The method(s) can include using an assistance system (e.g., a manufacturing assistance system, an attachment assistance system, a suturing assistance system, an inspection assistance system, etc.). An assistance system can comprise an automated fixture (e.g., automated suture fixture) comprising a plurality of motorized actuator devices and a holder (e.g., a target holder, suture target holder, holder assembly, holder device, holder component, etc.). The automated fixture can be configured to rotate a target device (e.g., a target suture device, implant, heart valve, prosthetic human implant, etc.) connected to, mounted to, or otherwise supported by the holder. The assistance system can include a machine vision, visualization, or imaging system (e.g., a camera system, etc.) configured to generate an image of the target device and a display, monitor, or screen (e.g., a suture target display) configured to display or show the image. The display (e.g., suture target display, monitor, screen, etc.) can indicate a target position (e.g., a target suture position, target inspection position, target operation position, etc.) associated with the target device. In addition, the assistance system can include a vision assist system configured to project a visual indicator on the target device to indicate the target position on the target device. In some embodiments, the vision assist system is configured to provide the visual indicator on the display of the assistance system in addition to or in place of the visual indicator projected on the target device. The target device can be a heart valve, implant, prosthetic human implant, etc., and/or a component thereof. The assistance system can further include a controller configured to direct the automated fixture, the visualization system, and the vision assist system. The assistance system can provide for reduced physical strain on an operator thereof compared to dual-hand or two-handed procedures (e.g., dual-hand or two-handed suturing procedures, etc.).

The visual indicator can include light from a light source directed and/or focused onto the surface of the target device. For example, the visual indicator can include light from a laser directed onto the surface of the target device. As another example, the visual indicator can include an image from a projector focused or directed onto the surface of the target device. As another example, the visual indicator can include light from a fiber optic cable directed onto a surface of the target device. The visual indicator can be an image or sequence of images projected onto a surface of the target device. The visual indicator can be a single spot of light or multiple spots of light on different surfaces of the target device. For example, the visual indicator can simultaneously include light directed to an outside surface of the target device and light directed to an inside surface of the target device. The visual indicator can have a color and/or can change color to provide information to an operator. The visual indicator can be made to be solid and/or to flash to provide information to the operator. Information that can be provided to the operator through the visual indicator can include, for example and without limitation, a location of a stitch, a type of stitch, correct performance of a stitch, incorrect performance of a stitch, entrance and/or exit location of a stitch, and the like.

The display (e.g., suture target display, monitor, screen, etc.) can comprise a reticle. For example, the reticle can comprise a circular reticle, which can include notches for stitch counting, and/or a ruler. The display can be configured to display instructions (e.g., suturing instructions, step instruction, procedure instructions, etc.) in connection with a procedure (e.g., suturing procedure, inspection procedure, other procedure, etc.).

The holder (e.g., target suture device holder, etc.) can be a gimbal holder assembly. For example, the gimbal holder assembly can comprise a three-axis gimbal.

The automated fixture can be configured to move the target device in at least four directions. The automated fixture can comprise a plurality of servo motor devices daisy-chained together. The plurality of servo motor devices can be configured to be mounted horizontally, vertically, or at another angle relative to the ground and/or other servo motor devices. The automated fixture can comprise an encoder associated with an articulation arm wherein the encoder is configured to provide position information for the articulation arm. The automated fixture can comprise a plurality of actuator devices (e.g., motorized actuator devices). Each of the actuator devices can comprise a motor and a rotating support member coupled to a rotor component of the motor. A holder assembly or holder (e.g., a suture target holder assembly, etc.) can be attached to the rotating support member of a distal actuator device of the plurality of actuator devices and can be configured to hold the target device. Each of the plurality of actuator devices can be fixed to one or more other actuator devices of the plurality of actuator devices. Furthermore, the automated fixture can be configured to receive control signals and to rotate the rotating support members of one or more of the plurality of actuator devices based on the control signals. Each of the plurality of actuator devices can further comprise a servo feedback component configured to generate a signal indicating a position of a respective rotor component.

The assistance system (e.g., suturing assistance system, manufacturing assistance system, inspection assistance system, other procedure assistance system, etc.) can comprise an automated fixture and a holder. The automated fixture can be configured to position a target device mounted to the holder. The assistance system can include a vision assist system that includes one or more articulating components to provide and to adjust a visual indicator projected onto the target device. The assistance system can include a data store (e.g., memory, database, etc.) storing procedure script data (e.g., suturing procedure script data, inspection script data, manufacturing script data, other procedure script data, etc.). The procedure script data can include a data set representing a three-dimensional model of the target device and locations for stitches on the target device. The procedure script data can also include a plurality of positions of the automated fixture for a procedure (e.g., for a suturing procedure, inspection procedure, manufacturing procedure, other procedure, etc.). The assistance system can include a controller configured to access the procedure script data to determine a position and orientation of the vision assist system so that the visual indicator is projected onto a target location on the target device. The position and orientation of the vision assist system (or components thereof) is based at least in part on the three-dimensional model of the target device in combination with the position and orientation of the automated fixture.

The controller can be further configured to select the data set from among a plurality of data sets of the procedure script data (e.g., suturing procedure script data). For example, the selecting can be based at least in part on operator profile information and/or user input received by the controller. Optionally, an operator profile can be applied to or combined with procedure script data to generate individualized procedure script data particular to the preference and/or characteristics of the operator. The plurality of data sets can include a first data set corresponding to a right-handed execution of the suturing procedure and a second data set corresponding to a left-handed execution of the suturing procedure.

Other steps, features, components, etc. not specifically mentioned in these examples, but described elsewhere herein or otherwise known can also be included and/or used with the examples described herein.

BRIEF DESCRIPTION OF THE DRAWINGS

Various embodiments are depicted in the accompanying drawings for illustrative purposes and should in no way be interpreted as limiting the scope of the claimed embodiments. In addition, various features of different disclosed embodiments can be combined to form additional embodiments, which are part of this disclosure. Throughout the drawings, reference numbers may be reused to indicate correspondence between reference elements.

FIGS. 18, 19, 20, 21, 22, 23, 24, and 25 illustrate views of a snake-like configuration of an automated fixture in accordance with one or more embodiments.

DETAILED DESCRIPTION

Figure 1:
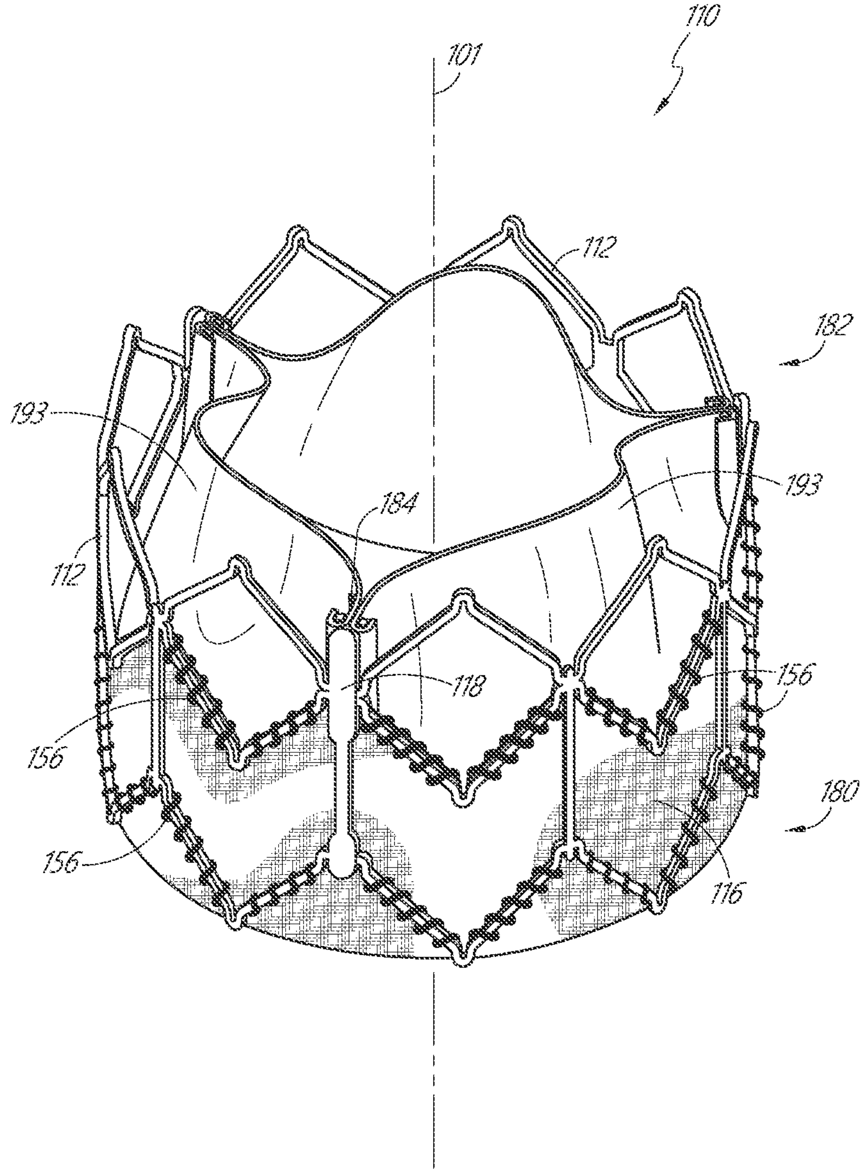
FIG. 1 illustrates an implantable prosthetic valve device according to one or more embodiments.

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Further, one or more steps disclosed with respect to one method may be incorporated into other methods disclosed herein. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Features described with respect to one exemplary embodiment may be incorporated into other embodiments disclosed herein even if not specifically described with respect to the embodiment.

Overview

Prosthetic heart valve implants, as well as many other types of prosthetic implant devices and other types of devices, can include various sutured components and/or portions. For example, a sealing portion, skirt, etc. can be sutured to a frame of a prosthetic heart valve to help prevent blood from leaking around the outer edges or circumference of the prosthetic heart valve. Execution of sutures by a human operator may be relatively difficult and/or cumbersome in certain conditions. For example, where small stitches are to be made with high precision, the complexity and/or associated operator burden may result in injury and/or undesirably low quality of products. Furthermore, certain heart valve implant devices may require upward of a thousand sutures, which can involve substantially labor-intensive and error-susceptible suturing procedures. Therefore, collaborative suturing aids can be desirable to improve quality and/or to reduce the possibility of operator strain.

Certain embodiments disclosed herein provide collaborative heart valve suturing systems, devices, and/or methods for providing suturing assistance for point-by-point suturing procedures based on the physical manipulation and/or positioning of one or more automated mechanical articulating fixtures, components, and/or subassemblies. Such articulating fixture(s) or component(s) may be configured to hold or secure a prosthetic human heart valve implant device or other suturing subject or implant device having one or more components or portions that may advantageously be sutured together. Suture assistance systems, devices, and/or processes in accordance with the present disclosure may implement a vision assist system configured to provide visual indicators for stitch targeting, inspection, or the like. The various embodiments relating to heart valve suturing presented herein can be applicable to heart valves having any type of suturing and/or structural configuration or pattern. Examples of heart valve structures and heart valve suturing techniques that may be applicable to certain embodiments presented herein are disclosed in WIPO Publication No. WO 2015/070249, the entire contents of which is hereby expressly incorporated by reference for all purposes.

FIG. 1 illustrates an implantable prosthetic human valve device 110 according to one or more embodiments. The features of valve 110 described herein can apply to other valves, including other valves described elsewhere herein. For example, the term target device is used throughout this disclosure; the valve 110 can be part of a class of devices included in the term target device. The valve 110 can be, for example, a transcatheter heart valve (THV), balloon-expandable heart valve, and/or mechanically-expandable heart valve. The valve 110 in the illustrated embodiment can generally comprise a frame, or stent, 112, a leaflet structure 193 supported by the frame 112, and a sealing member or skirt 116 secured (e.g., sutured) to the outer surface of the leaflet structure 193. In certain embodiments, the valve 110 may be configured to be implanted in the annulus of a native heart valve of a human, such as an aortic valve. However, the valve 110 can additionally or alternatively be adapted to be implanted in other native valves of the heart, or in various other vasculature, ducts, or orifices of the body, or in grafts, docking stents, docking stations, rings, etc. implanted in the body. The lower end 180, according to the illustrated orientation, of the valve 110 may represent an inflow end, while the upper end 182, according to the illustrated orientation, of the valve 110 may represent an outflow end.

The valve 110 and the frame 112 may be configured to be radially collapsible to a collapsed or crimped state or configuration for introduction into the body using a delivery catheter, and further may be configured to be radially expandable to an expanded state or configuration for implanting the valve at a desired location in the body (e.g., the native aortic valve). In certain embodiments, the frame 112 may comprise a plastic, polymer, shape memory material, or metal expandable material that permits crimping of the valve 110 to a smaller profile for delivery and expansion of the valve. In some embodiments, an expansion device, such as the balloon of a balloon catheter or a tool for mechanical expansion, may be used to expand or help expand the valve 110. In certain embodiments, the valve 110 may be a self-expanding valve, wherein the frame 112 is made of a self-expanding material such as a shape memory material or metal (e.g., Nitinol). Self-expanding valves may be able to be crimped to a smaller profile and held in the crimped state with a restraining device, such as a sheath covering the valve 110. When the valve 110 is positioned at or near the target site, the restraining device may be removed or retracted to allow the valve 110 to self-expand to its expanded, functional size or to a deployed configuration.

The sealing portion or skirt 116 may comprise a single piece or multiple pieces or material (e.g., cloth, polymer, etc.) with opposite ends that are secured to each other to form the annular shape shown in FIG. 1 or extend around a circumference of the valve 110. In certain embodiments, the upper edge of the sealing portion or skirt 116 can have an undulating shape that generally follows the shape of struts of the frame 112. In this manner, the upper edge portions of the sealing portion or skirt 116 can be tightly secured to respective struts with sutures 156. The sealing portion or skirt 116 may be placed on the outside of the frame 112 or on the inside of the frame 112 (as shown) and an upper edge portion of the sealing portion or skirt 116 may be wrapped around the upper surfaces of the frame struts and secured in place with sutures 156. The sutures 156 may serve to provide a durable attachment of the sealing portion or skirt 116 to the frame 112.

The leaflet structure 193 can comprise three leaflets (as shown in FIG. 1) in certain embodiments, which can be arranged to collapse in a tricuspid arrangement. Although a three-leaflet embodiment is illustrated, it should be understood that valve implants sutured according to embodiments disclosed herein may have any number of leaflets, such as, for example, two or four. The leaflets 193 may be formed from separate flaps of material or tissue, such as, for example, xenograft tissue (e.g., bovine pericardium), or all three leaflets can be derived from a single xenograft valve (e.g., a porcine valve). The lower edge of leaflet structure 193 may have a variety of shapes. In certain embodiments, the lower edge of the leaflet structure 193 may have an undulating, curved, and/or scalloped shape that may be sutured to the frame 112. The leaflets 193 can be secured to one another at their adjacent sides to form commissures 184 of the leaflet structure, where the edges of the leaflets come together. The leaflet structure 193 can be secured to the frame 112 using any suitable techniques and/or mechanisms. For example, the commissures 184 of the leaflet structure may be aligned with the support posts 118 and secured thereto, e.g., using sutures, adhesive, clamping portions, crimping, and/or other attachment means. In some embodiments, the point of attachment of the leaflets 193 to the posts 118 can be reinforced, e.g., with bars comprising a relatively rigid material, such as stainless steel.

Figure 2:
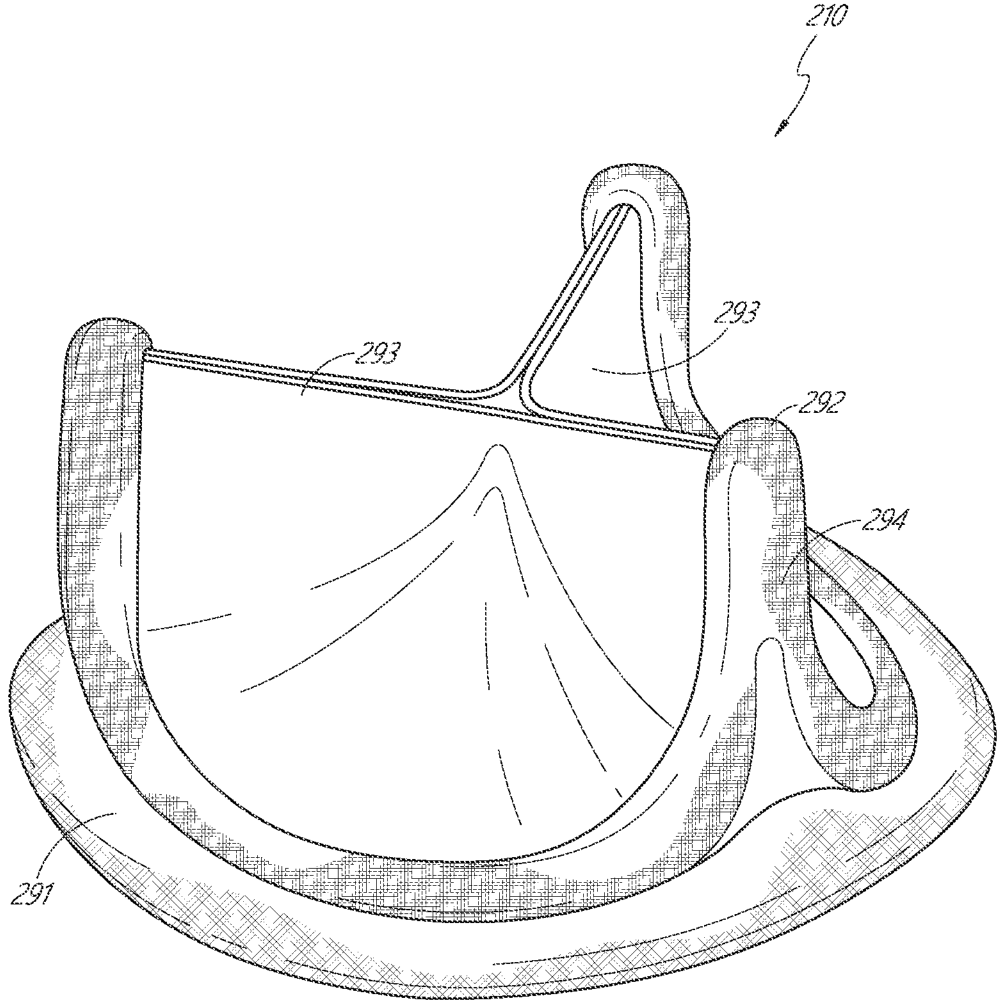
FIG. 2 illustrates a perspective view of a prosthetic heart valve in accordance with one or more embodiments.

FIG. 2 is a perspective view of a prosthetic human heart valve 210 in accordance with one or more embodiments. The heart valve 210 may include a peripheral sealing ring structure 291 configured to provide support for nesting the heart valve 210 in a heart valve cavity and/or resting upon, or attached to, an annulus or other structure of the heart. The valve 210 can further include a frame member 292, such as a metal frame, which may provide support for a plurality of flexible leaflets 293 and can define three upstanding commissure posts 294, wherein the leaflets 293 can be supported between the commissure posts 294. In some embodiments, as shown in FIG. 2, the sealing ring 291 can attach around the periphery of the frame member 294 at the inflow end of the valve 210, with the commissure posts 294 projecting in the outflow direction.

The leaflets 293 may be formed from separate flaps of material or tissue, such as, for example, xenograft tissue (e.g., bovine pericardium), or all three leaflets can be derived from a single xenograft valve (e.g., a porcine valve). The leaflets 293 can be secured and supported both by the commissure posts 294, as well as along arcuate cusps of the frame member between the commissure posts.

Figure 3A:
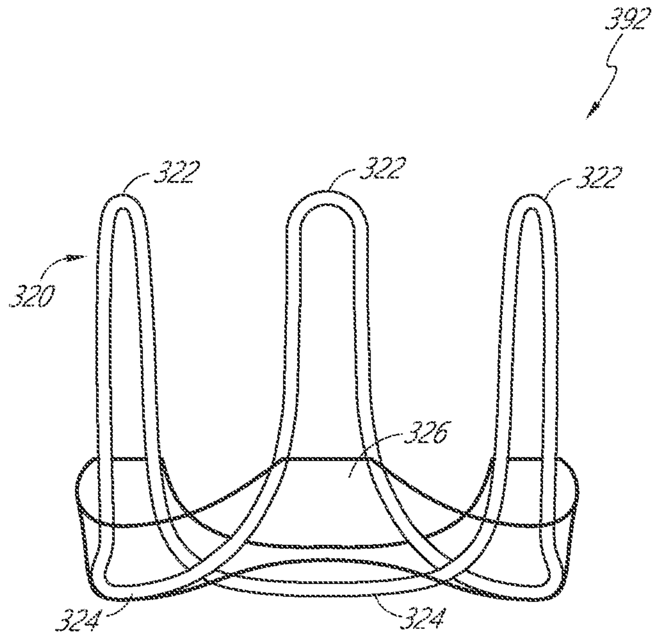
FIG. 3A illustrates a frame for a support stent for a surgical valve in accordance with one or more embodiments.

FIG. 3A illustrates a frame 392 for a support stent for a surgical heart valve such as the valve 210 of FIG. 2. The frame 392 can include multiple cusps curved toward an axial inflow end alternating with multiple commissures 322 projecting toward an axial outflow end, the support stent 392 defining an undulating outflow edge. The support stent 392 can comprise a wireform 320 having three upstanding commissures 322 alternating with three cusps 324 which generally circumscribe a circumference. A stiffening band 326 may be disposed within or without the wireform 320. The inflow edge of the band 326 can conform or at least partially conform to the cusps 324 of the wireform 320 and may be curved in the outflow direction in between in the region of the wireform commissures 322, e.g., as shown in FIG. 3A. In certain embodiments, the support stent 392 provides the supporting structure of a one-way prosthetic heart valve like the valve 210 of FIG. 2.

Figure 3B:
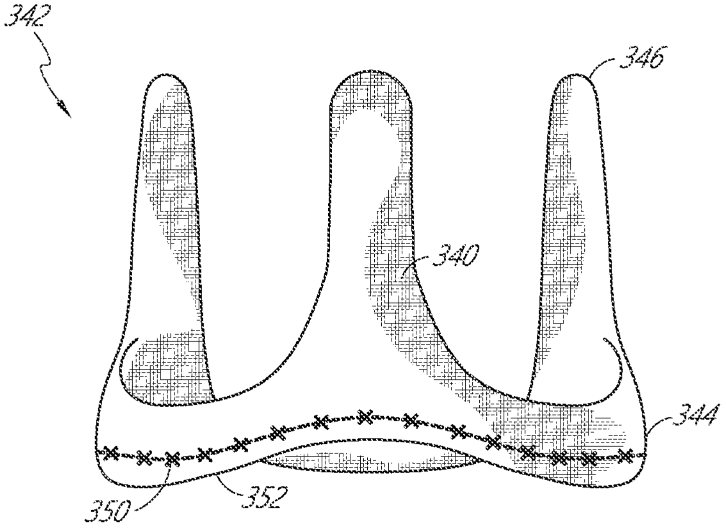
FIG. 3B illustrates the frame of FIG. 3A covered with fabric according to one or more embodiments.

FIG. 3B illustrates the frame of FIG. 3A covered with fabric 340, wherein the fabric 340 may be sutured in one or more portions to secure the fabric 340 as a covering for the frame 392. The fabric-covered support stent 342 may be generally tubular and may include multiple cusps 344 curved toward an axial inflow end alternating with multiple commissures 346 projecting toward an axial outflow end. The support stent 342 may comprise an undulating outflow edge about which the fabric 340 is secured or held. In certain embodiments, a seam 350 may be sutured adjacent an inflow edge 352 that secures the fabric 340 about the support stent. The seam 350 is shown slightly axially above the inflow edge 352 for clarity, although it may be located directly at the inflow edge or even inside the support stent. In one embodiment, one or more seams may be located in other positions along the fabric. The sutures of the support stent 342 may be executed or added in multiple ways. Furthermore, although certain stitches are illustrated in FIG. 3B, the support stent 342 and/or valve implant 210 of FIG. 2 can comprise any type or number of stitches or sutures. For example, the support stent 342 and/or one or more other components of the associated implant device, can also have leaflets and/or other materials sutured thereto.

Figure 4:
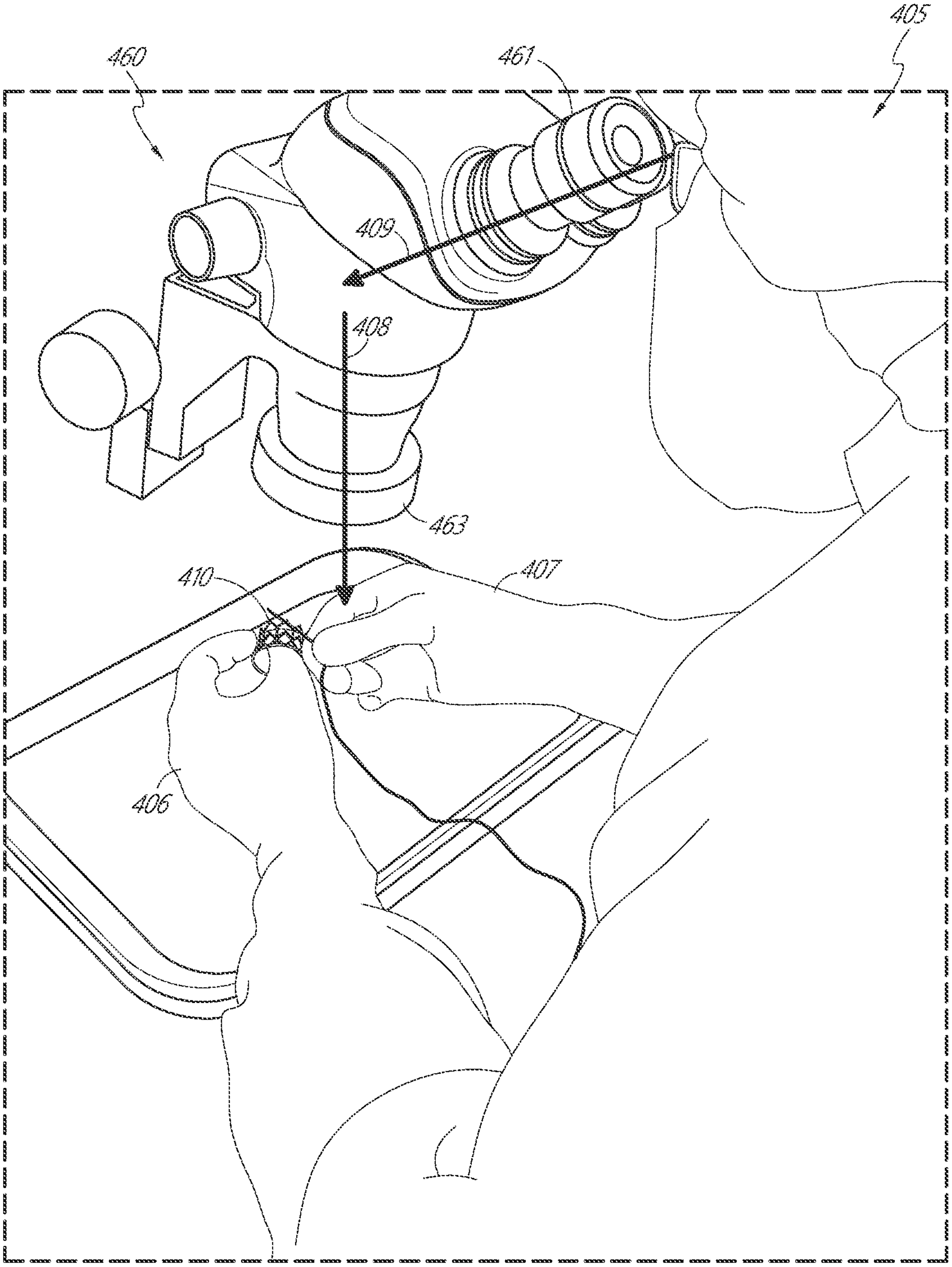
FIG. 4 illustrates an operator performing operations on an implant device in accordance with one or more embodiments.

Suturing of prosthetic heart valve devices and/or other implant devices, such as those described herein, can be performed in various ways. For example, certain handheld processes for suturing prosthetic human implant devices can be implemented in which an operator utilizes both hands for holding, securing, and/or suturing the implant device. FIG. 4 illustrates an operator 405 performing operations on a prosthetic human implant device 410. For example, the operator 405 may suture an outer wireframe of the device 410 to an inner skirt or cloth, as described herein, where the implant device 410 is a transcatheter heart valve device. In some embodiments, the implant device 410 may be a surgical valve device, or other type of implant device. The implant device 410 can be the same as or similar to any of the valves described herein or can be a different type of valve or implant device. The implant device 410 can be a class of device included within the term target device used throughout this disclosure.

As illustrated in the diagram of FIG. 4, in some processes, an operator 405 may need to utilize both of the operator's hands for executing relevant suturing operations. For example, a first hand 406 may be used to hold and/or secure the implant device 410, wherein a second hand 407 may be used to manually operate a suturing needle or the like.

For the operator 405 to effectively execute the relevant suturing operations on the implant device 410, it may be necessary or desirable for the view of the implant device 410 to be magnified or otherwise enhanced in some manner. For example, as shown, the operator 405 may further utilize a magnification system 460, such as a microscope, which may comprise an eyepiece component 461 as well as one or more lenses and/or refractive elements 463. In certain embodiments, the magnification system 460 may be designed such that the operator 405 may have a line of sight 409 at a first angle, wherein the magnification system 460 is configured to at least partially reflect light therein at a downward angle 408 to provide a depth of field at a targeted distance from the refractive elements 463. By holding the implant device 410, or target portion thereof, within the depth of field of the magnification system 460, the operator 405 may be able to observe an enhanced view of the implant device 410 or target portion thereof, which may be desirable or necessary to execute the precise suturing operations for effectively suturing the implant device 410.

In certain configurations, the use of a microscope as a visual aid in suturing implant devices may present ergonomic issues with respect to posture and/or vision of the operator 405. For example, the working plane presented by the microscope, with which the operator may be aligned when operating the microscope, may not adequately conform to the natural body position of the operator. To bring the operator's eyes into necessary proximity with the eyepiece 461 of the magnification system 460, undesirable neck and/or back strain or stress may be caused as the operator 405 maintains the necessary posture for viewing the implant device 410 through the eyepiece 461. Therefore, use of a microscope, or similar magnification or viewing system, may be undesirable with respect to ergonomic and/or vision concerns.

Alternative systems and methods for visual aid in implant suturing may involve, for example, digital video systems, which may help to reduce the possibility of operator neck strain, among other possible benefits. However, such systems may present difficulty with regards to focusing the implant or part being operated on under the camera associated with the video system when the implant or part is manually handled by the operator. With handheld operation, focus of the camera may be blurred and/or distorted when the implant or target part moves or is not aligned correctly with the lens axis, which may result in a loss of depth perception and/or other problems. For example, displays of a camera image can appear blurred due to slow pixel response times, refresh times, etc. when an implant or target part moves. This can be especially problematic when displaying high resolution images or video and/or magnifying the images or video. Furthermore, where the operator is required to hold the target implant, alteration of the viewing angle may further require twisting and/or contorting of the operator's hands in order to position the target implant, which may result in sub-optimal positioning. In addition, the location of the target implant may be such that a different viewing angle is required by the operator to view the target part than is required to view the monitor of the video system, which may cause eyestrain and/or other issues. Alternative solutions for visual aid in implant suturing operations may involve the use of a glass visor or the like, which may provide beneficial performance with respect to hand-eye coordination and/or neck placement. However, such tools may provide relatively poor zooming capabilities, and may cause eyestrain for the operator over extended periods of time.

Figure 5:
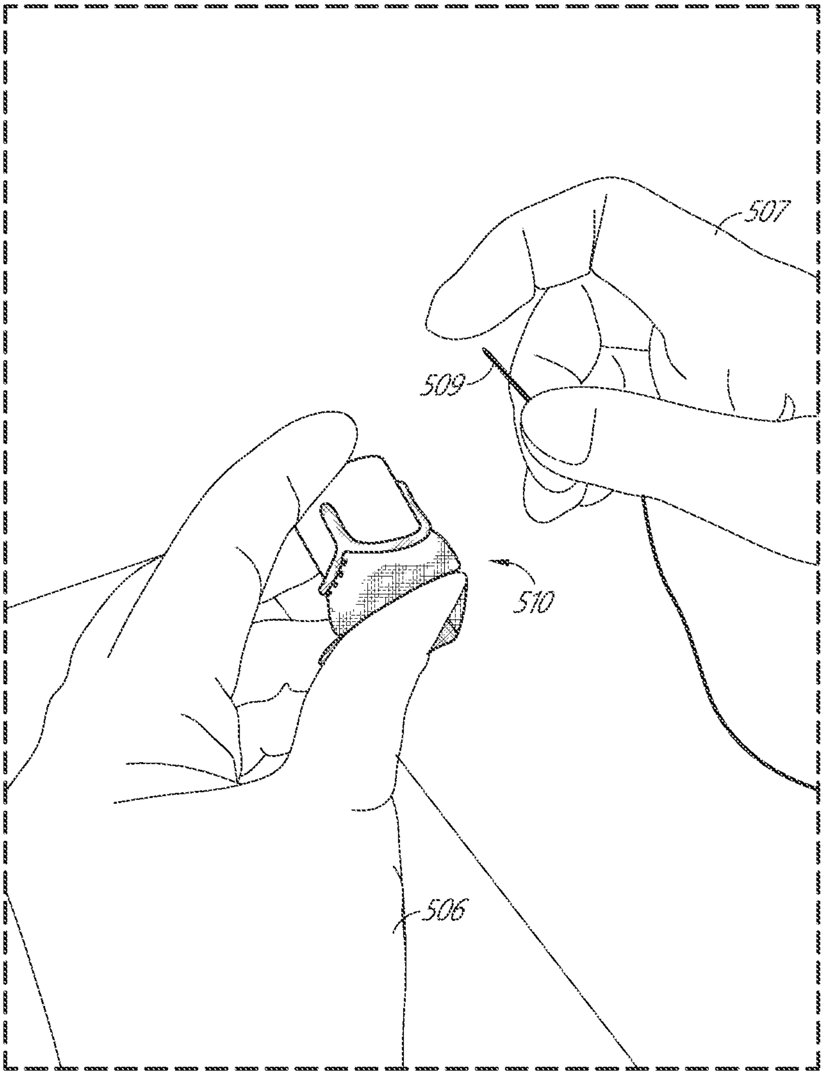
FIG. 5 illustrates a close-up view of a heart valve implant device being sutured using manual holding and suturing according to one or more embodiments.

FIG. 5 illustrates a close-up view of a prosthetic human implant device being sutured using manual holding and suturing, as described above. As shown, for handheld suturing solutions, a first hand 506 may be required to hold the target implant device 510, while a second hand 507 may be required to manipulate the suturing needle 509, or the like. According to certain processes, the operator may be required to hold one or more hands in a substantially constant position over prolonged periods of time to maintain the target implant device 510 (or desired portion thereof) within the depth of field of a microscope. Furthermore, the operator may be required to squeeze, push, pull, or otherwise exert manual force on one or more portions of the target implant device 510 and/or suture needle 509, thereby causing strain on muscles, joints, or the like, of the operator's hands and/or other anatomy. Certain operations may require the operator's hands to exert up to 20 pounds or more of force. Such forces may be required repeatedly throughout a suturing process and may result in various injuries to the operator.

Figure 6:
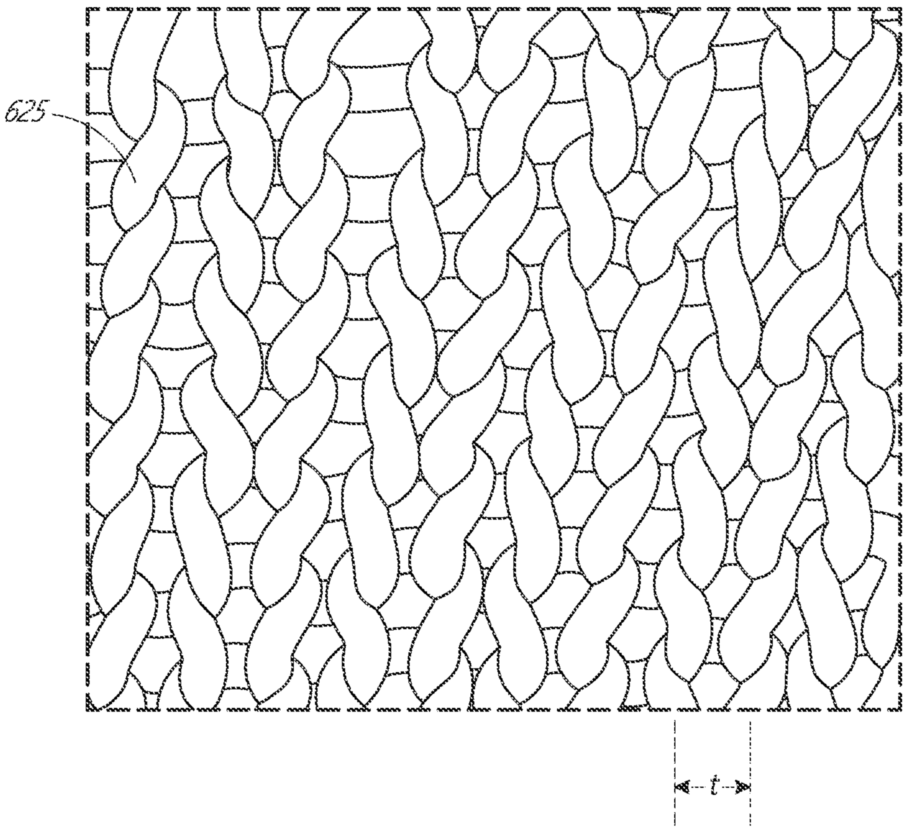
FIG. 6 illustrates a close-up view of a fabric associated with an implant device according to one or more embodiments.

Visual magnification and/or accurate positioning of an implant device may be necessary or desirable due at least in part to the dimensions of the cloth or other material being sutured in an implant suturing operation. For example, FIG. 6 illustrates a close-up view of a fabric associated with an implant device according to one or more embodiments. Such fabrics may comprise woven strands forming ribs having relatively small gaps therebetween. For example, each rib in a fabric region to be sutured may have a thickness t of approximately 0.2 mm, or less. For certain processes, the operator may necessarily or desirably wish to position and sew such a fabric within one-rib accuracy. Therefore, precise positioning and focusing of suturing components and targets is desirable.

Example Suture Assistance Systems with Vision Assist

In certain implementations, suturing (e.g., implant suturing) or other processes (e.g., inspecting a device) could be performed using one or more holder devices, such as a handheld gooseneck holder or mounted holder type device. However, such devices may not be rapidly adjustable to new locations, which may negatively impact performance efficiency or speed. Furthermore, refocusing of a microscope or other vision system to a location associated with such a holder device may be difficult. Handheld holders and tools may require operators to hold the holder or tool with one hand, thereby limiting the ability of the operator to use that hand to adjust the fabric or other material for tensioning and/or realignment.

Accordingly, to address these and other issues, embodiments disclosed herein provide systems and processes for assisting operators in suturing and/or inspecting components and/or devices (e.g., prosthetic human implant devices) using suturing assistance systems having an automated fixture and a vision assist system. Such operator or procedure assistance systems can be configured to use the automated fixture to articulate a target device, or a component of a target device, and to use the vision assist system to project a visual indicator on the target device to indicate a location for forming or inspecting a stitch. The assistance systems can be configured to reposition the component (e.g., using the automated fixture) and/or the visual indicator (e.g., using the vision assist system) to anticipate a subsequent position (e.g., a subsequent suture position, review or inspection position, or other position). In certain embodiments, the assistance systems can include a visualization system having an imaging system (e.g., a camera) and a display. The display can include visual aids to assist the operator in locating and/or interpreting an operation (e.g., a suture operation, review or inspection operation, processing operation, training operation, or other operation) to be performed. For example, the display may provide crosshairs, visual aids, overlays, comparative images, patterns, maps, and/or a type of reticle, or the like, to indicate the desired position or result (e.g., the desired suture position or completed suture). Thus, the visualization system can be used to augment or complement the visual assistance provided by the vision assist system. The visualization system can include automatic focusing and/or automatic zooming capabilities. This advantageously re-focuses and/or adjusts the magnification of the image of the target device when it is moved to a new position so that it is still in focus on the display. Advantageously, automatic re-focusing and/or zooming also allows the visualization system to maintain locational and dimensional consistency or accuracy on the display as the target device is moved from position to position.

Embodiments disclosed herein may provide improved ergonomics for operators, which may reduce medical costs and/or liabilities associated with hand, neck, shoulder, and/or vision injuries, for example. Furthermore, embodiments disclosed herein may provide improved reliability and/or repeatability for suturing processes, review or inspection, or other processes. For example, suturing an implant device or heart valve can require suture accuracy within a millimeter, half a millimeter, or less, but a suture location may be easily missed between ribs or threads, especially when implementing dual-handheld suturing procedures. Embodiments of the present disclosure can facilitate improved precision and can also provide the freedom of only requiring a single hand for certain suturing operations and/or other operations (e.g., inspection, processing, etc.).

Positional accuracy may be improved with respect to embodiments of the present disclosure through the use of vision assist systems incorporating a light source, optical elements, articulation arms, actuators, automated fixtures, or a combination of more than one of these. Such vision assist systems can be used to project a visual indicator onto a target device to aid in locating, forming, reviewing, and/or inspecting a stitch, such as with respect to frame and skirt suturing for a transcatheter heart valve. The visual indicator can be used to provide visual cues and/or feedback to an operator during manufacturing and/or inspection.

Embodiments disclosed herein and the incorporation of features according to the present disclosure can be used for training and/or technology transfer that may ultimately result in substantially reduced process or operation times and can help reduce the difficulty of operations and procedures. For example, it can be relatively difficult to convey training to an operator with respect to a particular procedure, and improved solutions disclosed herein can help reduce the complexity of certain procedures with enhanced training and/or by diverting certain procedures to mechanical components configured to manipulate the target device or component as necessary. Training of operators may be completed with improved efficiency, thereby potentially reducing costs and time. Embodiments can be used to guide operators through desired procedures or operations and demonstrate correct positioning and results. Quality-control feedback can also be provided to further improve quality for manufacturing and training. For example, heart valve implant suturing processes can be relatively labor-intensive and involve relatively long process times, which can result in increased costs and/or injuries. Correct positioning of sutures can be shown to aid training and to reduce the necessity for memorizing the suturing procedure when manufacturing a target device. The disclosed assistance systems may be programmed to move to key locations for inspection where a visual indicator can be used to identify a stitch or stitches to be inspected. In some embodiments, image recognition software may be able to detect issues, e.g., to detect whether a suture looks correct or incorrect. Image recognition can be provided by comparing an image acquired of a suture with a catalog of images of correct sutures. Feedback from the image recognition software can be provided via the visual indicator and/or via a display. Similar image recognition software can be used for other processes as well to detect whether the target device appears as expected after a particular step, process, operation, etc. Various systems and/or devices disclosed herein may allow for fully automated processes or partially automated processes (e.g., at least partially automated implant suturing).

Figure 7A:
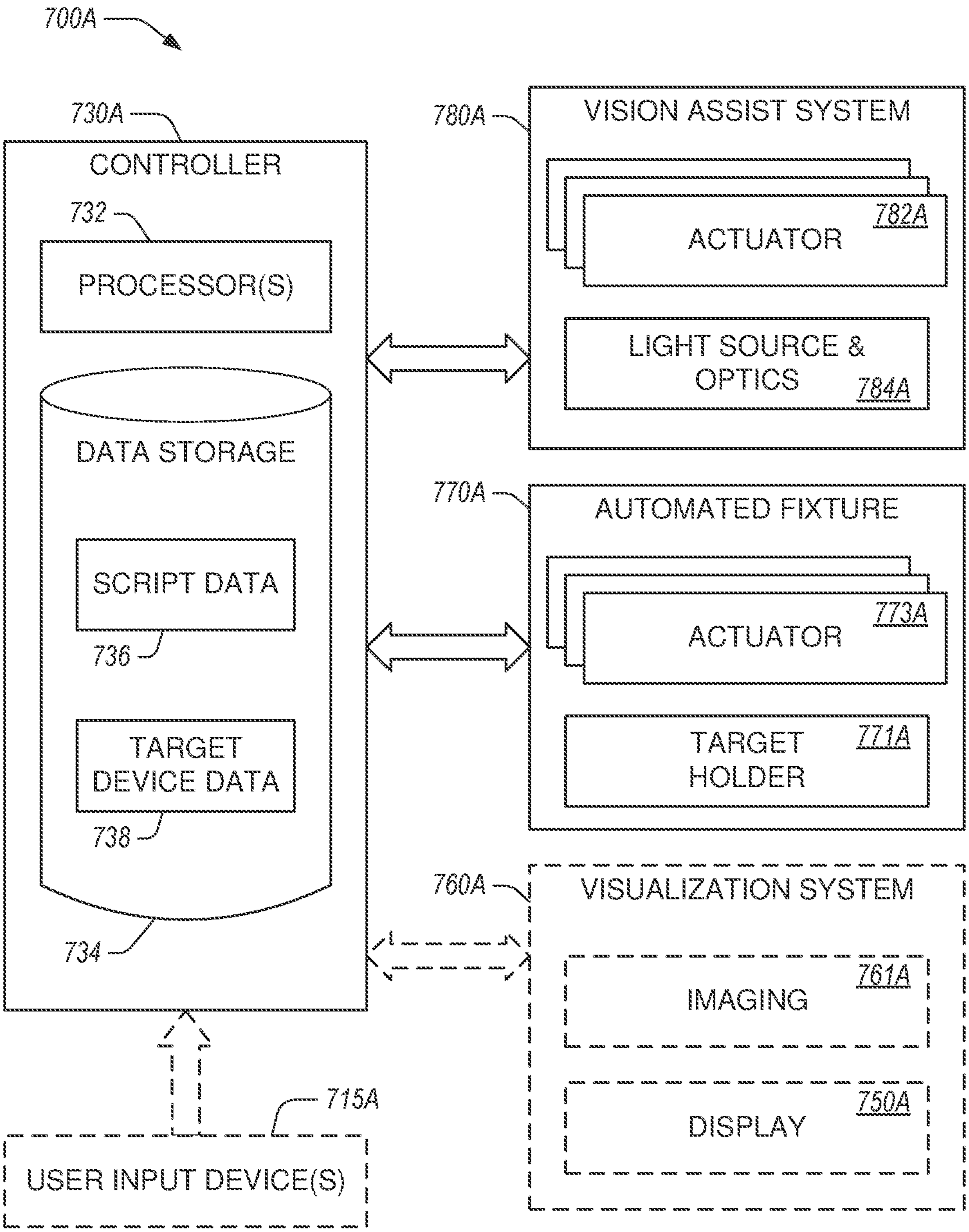
FIG. 7A illustrates a block diagram illustrating a suturing assistance system in accordance with one or more embodiments.

Embodiments disclosed herein provide for systems, devices, methods, etc. for executing one or more procedures or operations (e.g., suturing operations, attachment operations, review or inspection operations, and/or other operations) for prosthetic heart valve implant devices for humans and/or other types of devices or components. FIG. 7A illustrates an example suturing assistance system 700A according to one or more embodiments. One or more components of the system 700A may be utilized for suturing heart valve devices or other implant devices, as described herein, and/or may be utilized for inspecting sutured heart valve devices. The system 700A includes a controller 730A configured to interface with a vision assist system 780A to provide a visual indicator on a target device and to interface with an automated fixture 770A to control positioning of the target device. In some embodiments, the controller 730A is also configured to interface with a visualization system 760A to acquire images of the target device and/or to display images associated with a manufacturing or inspection procedure for the target device. In certain embodiments, the controller 730A also receives input from user input device(s) 715A.

The controller 730A can comprise one or more hardware and/or software components designed to generate and/or to provide control signals and/or data associated with one or more steps of a suturing process or other process. The control signals can be sent to the vision assist system 780A, the automated fixture 770A, and/or the visualization system 760A. In some embodiments, the user input device 715A can provide signals to the controller 730A that then trigger a change in control signals to one or more of the vision assist system 780A, the automated fixture 770A, and the visualization system 760A. For example, the controller 730A can include one or more processors 732 and one or more data storage devices or components 734, which can include volatile and/or nonvolatile data storage media. Although illustrated as a separate component in the diagram of FIG. 7A, the controller 730A can be a component of the vision assist system 780A, the automated suture fixture assembly 770A, or the visualization system 760A, or the controller 730A can be distributed among two or more of the vision assist system 780A, the automated fixture 770A, and the visualization system 760A.

In some embodiments, the data storage 734 is configured to store script data 736 (e.g., suture process script data, inspection process script data, etc.), which can include data indicating positioning of one or more components of the system 700A for various steps and/or stages of the suturing process or other process (e.g., for inspection, procedures, etc.). A process comprising a plurality of steps can be represented at least in part by numeric or other data sets making up the script data 736. These data sets can represent positioning and other related information for one or more components of the system 700A for each respective step or stage of the process. For example, a suturing process comprising a plurality of suturing steps can be represented at least in part by numeric or other data sets representing positioning information for one or more components of the system 700A for each respective step or stage of the suturing process. The script data 736 can also include images, video, text, and the like associated with steps in the suturing or inspection process. For individual steps or portions of a step, the script data 736 can provide images, video, and/or text to be displayed (e.g., on a display 750A of the visualization system 760A) to assist an operator in performing elements of the relevant stage of the process.

In some embodiments, the data storage 734 is configured to store target device data 738 (e.g., target device size, target device components, target device type, three-dimensional model of a target device, target device geometry, target device surface topography, etc.). The target device data 738 can be used to create a three-dimensional topological map of the target device. The target device data 738 can include information about a variety of different target devices that may be manufactured using the system 700A. In some embodiments, the target device data 738 can be used by the vision assist system 780A to determine a location of the target device in space based at least in part on a position of the automated fixture 770A (e.g., determined from the script data 736). The vision assist system 780A can then determine a position and/or orientation of a light source 784A to produce a visual indicator on the target device at a targeted location.

The vision assist system 780A includes one or more actuators 782A and a light source 784A, wherein the light source 784A can also include appropriate optics to produce and/or direct a visual indicator. The one or more actuators 782A can be configured to position the light source 784A or components of the light source 784A (e.g., optics such as lenses, mirrors, fiber optic cables, etc.) to direct a visual indicator to a targeted location on the target device. The actuators 782A can be motorized, pneumatics, or the like, and may be similar to the actuators, articulation arms, gimbals, and the like described elsewhere herein with respect to automated fixtures.

The light source 784A of the vision assist system 780A can include any suitable combination of a source or sources of lights and optical components to form a visual indicator projected or directed to a surface of the target device. The light source 784A can include, for example and without limitation, lasers, projectors, light emitting diodes (LEDs), lamps, and the like. The optics of the light source 784A can include, for example and without limitation, mirrors, lenses, fiber optics, wave guides, diffusers, combiners, polarizers, filters, shutters, and the like.

The combination of the actuators 782A and the optics of the light source 784A can be used to provide the visual indicator at a targeted location. For example, the actuators 782A can be used to provide coarse positioning of the light source 784A whereas optical elements can be used to provide fine positioning control of the light from the light source 784A to produce the visual indicator at the targeted location with sufficient accuracy and precision. As another example, the actuators 782A can be used to position the light source 784A so that it does not interfere with an operator, so that it does not interfere with the automated fixture 770A, and/or so that it does not interfere with operation of the visualization system 760A. In such embodiments, the optics of the light source 784A can be used to direct light from the light source 784A to the targeted location on the target device.

As an example, the light source 784A can include one or more lasers. The one or more lasers can produce collimated light that is directed to a surface of the target device. In some embodiments, different lasers can be used to generate different colors of light wherein the different colors can be used to provide different visual indicators on the target device. The optics can include mirrors or other components to redirect the laser light. For example, one or more movable mirrors can be used to rapidly scan the laser light in a pattern on a surface of the target device to produce a design or shape (e.g., a circle, an 'X', or the like) as the visual indicator.

As another example, the light source 784A can include a projector configured to generate an image. The projector can include lenses and/or mirrors to generate a desired image or light pattern on the target device. The projector can include any suitable combination of light sources (e.g., lasers, LEDs, laser diodes, lamps, etc.) and image engine (e.g., LCD, DLP, or the like) to generate the desired image or light pattern.

As another example, the light source 784A can include optical fibers to direct light to targeted locations on the target device. The optical fibers or fiber optic cable can receive light from a suitable light source (e.g., lasers, LEDs, laser diodes, lamps, or the like) and can direct the light through the optical cable or fiber optic to the target device. In such embodiments, the actuators 782A can include components coupled to a light-emitting end of the optical fiber so that the light-emitting end is positioned to produce a visual indicator at the targeted location. In some embodiments, two or more optical fibers can be used to generate simultaneous visual indicators at different positions on the target device. In addition, different colors of light can be provided to the optical fibers to provide changes in colors for the visual indicator.

In some embodiments, the light source may be used to generate two or more simultaneous visual indicators on the target device. For example, a first visual indicator can be provided on an outer surface of the target device to indicate an entrance location for a needle and a second visual indicator can be provided on an inner surface of the target device to indicate an exit location for the needle. As another example, a first visual indicator can be provided on the target device to indicate a starting position for a process (e.g., forming sutures or inspecting sutures) and a second visual indicator can be provided on the target device to indicate an ending position for the process. As another example, a first visual indicator can be provided on the target device to indicate a first position and a second visual indicator can be provided on the target device to indicate second position wherein one or more steps is to be performed between the first and second positions (e.g., forming or inspecting sutures between the first and second positions).

The visual indicator produced by the light source and optics 784A can be configured to provide information to an operator. For example, properties of the visual indicator can indicate certain information. Properties of the visual indicator can include, for example and without limitation, color, pattern, persistence (e.g., solid or flashing), or any combination of these or the like. The information indicated by the visual indicator can include, for example and without limitation, the correctness of a formed stitch, the type of stitch to be formed, an entrance location, an exit location, or any combination of these or the like. By way of example, the visual indicator can indicate that a stitch is performed correctly using a green light, a solid light, and/or a circle, and the visual indicator can indicate that a stitch is performed incorrectly using a red light, a flashing light, and/or an 'X'. By way of example, the visual indicator can indicate the type of stitch (e.g., in-and-out stitch, a whip stitch, etc.) to be performed using a pattern. By way of example, the visual indicator can indicate an entrance location for a needle using a solid light and an exit location for a needle using a flashing light. These examples are merely illustrative and should not be understood to limit the available combinations of colors, patterns, persistence, and the like to indicate relevant information during a suturing or inspection procedure.

The automated fixture 770A can receive control commands or directives from the controller 730A to direct one or more components of the automated fixture 770A according to a particular process (e.g., a suture-assist process). Although the automated fixture 770A may be referred to herein as an automated suture fixture assembly, the automated fixture 770A may also be an automated fixture or articulation device used for other operations or procedures beyond suturing or sewing.

The automated fixture 770A can comprise one or more components configured to articulate, operate, and/or position one or more motorized actuators 773A to present a target device (e.g., a heart valve or suture target), in a desirable or suitable position or presentation for convenient engagement or interaction therewith by an operator executing at least part of a process (e.g., a suturing process). In certain embodiments, the automated fixture 770A includes a plurality of actuators 773A that are mounted, attached, or connected to one another in a suitable configuration to provide a desirable range of motion for the automated fixture 770A for the purpose of articulating the target device associated with or held by a target holder 771A of the automated fixture 770A. In certain embodiments, the target holder 771A can be associated with, or connected to, one or more of the actuators 773A. The actuators 773A can each comprise one or more rotating, translating, or otherwise articulating members driven by a motor, a piston, or the like. Examples of automated fixture assemblies and associated components are described in greater detail herein with reference to FIGS. 8, 11, 18-25, and 28-30.

The actuators 773A can be configured to provide a number of degrees of freedom of movement for the target holder 771A and, consequently, the target device coupled to the target holder 771A. In some embodiments, the number of degrees of freedom is greater than or equal to 3, greater than or equal to 4, greater than or equal to 5, or greater than or equal to 6. The degrees of freedom can include positioning in any of the three spatial dimensions (e.g., movement in the x-axis, y-axis, and z-axis; horizontal movement, vertical movement, or a combination of horizontal and vertical movement), rotation (e.g., rotation about the x-axis, about the y-axis, and/or about the z-axis), and/or rotation of the target holder 771A around a longitudinal axis of the target device (e.g., keeping the position and pointing direction of the target device fixed while rotating the target device around its longitudinal axis to expose a different portion of the target device to an operator and/or visualization system 760A).

In certain embodiments, the controller 730A can provide control signals for directing the positioning of the actuators 773A based on the script data 736 (e.g., a suture process script) and/or user input provided by an operator through the user input device(s) 715A. The user input device 715A can be used by an operator to provide input directing operation of the controller 730A and/or automated fixture 770A. For example, user input device 715A can comprise any suitable user input interface, such as a mechanism for user input in connection with a graphic user interface associated with an electronic display, wherein an operator can provide input through interaction with the interface. In some embodiments, the user input device 715A can comprise one or more physical switches, buttons, pedals, sensors, or the like, wherein a user may provide input through engagement of such mechanism(s). In some embodiments, the input can be provided using voice commands and/or voice recognition software. In some embodiments, the user input device 715A comprises a foot pedal that can be pressed or otherwise engaged by the operator substantially at the same time as the operator is interacting with one or more other components of the suturing system 700A. For example, the operator can activate the foot pedal while sitting or standing at a suturing station and engaging with the target device with one or more hands of the operator. For example, the operator can engage the foot pedal as a signal to advance from one step or stage of the present suturing operation to a subsequent step or stage. That is, the input device 715A can provide input to the controller 730A to advance the system 700A through a script moving the automated fixture 770A and target device to each position in a sequence.

In some embodiments, the system 700A includes a visualization system 760A, which can be configured to perform various imaging functions to assist with the suturing procedure being executed by the operator. The visualization system 760A can include one or more imaging devices or cameras 761A. For example, multiple imaging devices or cameras can be used to add dimensions or depth to the images. The visualization system 760A can be configured to generate an image, such as a close-up image and/or high definition image, of the target device (e.g., an image of a portion of the target device to be sutured, inspected, treated, etc.) and/or associated components of the automated fixture 770A for the purpose of providing a visual aid for the operator in executing suturing operations, inspections, or other operations. The visualization system 760A can capture image data for quality control or other purposes at various stages of the suturing procedure or other operation. The visualization system 760A can include a display 750A, such as an electronic computer display, television, monitor, handheld device, tablet, or the like. Therefore, in certain embodiments, the operator can view enlarged imaging of a target device (e.g., an image of a portion of the target device to be sutured) while executing suturing operations thereon, or otherwise inspecting or engaging therewith. In certain embodiments, the visualization system 760A maintains a constant focus or depth of field during multiple steps of a suturing process, while the automated fixture 770A articulates the target device in such a way as to bring a target portion of the target device into the depth of field of the imaging system 761A. The automated fixture 770A holds the target device in place during each step of the process so that the target device remains in focus.

The display 750A can be used to display a live image of the target device to aid the operator. The display 750A may also be used to display information relevant to the current procedure (or step within the current procedure) being performed. The display 750A can show a computer model of the target device to illustrate the proper position and formation of a suture or stitch for the purpose of replicating the stitch by the operator or for the purpose of providing a model of a correct stitch for inspection and quality assurance purposes. The user input device 715A can be used to interact with the display 750A to change the display between steps in the procedure, between illustrations and videos, between a live image and a model of the target device, or the like. This can allow the operator to compare relevant information from the display 750A with what the operator is seeing with the aid of the vision assist system 780A on the actual target device being sutured or inspected.

In certain embodiments, the display 750A can be configured to present thereon operator instructions for executing suturing operations or other operations, as well as other information which may be pertinent to the procedure or otherwise associated with the procedure (e.g., step by step instructions, reference images of correctly completed suture steps or procedure steps, warnings, cautions, tips, suggestions, FAQs, etc.). The operator instructions can be derived from the script data 736, as an example. In certain embodiments, the display 750A can present timing elements, which can be used to improve efficiency and/or aid the operator in determining points or periods of time during which certain operations are to be executed. In some embodiments in which the target implant device may comprise materials that are required to maintain a certain degree of moisture in order to retain desired functional properties or qualities (e.g., tissue used to form leaflets of a valve can be required to maintain a certain degree of moisture), reminders and/or instructions may be presented on the display 750A to the operator to remind the operator to saturate or moisten such components. Furthermore, in certain embodiments, the display 750A can present qualitative measurement or analysis information with respect to the procedure being executed by the operator, such as sensed characteristics of the implant device and/or one or more components or features thereof, such as moisture levels, tension readings with respect to certain stitches, or the like. The system 700A can include sensors configured to detect these characteristics, e.g., moisture level sensors, tension sensors, etc. The system 700A can include a timer, clock, or other time tracking device or operation to track how long the various steps, operations, procedures, etc. take and/or to allow an operator or other person (e.g., a supervisor) to review different times or images associated with different times.

In certain embodiments, still images can be captured as displayed on the display 750A and/or captured by the imaging system 761A. Such captured images can be used to provide quality-control data points. For example, image file data can be compiled and stored in association with the specific implant device of the procedure, the procedure, and/or the operator involved in the procedure. This information can be used to evaluate the quality and/or other aspects of the implant device, procedure, and/or operator. The display 750A can be positionable for viewing by the operator in any desirable position, which may allow for relatively low-stress posture and/or interaction of the operator to improve ergonomics.

With respect to the actuators 773A, 782A of the automated fixture 770A and the vision assist system 780A, the actuators 773A, 782A can include a motor, such as a DC, AC, or brushless DC motor. The motor can be a servo motor. In certain embodiments, the motor is controlled using pulse-coded modulation (PCM), as directed by motor control circuitry. For example, the motor control circuitry can apply a pulse application for a certain period of time, wherein the angular positioning of a rotor component is determined at least in part by the length of the pulses. The amount of power applied to the motor may be proportional to the rotational distance of the rotor.

In certain embodiments, the actuators 773A, 782A can be servo actuator devices including one or more servo feedback component(s), such as a position sensor (e.g., a digital encoder, magnetic encoder, laser(s), etc.). Use of servo feedback component(s) can be desirable in order to achieve a desirable level of confidence that the actuators are positioned as directed by the controller 730A with an acceptable degree of accuracy. The servo feedback component(s) can provide an analog signal to the motor control circuitry indicating a position and/or speed of the rotor, which can advantageously allow for relatively precise control of position for faster achievement of a stable and accurate rotor position. Relatively accurate positioning of an implant device may be necessary or desirable due at least in part to the dimensions of the cloth of a heart valve or other implant device that is sutured in an implant suturing operation using the automated fixture 770A. For example, the fabric being sutured may comprise woven strands forming ribs having relatively small gaps therebetween. In certain embodiments, the automated fixture 770A may be required to articulate a suture target prosthetic human implant device within 0.2 mm accuracy, or less. Although servo motor devices and components are described herein in the context of certain embodiments, in certain embodiments, one or more actuators 773A, 782A comprises stepper motors or other types of motor subsystems.

The actuators 773A, 782A can further comprise motor control circuitry, which can drive the motor according to the control signals received from the controller 730A. In certain embodiments, the motor, in combination with the servo feedback mechanism and/or motor control circuitry, can advantageously be configured to retain the rotor and/or attached support member in a set position for desired periods of time. The motor can provide relatively smooth commutation and/or accurate positioning of the associated actuators 773A, 782A. The motor can be relatively powerful relative to its size and may draw power proportional to the mechanical load present on the rotor and/or associated support member.

In certain embodiments, the servo feedback component comprises a potentiometer that is connected to the rotor, which can be considered the output device of the actuator 773A, 782A. The rotor can link to the potentiometer and control circuitry, wherein the potentiometer, coupled with signals from the control circuitry, controls the angle of the rotor (and associated support member) across a rotational range, such as between 0°-180°, or further. In certain embodiments, the rotational range of the rotor can be restricted by one or more mechanical stops, which may be built into associated gear mechanism(s). The potentiometer (or other servo mechanism, such as an internal rotary encoder) can allow the control circuitry to monitor the current angle of the motor and/or rotor. When the rotor is at the correct or targeted angle or position, the motor can idle or lock in place until the next positioning signal is received from the controller 730A.

By way of example, the assistance system 700A can be configured to fix the target device in space. The system 700A can be configured to determine in three-dimensional space the location of surfaces of the target device and critical or important locations on those surfaces. The system 700A can be configured to move the target device along multiple degrees of freedom such that it is able to position the target device in an advantageous or optimal location for an operator to work (e.g., suture, inspect, etc.) on the target device. The vision assist system 780A can be configured to include a light source 784A (e.g., a laser pointer, a back light, a blacklight) that can be used to alert or otherwise convey information to the operator of a correct location for operator-assisted work (e.g., placing a needle through a material to form a suture). The system 700A can receive user input, allowing the operator to interact with the various components of the system 700A. This can be done to indicate completion of a step in a larger procedure, allowing the system 700A to proceed to the next step or to verify the completed step or steps. Upon completion of the step, the system 700A moves the target device to the next location and can adjust the vision assist system 780A and/or visualization system 760A accordingly. This can be repeated multiple times to complete the script or pre-programmed procedure. The system 700A can include multiple recipes or scripts in the script data 736 corresponding to different assembly patterns for different devices. The system 700A can be configured to verify correct completion of a suturing step in real time using machine vision systems (e.g., imaging and image analysis systems). The system 700A can be configured to alert the operator (e.g., using the visual indicator) if the step was performed incorrectly. In addition to the visual indicator on the target device, the system 700A can display a still or live image of the target device on the display 750A and can display the correct suture location superimposed or highlighted on the displayed image of the target device. The visual reference on the display 750A can assist the operator to perform the work correctly. The system 700A may also display the appropriate standard operating procedure to be performed and can be indexed by the user input device(s) 715A in relation to the assembly or inspection operation being performed. The system 700A can be configured to perform a holistic quality verification at different points during the sequence of assembly to confirm that operator-assisted assembly was performed correctly. For example, after steps have been performed in a sequence, the system 700A can automated positioning of the visualization system 760A and the vision assist system 780A to verify the formed stitches. In some embodiments, the system 700A can be part of a fully automated system.

The system 700A can be used to manufacture or inspect a target device using a script or recipe stored in the script data 736. As an example, a script or recipe can include instructions on forming more than 100 stitches on the target device. An operator can initialize the procedure by logging in, scanning an ID, loading the particular script data, and physically loading the target device into the automated fixture 770A. The operator can then push a foot pedal (e.g., provides user input via the user input device 715A) to begin the script. The automated fixture 770A orients and positions the target device based on the script data. The vision assist system 780A points the light source 784A and generates a visual indicator at a targeted location on the target device. The display 750A displays the operating procedure for the first step. The operator follows the operating procedure using the visual indicator as a guide. Upon completion of the step, the operator pushes the foot pedal. The system 700A uses the visualization system 760A to verify the suture is correctly formed in the correct position. This can be accomplished by using the imaging system 761A to acquire an image at the location of the visual indicator. Once the stitch is verified, as indicated by the visual indicator and/or the display 750A, the operator can depress the foot pedal again to move to the next step. This process can be repeated until the script is complete. The system 700A can log the timestamp of each user input and completion of an automated process. This may be used to determine performance metrics and enable comparison among operators.

The system 700A provides a number of advantages. For example, the system 700A can help improve operator performance, reduce the number of injuries to operators, improve speed and efficiency of inspection and manufacture, reduce the required skill to manufacture the target device, identify mistakes during manufacturing, automate decision points for the operator, and the like.

The system 700A can be designed to manufacture medical devices. As such, the system 700A can be clean room compliant and can exclude the use of micro-biologicals, etc.

Figure 7B:
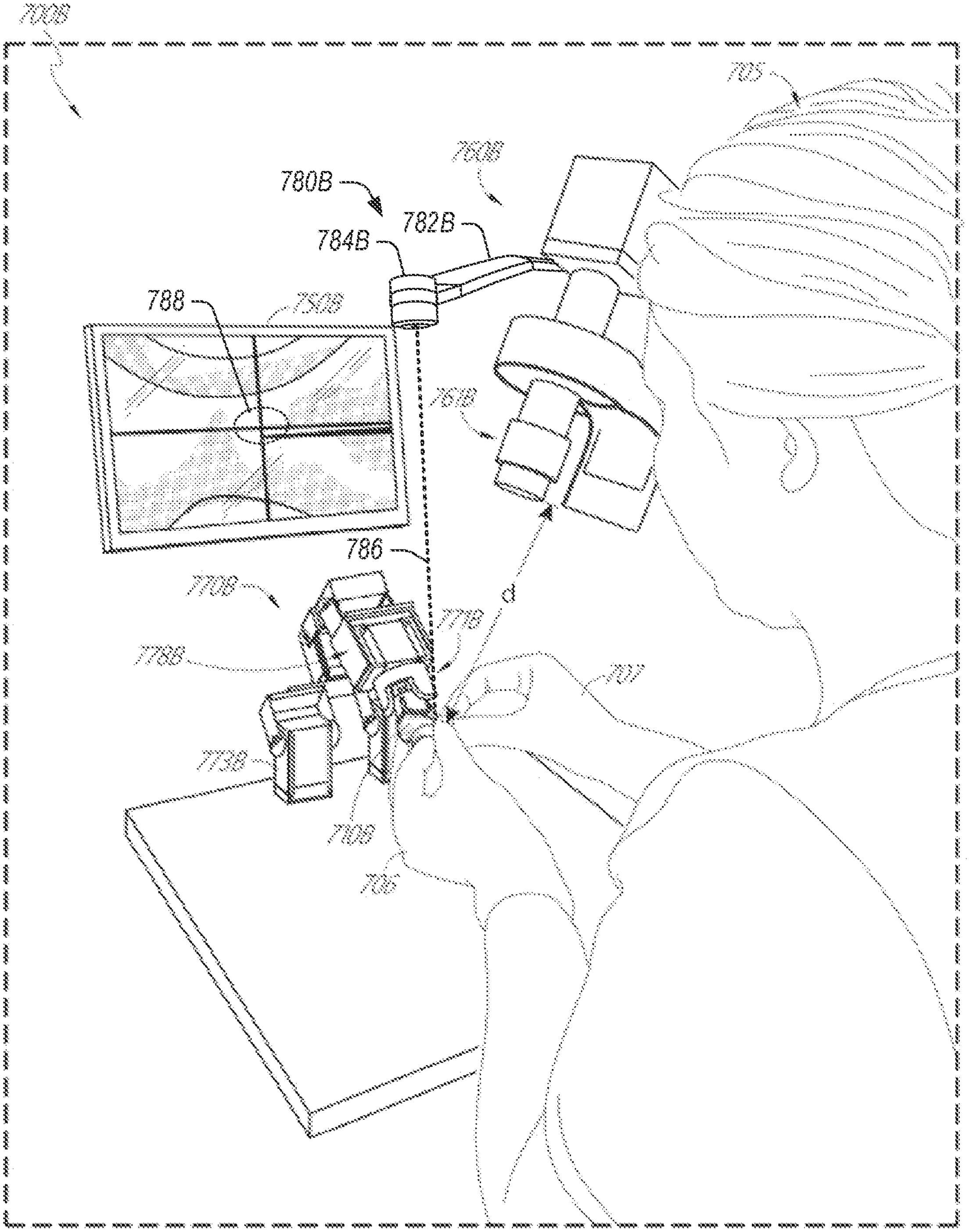
FIG. 7B illustrates an operator executing suture operations with respect to an implant device using a suture assistance system in accordance with one or more embodiments.

FIG. 7B illustrates an operator 705 executing suture operations with respect to a prosthetic human implant device (e.g., heart valve) 710B using a suture assistance system 700B (which may also be used as an inspection assistance system or may be referred to as an operator assistance system or procedure assistance system) in accordance with one or more embodiments. Although a plurality of components and devices are illustrated in the assistance system 700B of FIG. 7B, it should be understood that suture or inspection assistance functionality may be implemented in systems having one or more additional components and/or systems that omit one or more components illustrated in FIG. 7B.

The system 700B includes a vision assist system 780B that includes an articulation arm 782B and a light source 784B. The articulation arm 782B provides multiple degrees of freedom for positioning and orienting the light source 784B to produce light 786 (e.g., collimated light, an image, or the like) that results in a visual indicator 788 being provided on the target device 710B. The visual indicator 788 is shown on the display 750B as an ellipse, but it should be understood that the visual indicator 788 can possess any suitable properties (e.g., color, shape, pattern, persistence state, or the like) described herein. Similarly, the light source 784B is illustrated as providing a beam of light 786, but it should be understood that the light source 784B can also include optical fibers that direct light to the target device 710B, as described elsewhere herein.

The system 700B also includes an automated fixture 770B, which may comprise one or more actuator devices (e.g., servo actuator devices), which may be coupled in one of various configurations allowing for an articulation arm 778B to be articulated to provide multiple degrees of freedom when manipulating and positioning the coupled implant device 710B. For example, the automated fixture 770B can be configured to articulate the arm 778B towards and/or away from the operator 705, up and/or down, in a clockwise and/or counterclockwise direction relative to one or more different axes of rotation (e.g., to move or flip the inflow end and outflow end so one or the other is closer to the operator), in various directions or positions relative to x-, y-, and z-axes, and/or in other directions or movements. Furthermore, the arm 778B of the automated fixture 770B and/or an associated implant holder component 771B can be configured to rotate (e.g., rotate about a central or longitudinal axis of the holder 771B and/or of the target device 710B) clockwise or counterclockwise in order to present different portions or regions of the implant device 710B to the operator 705. A distal arm portion 778B of the automated fixture 770B can allow for the operator 705 to move the target device 710B in a position to expose one or more portions of the implant device 710B (1) to a visualization system 760B (e.g., a camera or microscope assembly), or lens thereof and/or (2) to the operator 705 (e.g., to the operator's hand and/or eye) to perform a procedure (e.g., a suturing step, inspection step, etc.).

In certain embodiments, the automated fixture 770B comprises a plurality of motorized actuators (e.g., servo actuators) physically coupled to one another. By constructing the automated suture fixture 770B using a plurality of motor components (e.g., servo motor components), the system 700B may be relatively inexpensive and/or advantageously provide an enhanced range of motion, as well as multiple axes of rotation. In certain embodiments, the automated suture fixture 770B comprises a plurality of actuator devices (e.g., servo actuator devices) daisy-chained together and implemented using a software script to provide cooperative functionality for the purpose positioning the implant device 710B. For example, the actuator devices or servo actuator devices (e.g., servo motor devices) can be mounted, or configured to be mounted, horizontally or vertically or at an angle, and may be articulated in any desirable direction. For example, the automated suture fixture 770B can be configured to articulate in a snake-like and/or crane-like configuration. FIGS. 18-25 and 28-30 illustrate examples of snake-like configurations of an automated fixture that can be used in suturing procedures as an automated suture fixture and/or in other procedures. It should be understood that similar configurations may be used as part of the vision assist system 780A, 780B to position and orient the light source 784A, 784B. Further, it should be understood that any description of actuators, servos, motors, articulating arms, control circuitry, and the like with respect to the automated fixture applies as well to the vision assist systems described herein for positioning and maneuvering light sources and/or optics of the light sources.

The configuration of the automated suture fixture 770B can be relatively small and convenient for use in applications designed to assist in the positioning and manipulation of relatively small devices, such as the prosthetic human implant device 710B. The relatively small size of the system 700B and automated fixture 770B also allows for use in a more compact workspace like those often used for suturing prosthetic heart valve implants, e.g., the small size can fit and be used even on a relatively small desk or table, which allows for more efficient use of building and work areas. In certain embodiments, the individual actuator devices (e.g., the individual servo actuator devices) of the automated suture fixture 770B can comprise brushless potentiostat and/or magnetic encoder devices. In certain embodiments, the actuator devices can be implemented using piezoelectric control with analog voltage signals. In certain embodiments, one or more components of the automated suture fixture 770B can be controlled using pulse width modulation control signals, such as control signals spaced by between 0 to 2 μs, for example. In certain embodiments, multiple motor components (e.g., multiple servo motor components) of the automated suture fixture 770B can share one or more common leads with a multiplex signal, such as a three-lead connection. In some embodiments, the automated suture fixture 770B comprises four or five or more servo motor devices. Devices and fixtures disclosed herein can be remote-controllable or at least partially remote-controllable.

The automated fixture 770B (e.g., automated suture fixture) can further comprise a target holder assembly 771B (e.g., a suture target holder assembly), which can be configured to hold or secure the target device 710B (e.g., suture target, prosthetic human implant device, etc.) that is the subject of the process that the operator is engaged in.

In certain embodiments, the suture assistance system 700B comprises a visualization system 760B. The visualization system 760B can include a camera 761B. In some embodiments, the camera 761B remains in a substantially static configuration during execution of a suturing procedure, wherein the automated fixture 770B articulates the target implant device 710B into desirable focus with the camera 761B during the procedure. In certain embodiments, the visualization system 760B can be configured to manually or automatically articulate and/or focus to a target position to provide a precise image of a target suture position for the operator's benefit. For example, the positioning of the camera 761B can be controlled at least in part by a controller executing a suture process script as described herein. In certain embodiments, the system 700B includes multiple cameras configured to provide multiple-perspective imaging (e.g., a dual-perspective imaging) of the implant device 710B and/or automated fixture 770B, which can help to eliminate or reduce blind spots and/or improve ease of operation. The camera 761B can also be configured to automatically re-focus and/or adjust zoom settings to focus on the target device and/or to maintain locational and dimensional consistency.

The suture assistance system 700B can further comprise a display monitor 750B (or multiple display monitors). The display monitor 750B can work in concert with the camera 761B, vision assist system 780B, and/or automated fixture 770B to present to the operator 705 an image identifying a target position (e.g., a target suture position). This can be done to further improve precision and ease-of-use of the system 700B.

The assist system 700B can represent a multi-access assist system for use in a direct human assist for procedures (e.g., for suturing prosthetic human implants, such as heart valves, for inspection and quality control, and/or for other procedures). In certain embodiments, the automated suture fixture 770B can hold the target device or implant device 710B and articulate the target device or implant device 710B to a desired position underneath the camera 761B, which can be, for example, a high-definition (HD) camera, which can provide further precision in monitoring the procedure (e.g., in the suturing procedure, inspection, or other procedure). The automated fixture 770B can advantageously position the implant device 710B to a desired in-focus position within the depth of field of the camera 761B, e.g., with respect to a point or region on the implant device 710B that is to be sutured according to the suturing process.

Configuring the holder assembly 771B of the automated fixture 770B to hold, secure, articulate, or move the prosthetic human implant device 710B can allow for execution of suturing operations by the operator 705 using one less hand than may be required in systems in which an operator is required to manually hold the implant device in the desired suturing position. The free hand of the operator 705 may be available to perform various operations not available in procedures in which both hands of the operator are required for handling and suturing the implant device. For example, a free hand of the operator 705 may be used to adjust cloth being sutured, reposition suturing threads, assist with tying knots, push or pull the needle, and/or the like. Further, allowing the free hand to rest may beneficially reduce the possibility of pain for an operator.

The automated suture fixture 770B can be configured to align the target or implant device 710B so that a targeted area is within a focus of the camera 761B without the need for the operator 705 to determine and execute the appropriate positioning. This can be done to provide a view of the target or a portion of the target (e.g., a desired suture point) on the display 750B. In some embodiments, the visualization system 760B may further be configured to align the camera 761B with the plane of operation presented by the automated fixture 770B.

In certain embodiments, a distal articulation arm 778B of the automated suture fixture 770B can generally present a downward-angled position to allow for proper positioning of the implant device 710B with respect to the position of the operator 705, as shown in FIG. 7B. Furthermore, the camera 761B can advantageously provide an at least partial side angle of the implant device 710B, which can provide a good working view of the target suture position with respect to the operator 705 orientation shown. With the automated suture fixture 770B configured to position the implant device 710B substantially within the depth of field of the camera 761B, it may not be necessary for the camera 761B to adjust focus from one step of the suturing procedure or other procedure to the next.

The suture assistance system 700B can be configured such that the articulation arm 778B of the automated suture fixture 770B can be manually or electronically altered by the operator 705 to train the automated fixture 770B to a custom position, e.g., to record or program position information so the system or automated fixture 770B can return to that position automatically during a procedure. For example, the operator 705 may manipulate the articulation arm 778B to provide accessibility to as much of the target or valve 7108 as possible vis-à-vis the desired work position or posture of the operator 705. The articulation arm 778B may be mechanically moved into the desired position and frozen or held in that position, wherein in the held position, a data capture is executed representing the position of the arm 778B, such that the position can be re-created at a future time in connection with a similar operation or procedure. The position information (e.g., information representative of a position or that can be used to cause the automated fixture and/or articulation arm to move to a particular position) can be saved as part of a procedure script (e.g., a suturing procedure script, inspection script, etc.). For example, since a procedure for suturing and/or a procedure for inspecting the implant device 710B can, and generally will, involve multiple different positions of the implant device 710B, the system 700B can be configured to store a data script comprising information relating to each step and/or position of the procedure, such that the specific positions or steps may be replayed at a later time in connection with the procedure (e.g., an implant suturing and/or inspection procedure associated with the implant device 710B). In this way, an operator can create a personalized or customized procedure script. Similarly, an operator can create a procedure script for a product (e.g., a valve) that can be repeated for that same kind of product and/or for products with a similar sequence of steps to be performed and/or similar dimensions. Advantageously, this provides an easy-to-use programming interface that does not rely on a computer model of the product for positional accuracy. In some embodiments, a three-dimensional model of a product can be loaded into the vision assist system 780B and can be used to program a procedure (e.g., without needing to physically manipulate any component of the automated system).

Figure 8:
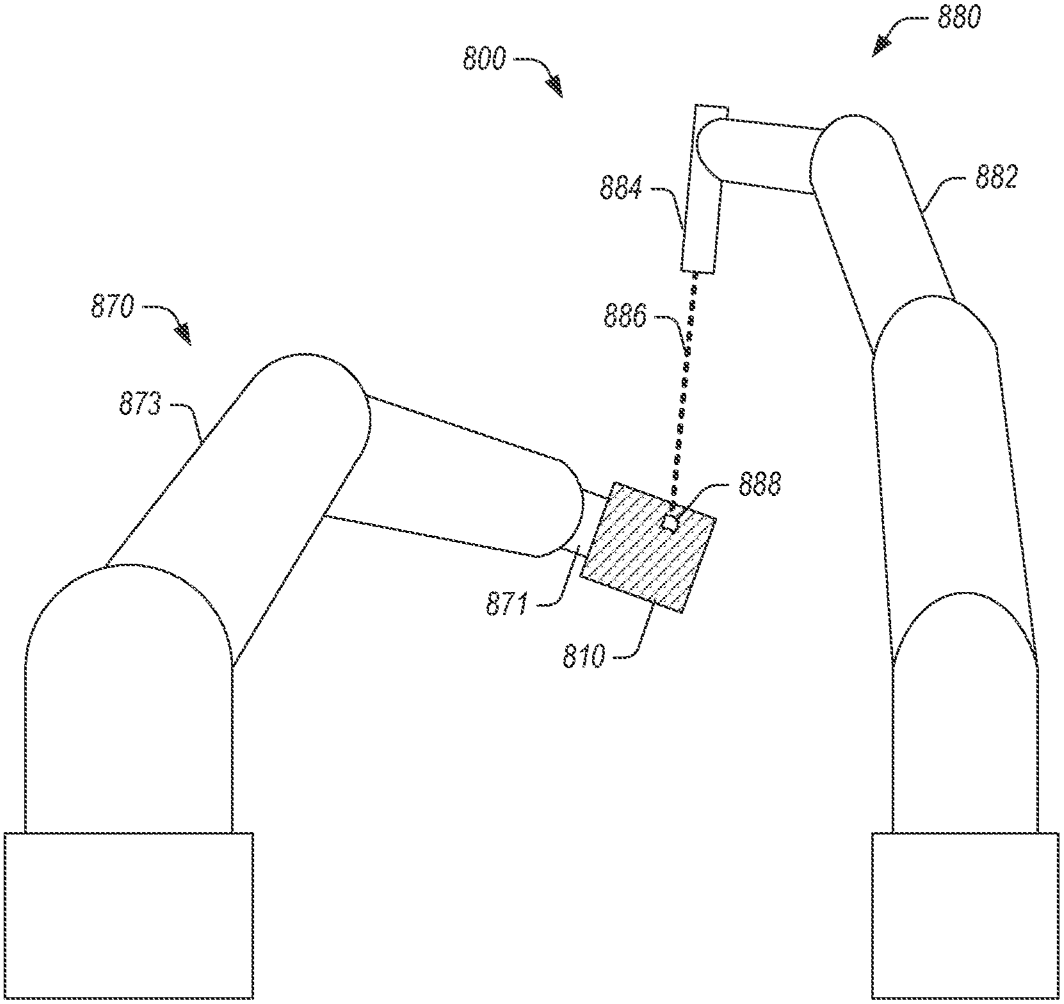
FIG. 8 illustrates an example suture assistance system with an automated fixture and a vision assist system.

FIG. 8 illustrates an example embodiment of an inspection assistance system 800 that includes a vision assist system 880 and an automated fixture 870. In some embodiments, the inspection assistance system 800 can be used as a suture assistance system, examples of which are described herein. The automated fixture 870 includes an articulating arm 873 (e.g., a movable arm including one or more actuators) with a target holder 871 secured to a distal end of the articulating arm 873. The target holder 871 is configured to secure and to position and orient a target device 810. The vision assist system 880 also includes an articulating arm 882 (e.g., a movable arm including one or more actuators) with a light source 884 secured at a distal end of the articulating arm 882.

The vision assist system 880 is configured to position and orient the light source 884 to project light 886 onto a surface of the target device 810 to produce a visual indicator 888. As described herein, the visual indicator 888 can be used to aid an operator in performing a step in a manufacturing or inspection procedure. The articulating arm 882 can be configured to adjust the position of the light source 884 to achieve projecting the visual indicator 888 at a targeted location on the target device 810. Moreover, the articulating arm 882 can be configured to adjust the position of the light source 884 so that the vision assist system 880 does not interfere with the operator in performing the procedure on the target device 810.

The automated fixture 870 is configured to position and orient the target device 810 based at least in part on scripted data for a procedure. The vision assist system 880 coordinates with the automated fixture 870 to produce the visual indicator 888 at the targeted location. As described herein, a three-dimensional model (e.g., a CAD model) of the target device 810 can be used to map the locations of relevant points on the target device 810 so that the vision assist system 880 can determine where to aim the light source 884 to produce the visual indicator 888 at the desired or targeted location. The three-dimensional model can be used to determine a shape, geometry, and/or surface topography of the target device 810. For example, the automated fixture 870 positions and orients the target device 810 with a first position and orientation based on a first step in a procedure. Information about the position and orientation of the automated fixture 870 (e.g., the articulating arm 873 and the target holder 871) is combined with the three-dimensional model of the target device 810 to determine a map of the surfaces of the target device 810 in space. Using this information, the vision assist system 880 determines a suitable position and orientation of the light source 884 (e.g., using ray tracing or other similar algorithms) wherein the light source 884 is able to project light 886 onto a targeted location on the target device 810 to achieve the desired visual indicator 888. In some embodiments, the position and orientation of the light source 884 is further configured to reduce or eliminate the possibility of the operator being impeded by the light source 884 and/or articulating arm 882 while maintaining the ability to provide the visual indicator 888 at the targeted location.

The automated fixture 870 can include a target holder 871 (although called a target holder or assembly herein, this can be another type of target holder device or assembly to hold target devices or components for other procedures). The target holder 871 can be physically coupled to one of the actuators 873, such as to a distal extension arm actuator device of the plurality of actuators 873. The target holder 871 can be configured to hold or have mounted thereto a prosthetic heart valve device, or other prosthetic human implant device, which is desired to be sutured. The target holder 871 can have any suitable or desirable shape, configuration and/or dimensions and can be configured to hold or otherwise secure a target device or implant device in a variety of different ways. Example embodiments of suture target holder devices and assemblies are described in detail below in connection with FIGS. 12, 13, 15 and 31. However, it should be understood that such embodiments are provided as examples only, and other types of suture target holders can be implemented in the system 800. In certain embodiments, the distal actuator includes a rotating support member configured to rotate about a first rotational axis. In some embodiments, the target holder 871 is coupled to the support member of the distal motorized actuator and is configured to rotate about an axis that is parallel to the first rotational axis of the support member. In some embodiments, the target holder 871 is coupled to the support member of the distal actuator and configured to rotate about an axis that is orthogonal to the first rotational axis of the support member.

In some embodiments, the automated fixture 870 is configured to maneuver the target device 810 so that the vision assist system 880 does not need to move between steps of a procedure. In other words, the light source 884 can be maintained in a particular position and orientation while providing the visual indicator 888 at a new targeted location due at least in part to the automated fixture 870 re-positioning the target device 810 such that the visual indicator 888 is projected to the new desired location.

Figure 9:
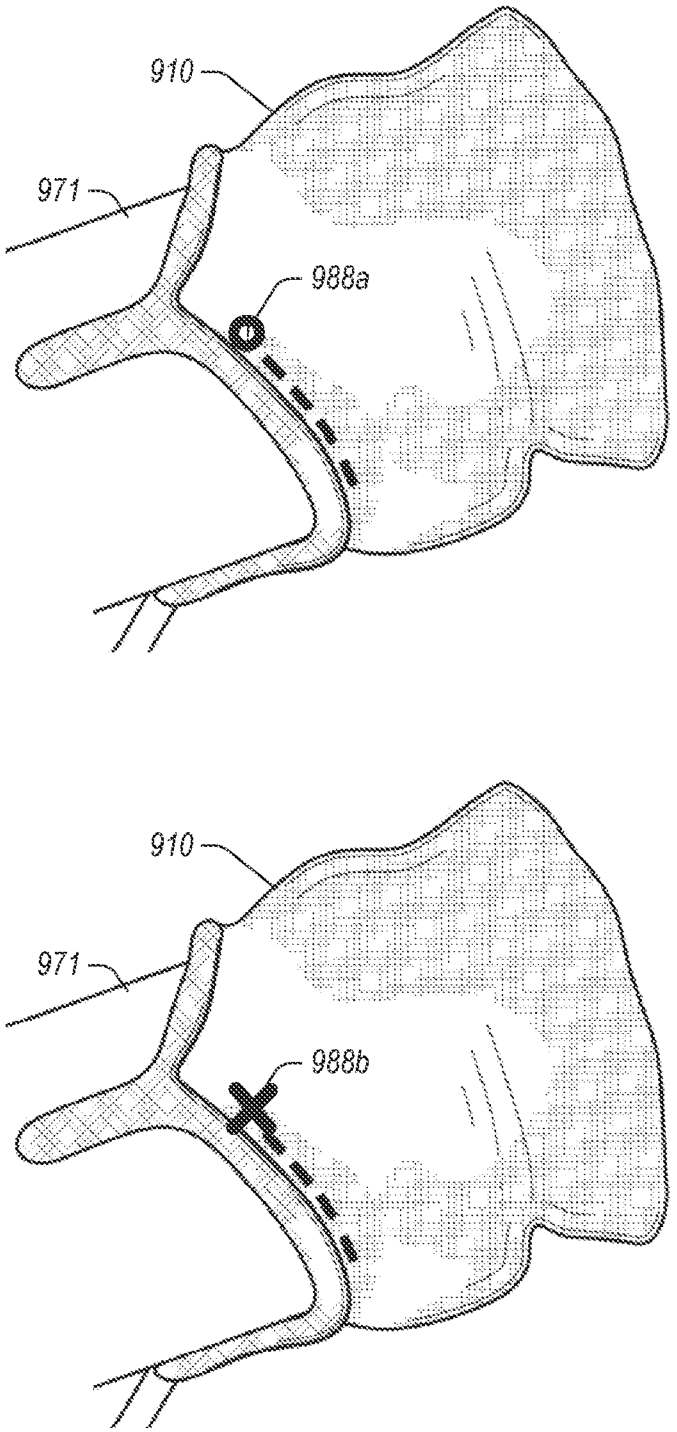
FIG. 9 illustrates examples of a visual indicator produced by a vision assist system.

FIG. 9 illustrates an example of visual indicators 988*a*, 988*b* projected onto a target device 910 secured by a target holder 971. The visual indicators 988*a*, 988*b* can change appearance or properties to convey information to an operator. For example, the top illustration shows the visual indicator 988*a* as a circle which may be used to indicate a correct stitch, an entrance location for a needle, a specific stitch type, or the like, whereas the bottom illustration shows the visual indicator 988*b* as an 'X' which may be used to indicate an incorrect stitch, an exit location for a needle, a specific stitch type, or the like. Other properties of the visual indicator 988*a*, 988*b* may also or alternatively be changed such as, for example and without limitation, color, brightness, size, pattern, persistence, intensity, focus, or any combination of these or the like.

The visual indicator 988*a*, 988*b* can be produced by projecting or directing light from a light source that is outside the target device 910 or by projecting or directing light from a light source that is inside the target device 910 (e.g., backlighting the target device 910). In some embodiments, the visual indicator 988*a*, 988*b* can be animated or to move in a specific pattern to convey information to the operator. The visual indicator 988*a*, 988*b* can be used to direct the operator's attention to a targeted location on the target device 910 for the purpose of forming a stitch on the target device 910, for inspecting a stitch on the target device 910, or the like.

Figure 10A:
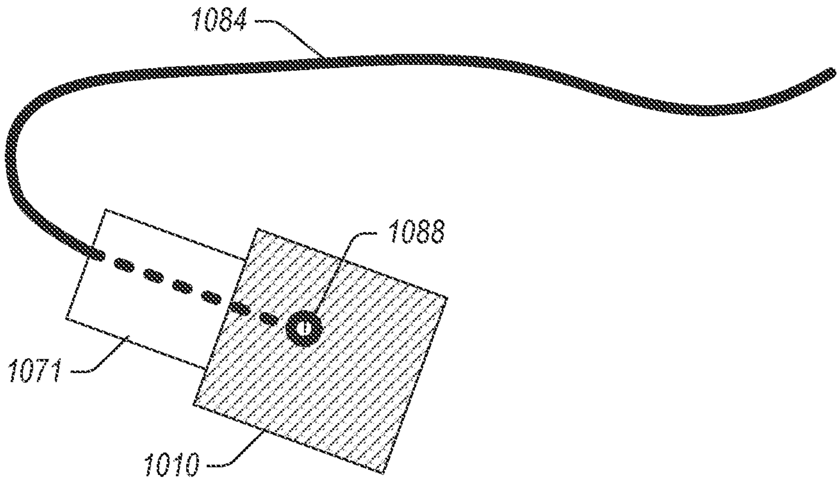
FIGS. 10A and 10B illustrate another example vision assist system using optical fibers to backlight a target device.
Figure 10B:
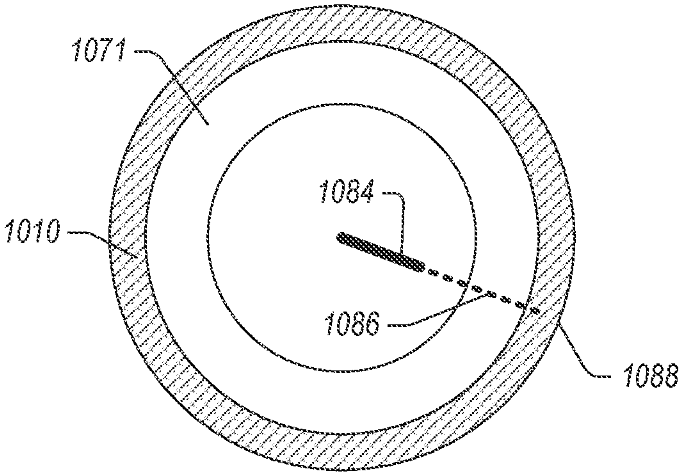

FIGS. 10A and 10B illustrate an example of a vision assist system having an optical fiber 1084 as the light source. In this example system, the optical fiber 1084 is associated with a target holder 1071 so that the optical fiber 1084 is positioned within a target device 1010 to generate a visual indicator 1088 by backlighting the target device 1010. In such embodiments, the actuators of the vision assist system can coincide, at least partially, with the actuators of the automated fixture. In other words, actuators of the automated fixture can also be used to maneuver the light source of the vision assist system.

The optical fiber 1084 passes through a lumen formed by the target holder 1071 so that a light-emitting end of the optical fiber 1084 is surrounded by the target device 1010 when the target device 1010 is attached to the target holder 1071. The optical fiber 1084 can be held by one or more components of the target holder 1071. The optical fiber 1084 can also be moved (e.g., rotated, angled, etc.) by components associated with the target holder 1071 to produce a visual indicator 1088 using light 1086 emerging from a light-emitting end of the optical fiber 1084. The optical fiber 1084 can receive light from a source of light at a light-receiving end (not shown) of the optical fiber 1084. The source of light can be a laser, LED, laser diode, lamp, etc. In certain embodiments, the source of light is physically separate from the automated fixture. In various embodiments, the source of light and/or the light-receiving end of the optical fiber 1084 are fixed. In such embodiments, the source of light and/or the light-receiving end of the optical fiber 1084 do not necessarily move with movement of the light-emitting end of the optical fiber 1084. In some embodiments, the target holder 1071 includes actuators to move and orient the light-emitting end of the optical fiber to produce the visual indicator 1088 at a targeted location.

The illustrated embodiment advantageously reduces the number of articulating arms. In addition, the illustrated embodiment advantageously can use the target holder 1071 to secure the light source 1084 to backlight the target device 1010, reducing the chances that the operator is impeded by the light source 1084.

Example Automated Suture Fixtures

Figure 11:
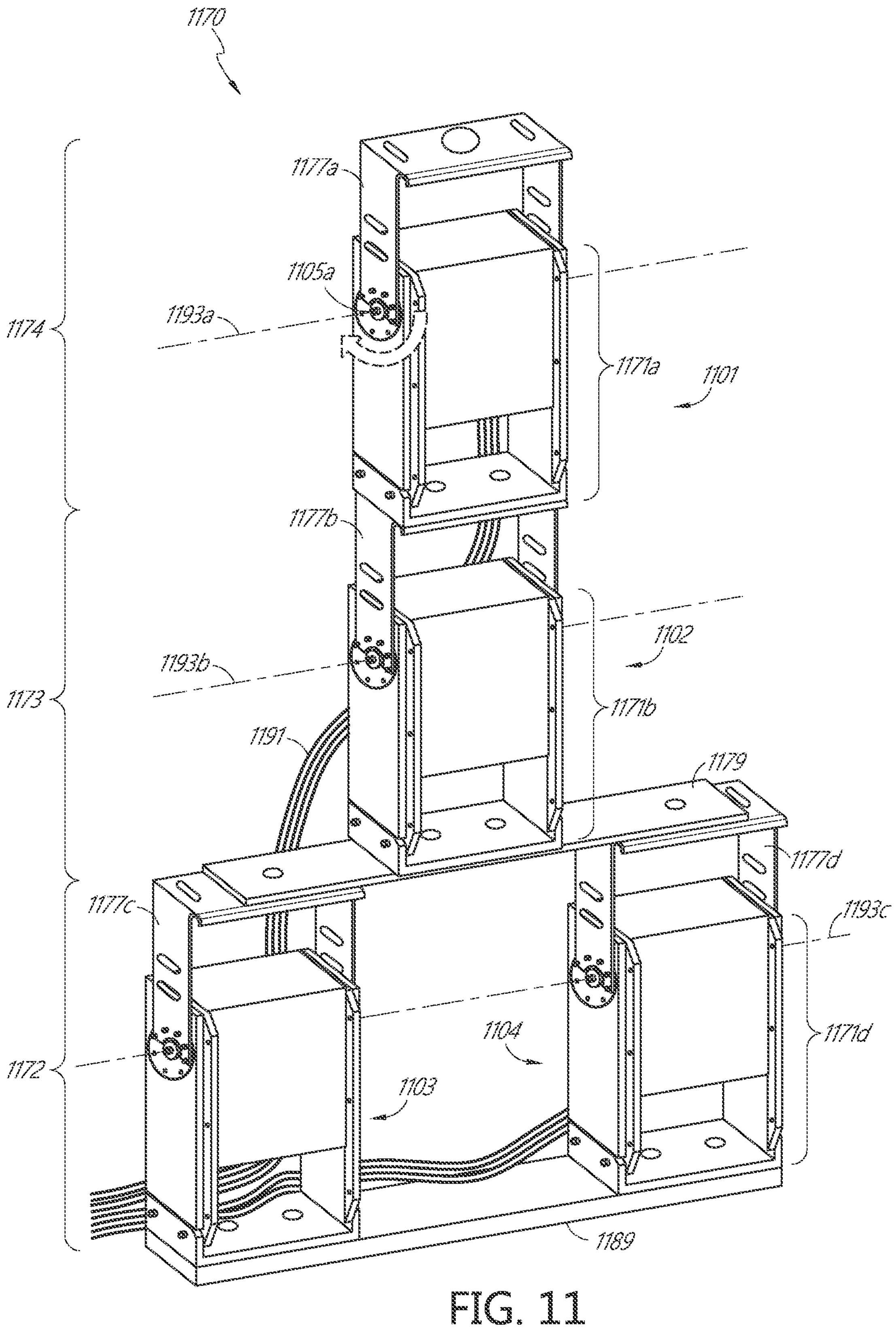
FIG. 11 illustrates a perspective view of an automated suture fixture in accordance with one or more embodiments.

FIG. 11 illustrates a perspective view of an exemplary embodiment of an automated suture fixture 1170 in accordance with one or more embodiments. The automated suture fixture 1170 includes a plurality of motorized actuators 1101, 1102, 1103, and 1104. The motorized actuators 1101-1104 can be physically and/or communicatively coupled in a desired configuration to provide a targeted range of motion and positioning for a distal actuator 1101 (referred to herein in certain contexts as a distal articulation arm) suitable for presenting a suturing target device to an operator in accordance with embodiments of the present disclosure. While four motorized actuators are shown (i.e., 1101-1104), additional motorized actuators and/or other actuators could be used to provide more degrees/types of movement and/or different types of movement (e.g., linear movement, movement in other patterns, etc.). FIGS. 18-25 and 28-30 illustrate exemplary configurations of automated fixtures that include different arrangements of motorized actuators. The automated fixtures described herein with reference to these figures can move up and down to different heights and articulate in additional directions, including horizontal directions.

Figure 12:
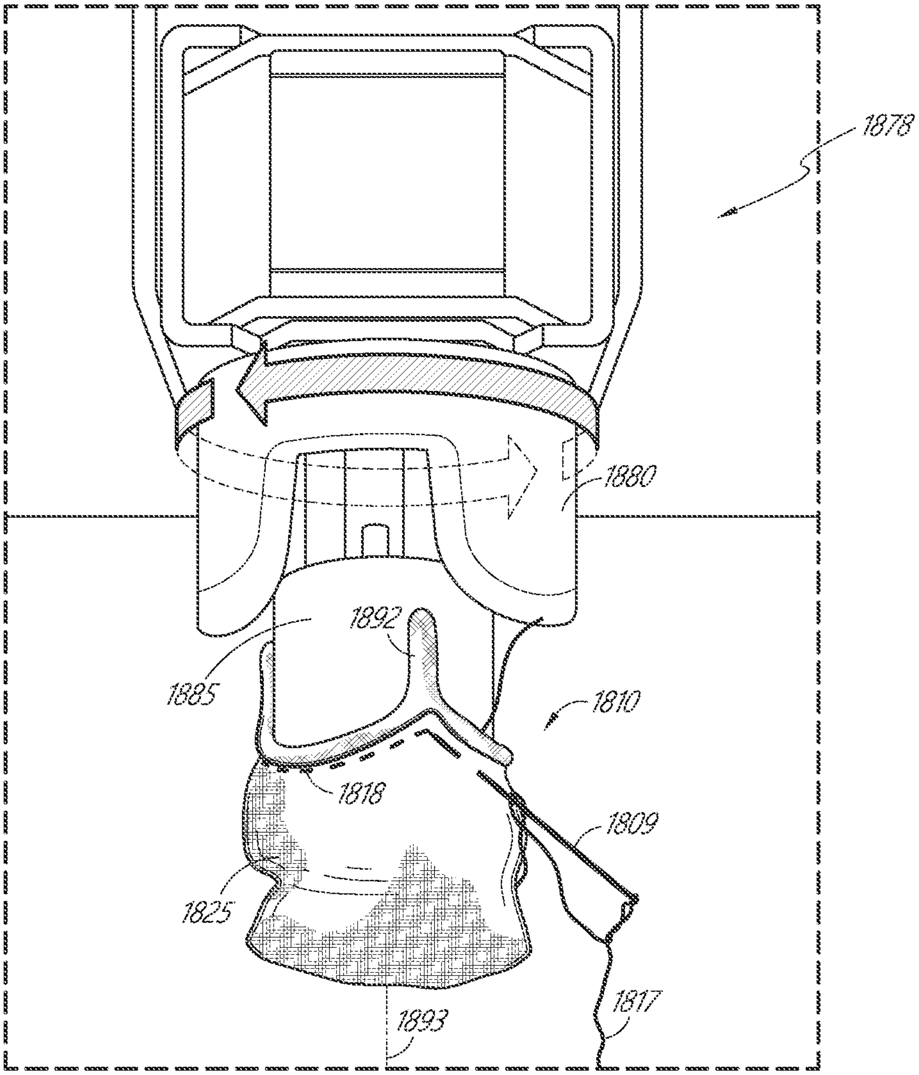
FIG. 12 illustrates a distal articulation arm of an automated suture fixture coupled to a holder component in accordance with one or more embodiments.
Figure 13:
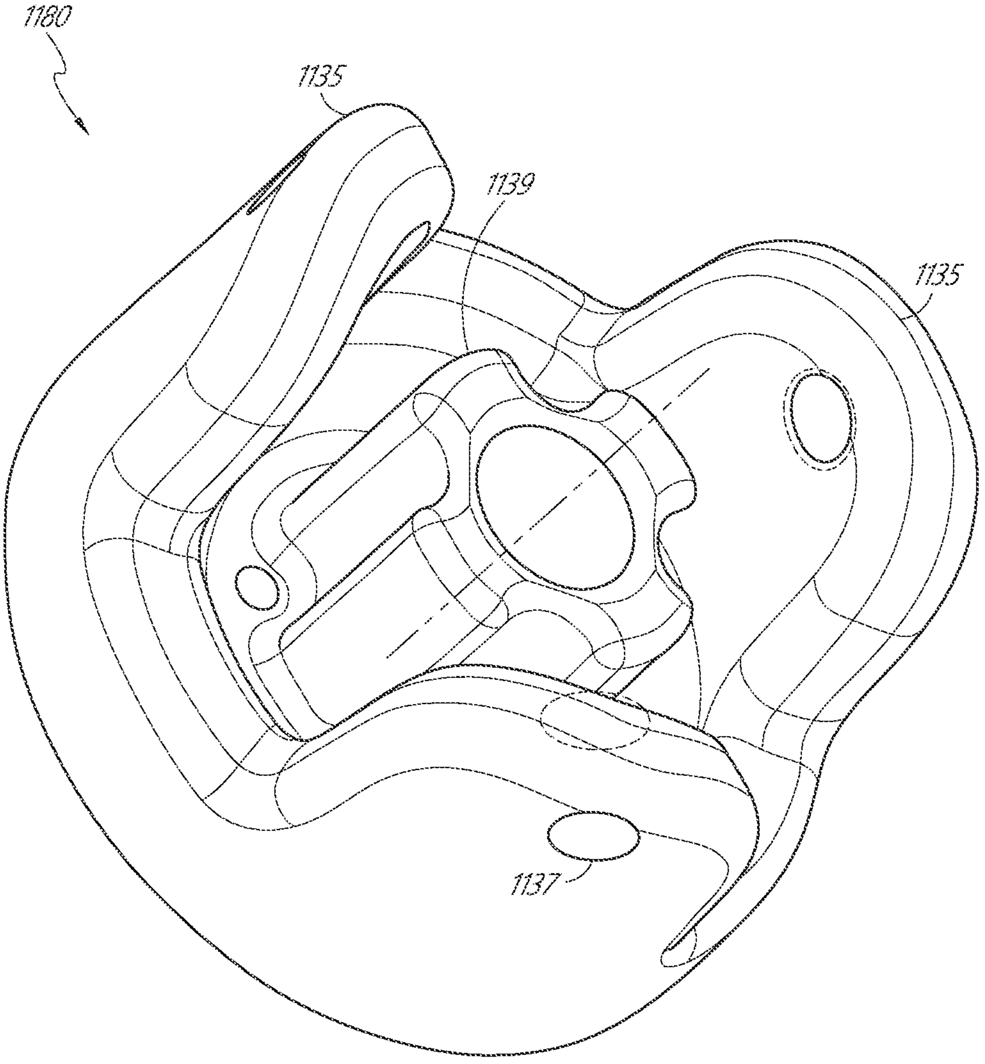
FIG. 13 illustrates a holder device in accordance with one or more embodiments.
Figure 15:
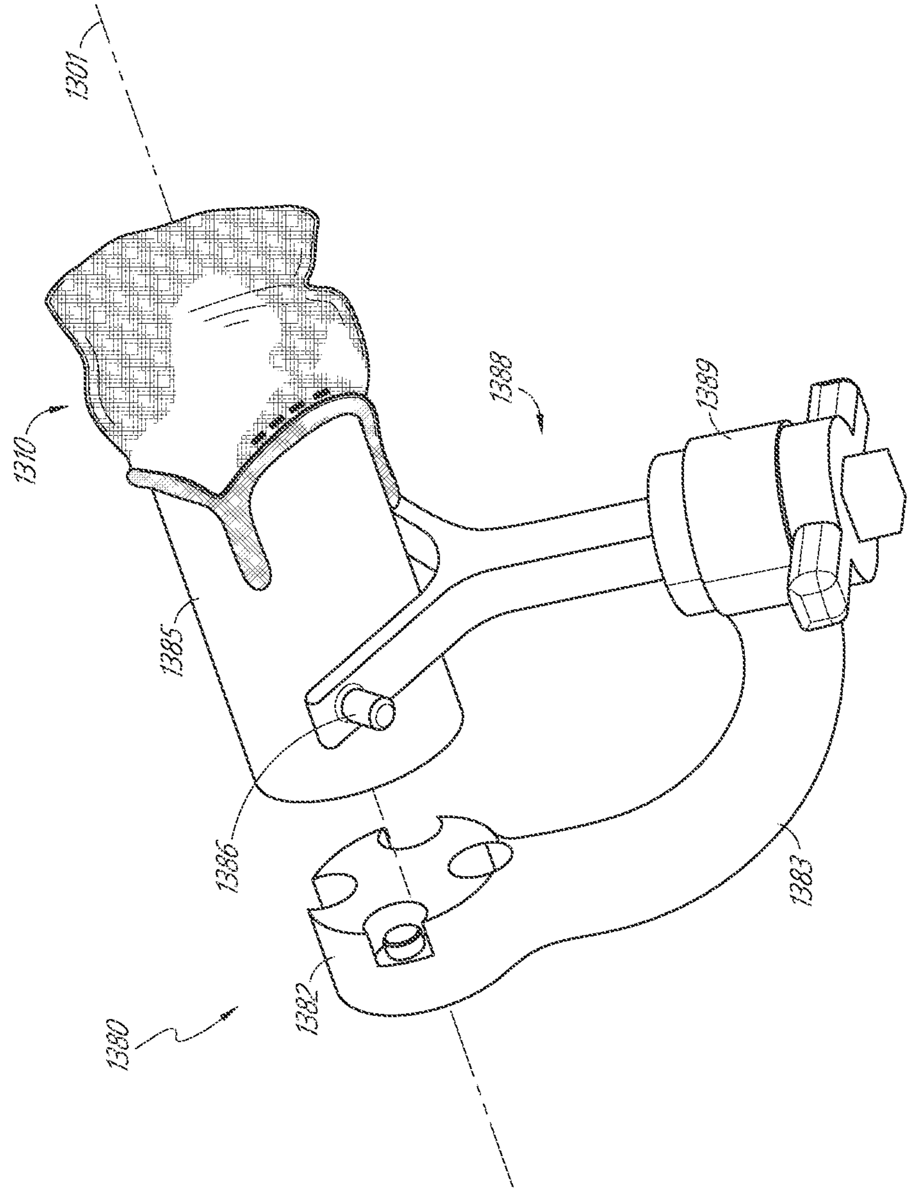
FIG. 15 illustrates a gimbal-type holder assembly in accordance with one or more embodiments.

An end or distal actuator can hold or comprise (or be modified to hold or comprise) a holder device or assembly (e.g., a holder device or assembly described herein with reference to FIGS. 12, 13, 15, and/or 18-31) and/or target device (e.g., valve). For example, the automated fixture shown in FIGS. 18-25 and 28-30 (and other automated fixtures described or shown herein) can be modified to include, at an end thereof, the holder assembly/device shown in FIGS. 26, 27 and/or 31. In some embodiments, bags can be configured to at least partially cover linkages from ingress.

With reference to FIG. 11, each of the motorized actuators 1101-1104 can comprise a base portion 1171 and a rotating support member 1177 mechanically fixed to a rotor component 1105. In certain embodiments, the rotor component 1105 is associated with a magnetic motor (not shown), wherein rotation of the rotor component 1105 is caused by the interaction between conductive windings and magnetic fields designed to produce a torque around the rotor's axis (e.g., 1193*a*, 1193*b*, 1193*c*, respectively). The motor can utilize a set of gears to rotate the output rotor and a potentiometer at the same time. The potentiometer, which can at least partially control the angle of the servo motor, can allow the control circuitry (not shown) to monitor the current angle of the servo motor. The motor, through a series of gears, can be configured to turn the output rotor and the potentiometer simultaneously. The potentiometer feedback signal can be fed into the servo control circuit, wherein when the control circuit detects that the position is correct, it stops the servo motor. If the control circuit detects that the angle is not correct, it can continue to turn the servo motor the correct direction until the angle is correct. While rotating actuators are described, actuators that move linearly can also be used (e.g., to raise and lower or move in and out a portion of the fixture).

In certain embodiments, the automated suture fixture 1170 includes a plurality of stages. For example, as shown, the fixture 1170 can comprise a base stage 1172 that includes motorized actuators 1103, 1104. In the illustrated embodiment, the base stage 1172 includes two separate actuators (1103, 1104) that provide base support for the fixture 1170 but it is to be understood that the number of motorized actuators can be any suitable number such as one, two, three, four, five, or more than five. In some embodiments, the actuators 1103, 1104 of the base stage 1172 can be secured mechanically to one another in any suitable or desirable way. For example, as shown, the actuators 1103, 1104 can each be mounted to a common reference structure, such as an attachment plate 1189, or other structure. Each of the actuators 1103, 1104 can comprise a rotating support member (1177*c*, 1177*d*) configured to rotate about a common rotational axis 1193*c*, as shown.

The automated suture fixture 1170 includes a second stage 1173, which can comprise one or more motorized actuators. For example, as shown, the stage 1173 can comprise a single actuator device 1102 in some embodiments. The base portion 1171*b* of the actuator 1102 can be fixed or secured to one or advantageously both of the rotating support members of the base stage actuators 1103, 1104, as shown. Where the base actuators 1103, 1104, are separated horizontally from one another by a certain distance, it may be desirable to use a support plate or structure 1179 for fixing the support members of the base stage actuators 1103, 1104 to one another, wherein the second stage actuator 1102 is fixed to the support plate 1179. That is, the support plate 1179 can be secured or fixed, such as through the use of one or more bolts, screws, nuts, and/or the like, to both of the support members of the base stage 1172, and further secured or fixed to the base of the second-stage actuator 1102 through any suitable or desirable means.

The second-stage actuator 1102 may further comprise a rotating support member 1177*b* configured to rotate about the rotor axis 1193*b*. Therefore, the second stage actuator 1102 can provide an additional degree of movement of the automated suture fixture 1170 when combined with the base-stage actuators in the attachment configuration illustrated. The automated suture fixture 1170 can yet provide an additional degree of movement through implementation of the distal actuator 1101 illustrated. Although a third stage 1174 is shown in the diagram of FIG. 11, it should be understood that in certain embodiments the fixture 1170 can include only the base stage 1172 and the second stage 1173. Furthermore, although the illustrated embodiment comprises three stages, it should be understood that embodiments disclosed herein can be implemented using automated suture fixture assemblies having more than three stages (e.g., 4, 5, 6, 7, 8 or more stages) and/or having more than four motorized actuator devices (e.g., 5, 6, 7, 8, 9, or more actuator devices).

The distal third-stage actuator 1101 can be fixed or secured at a base 1171*a* thereof to the rotating support member 1177*b* of the second-stage actuator 1102, as shown. Furthermore, the distal actuator 1101 can further comprise a rotating support member 1177*a*, which can be configured to rotate to provide yet another degree of movement for the fixture 1170. In certain embodiments, the distal actuator 1101 can have attached thereto (e.g., at the rotating support member 1177*a*) a suture target holder assembly or target holder assembly in accordance with embodiments of the present disclosure.

The automated fixture 1170 is illustrated in the diagram of FIG. 11 in a substantially erect arrangement, in which the respective support members are positioned in a vertical arrangement, such that the rotational axes of the respective actuator devices lie substantially in a single vertical plane. However, the additional degrees of movement provided by the fixture 1170 may allow for rotation of the various support members, such that the axes of rotation of the respective rotors of the second- and third-stage actuator devices may ultimately lie in separate vertical planes from the rotational axis of the support members 1177*c*, 1177*d* of the base-stage actuator devices 1103, 1104.

The various motorized actuator devices of the automated suture fixture 1170 can be controlled in any suitable or desirable way. For example, in some embodiments, the various motorized actuator devices of the fixture 1170 can be configured to receive wireless control signals over a wireless connection with a control system, device or module, such as the controller 730A of FIG. 7A described herein, or the like. In some embodiments, the actuators can be configured to receive wired control signals, such as over the various wired connections 1191 illustrated. For example, certain embodiments, two or more of the stages and/or actuator devices of the fixture 1170 can be communicatively coupled using a wired connection in a daisy-chain configuration, as described herein.

FIGS. 18-25 illustrate an exemplary automated suture fixture 1970. The automated suture fixture 1970 includes an articulating arm 1978 having a plurality of actuator devices 1973A-1973D daisy chained together to provide movement of a distal target mount point 1971. The distal target mount point 1971 can be configured to secure a suture target holder device or assembly such as those illustrated in FIGS. 26, 27, and 31. The suture target holder can be physically coupled to the distal target mount point 1971 or it can be integrally formed as part of the distal target mount point 1971. The suture target holder can be configured to hold or have mounted thereto a prosthetic heart valve device, or other prosthetic human implant device, which is desired to be sutured.

The automated suture fixture 1970 also includes a vertical translation stage 1972 configured to vertically move the articulation arm 1978. This further increases the range of movement of the automated suture fixture 1970 while maintaining a desirably small footprint. The vertical translation stage 1972 can include a piston configuration that attaches to the proximal actuator device 1973A so that the vertical translation stage 1972 can cause the entire articulation arm 1978 to raise and lower. The vertical translation stage 1972 can be configured to not be exactly vertical and can be tilted or angled away from perfectly vertical.

The automated suture fixture 1970 can include a base or base plate 1979 to support the vertical translation stage 1972 and to define a workspace for manufacturing the target device. In certain embodiments, the working zone for the fixture 1970 may be approximately 6.75" high (e.g., the articulation arm 1978 can translate about 6.75" vertically or at least 4" and/or less than or equal to about 10"). In some embodiments, the height of the vertical translation stage 1972, H, is about 26" or at least about 20" and/or less than or equal to about 36", at least about 22" and/or less than or equal to about 30", or at least about 24" and/or less than or equal to about 28". In some embodiments, the depth of the base plate 1979, D, is about 18" or at least about 12" and/or less than or equal to about 24", at least about 14" and/or less than or equal to about 22", or at least about 16" and/or less than or equal to about 20". In some embodiments, the length of the base plate 1979, L, is about 20" or at least about 12" and/or less than or equal to about 30", at least about 15" and/or less than or equal to about 26", or at least about 18" and/or less than or equal to about 24".

With respect to FIGS. 19 and 20, the illustrated positions of the fixture 1970 can correspond to a bottom of a stroke of the vertical translation stage 1972 in a z-direction. In certain embodiments, the distal target mount point 1971 can be configured to tilt approximately 54 degrees upward. With respect to FIGS. 21 and 22, the fixture 1970 can change the position and orientation of the distal target mount point 1971 while at the bottom of the stroke of the vertical translation stage 1972. This can be done by actuating the articulation arm 1978.

With respect to FIGS. 23 and 24, the illustrated positions of the fixture 1970 can correspond to a top of a stroke of the vertical translation stage 1972 in the z-direction. In certain embodiments, the distal target mount point 1971 can be configured to tilt approximately 15 degrees down from horizontal. With respect to FIG. 25, the illustrated position of the fixture may represent an approximately 45-degree downward tilt for implementing a "dipping" step.

Figure 28:
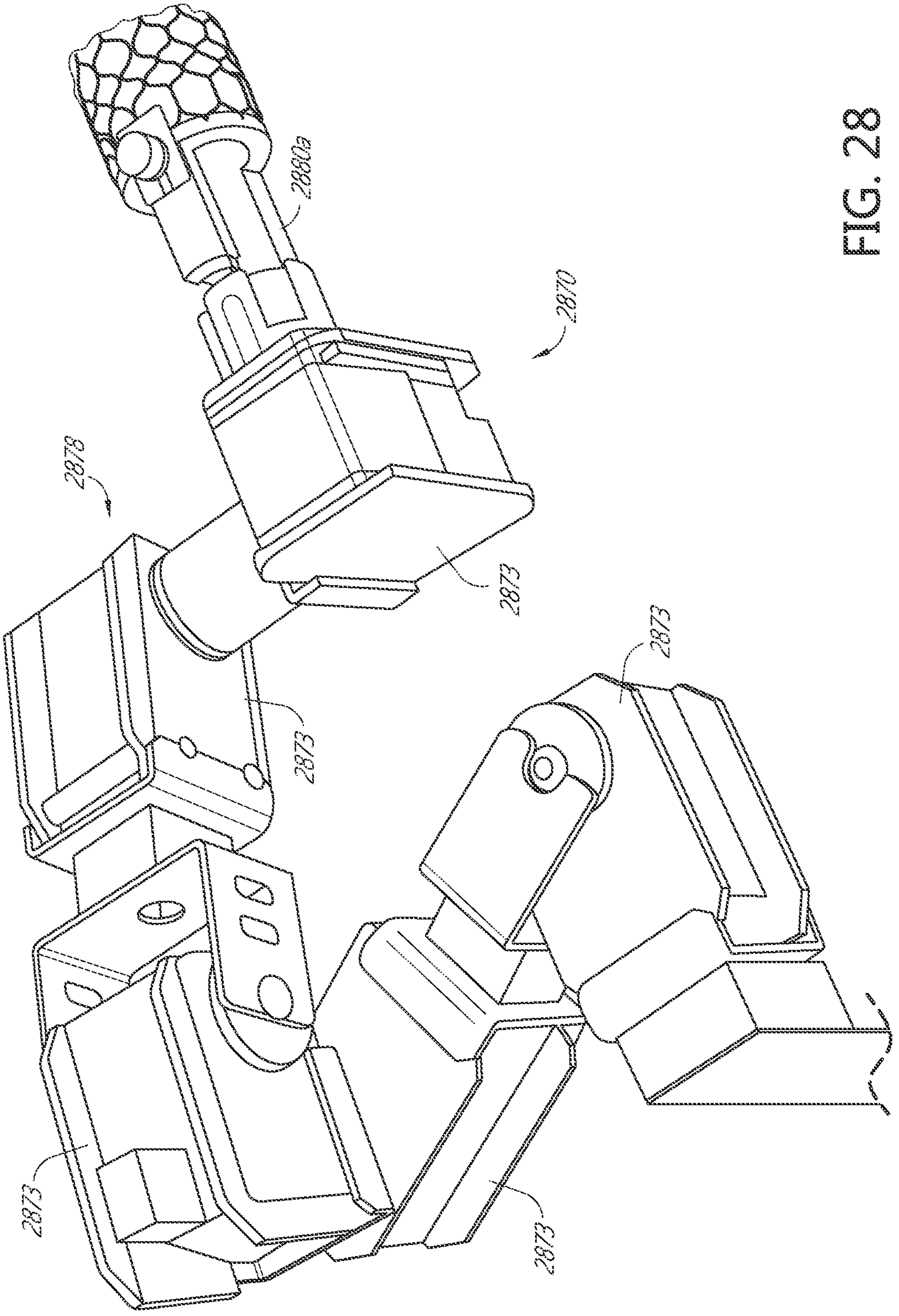
FIGS. 28 and 29 illustrate an exemplary automated suture fixture having a configuration for an articulation arm that includes a plurality of actuator devices that are oriented to provide additional vertical support.
Figure 29:
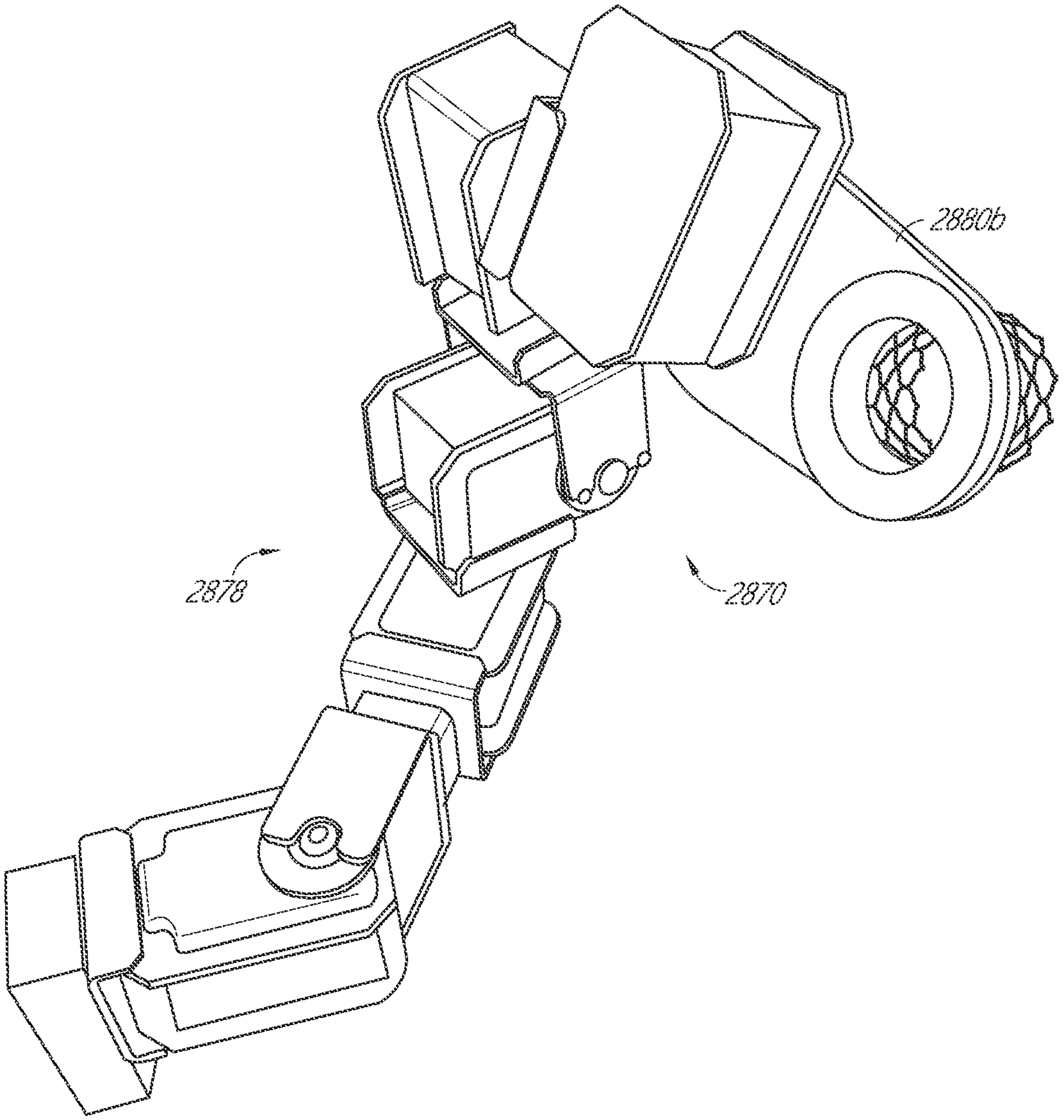

FIGS. 28 and 29 illustrate another example automated suture fixture 2870 having a different configuration for an articulation arm 2878. The fixture 2870 includes a plurality of actuator devices 2873 that are oriented to provide additional vertical support. By orienting rotors so that the axis of rotation is substantially vertical, the support members can provide additional support against downward forces as opposed to relying on the motor to resist downward forces. This may be of increased importance closer to the proximal end of the articulation arm due to the increase in torque the further from the pivot point a force is applied (e.g., a downward force at a distal end of the articulation arm 2878 can cause more torque at the proximal end than at the distal end). The automated suture fixture 2870 can be coupled to different target holders, such as target holders 2880*a* and 2880*b* respectively illustrated in FIGS. 28 and 29. The target holder 2880*a* can be the same as or similar to the target holder 3180 described herein with reference to FIG. 31. The target holder 2880*b* can be geared (e.g., similar to target holder 2680) to allow for rotation of the target holder and/or target without blocking the view of the visualization system. The target holder 2880*b* is also beneficially configured to allow access to the interior of the target from both ends or leave the interior open on both ends so that an operator can insert a finger and/or retrieve a needle from inside at either end of the target.

Figure 30:
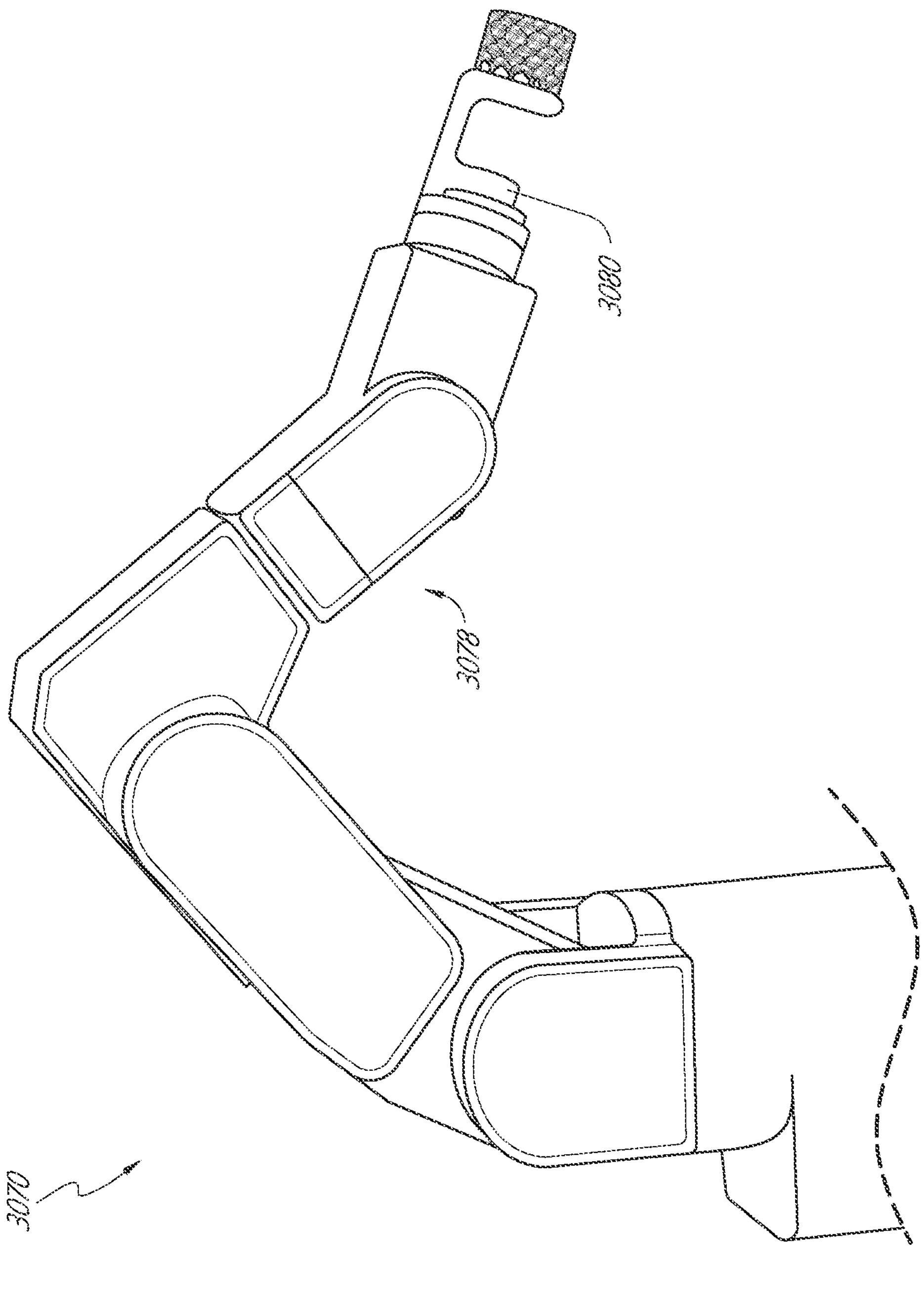
FIG. 30 illustrates an exemplary automated suture fixture having an articulation arm.

FIG. 30 illustrates another example automated suture fixture 3070 having a different configuration for an articulation arm 3078. The articulation arm 3078 has a crane-like configuration and is configured to substantially enclose the actuation devices within a housing or a plurality of housings. The articulation arm 3078 secures a target assembly 3080 that is similar to the target assembly 3180 described herein with reference to FIG. 31.

Example Target Holders

FIG. 12 illustrates an articulation arm 1878 coupled to an exemplary holder component 1880 according to one or more embodiments. The articulation arm 1878 can be the same as or similar to the articulation arms 773, 873 described herein with reference to FIGS. 7A, 7B, and 8 and/or one or more actuators described or shown elsewhere herein. The holder component 1880 can be the same as or similar to other target holder components, devices, or assemblies (e.g., 771, 871, 971, 1071, 1180, 1380, 2680, 2880, 3080, 3180) described elsewhere herein. In certain embodiments, the holder component 1880 can be fixed or secured to the distal articulation arm 1878 or end actuator of an automated suture fixture for the purpose of providing an interface for securing an implant device or other target form or device. The holder component/assembly 1880 can be designed or configured to hold or secure an implant device or other target device, or portion thereof, for the purpose of allowing suturing thereof according to any process or embodiment disclosed herein.

The holder component 1880 can be configured to secure or otherwise include a cylinder form 1885, which can be sized or dimensioned to have pulled thereover the target device or implant (e.g., a fabric-covered support stent for a surgical valve implant device 1818). For example, the valve implant device 1818 may comprise a plurality of commissure post portions 1892, as shown, which may be positioned such that they are oriented in a direction towards the holder component 1880, such that a seam 1818 may be stitched above what will ultimately represent an inflow edge of the implant device 1818. The cylindrical form/component 1885 may be designed in a similar manner to a handheld implant device holder, which may be used in certain embodiments in executing suturing procedures without the assistance of the articulation arm 1878 and associated components. The cloth 1825 can be disposed about a rigid wireframe structure, wherein the seam of stitches 1818 is executed in order to substantially cover the wireframe with the cloth 1825. The seam 1818 can secure the cloth 1825 about a stiffening band, as described herein with reference to FIG. 3A.

The holder component 1880 can be designed for a particular application, such as for a transcatheter heart valve suturing application, or a surgical heart valve suturing operation, or other implant suturing procedure. The valves can be for animal (e.g., for human) use. Although a surgical valve configuration is shown in FIG. 12, it should be understood that the holder device 1880 and/or other components of FIG. 12 may be designed or configured to support suturing processes and/or other processes for a transcatheter heart valve or other valve or other device. For example, while the diagram of FIG. 12 illustrates a cylindrical form 1885 designed to hold the implant device 1818 in a desired position, such cylindrical form may not be necessary with respect to a transcatheter heart valve. For example, in place of the cylindrical form 1885, the holder 1880 can instead be configured to secure a rigid cylindrical wireframe of a transcatheter heart valve, an embodiment of which is illustrated and described above in connection with FIG. 1.

With the target or implant device 1818 secured to the holder device 1880, an operator may conveniently be able to execute stitching operations using, for example, a needle 1809 and thread 1817. For example, the system can facilitate or make it easier for an operator to perform exterior circumferential stitching operations (e.g., with respect to surgical heart valves), interior-to exterior stiches, and/or exterior-to-interior stitches (e.g., for certain transcatheter heart valve stitching operations). The holder device 1880 and/or associated components can be designed to efficiently allow for the target or implant device 1818 be presented to the operator such that multiple degrees of freedom are available for the operator and articulation arm 1878 to further simplify and assist with suturing or other procedures.

In certain embodiments, the holder component 1880 and/or one or more components associated with the holder component 1880 (e.g., the cylinder form, etc.) can be configured to rotate about a central or longitudinal axis 1893 thereof. Central axis 1893 can represent a central axis of the target or implant device 1810, cylinder 1885, and/or other portion of the holder component 1880 (e.g., when the device 1810, cylinder 1885, and/or other component is connected or mounted to the holder component 1880). The rotation of the holder component 1880 and/or components associated therewith may allow for presentation of different surface areas of the target or implant device 1810 to the operator during different stages of a suturing procedure or other procedure.

The specific type of holder that is utilized for a procedure or application (e.g., for a suture assistance application) may be determined on a process-by-process basis. That is, specific adapters may be suitable or desirable for each of separate operations/procedures, or for separate types of valves or other targets. In certain embodiments, a single suturing procedure of an implant device can involve use of multiple different types of holder devices.

FIG. 13 illustrates an exemplary holder component/device 1180 in accordance with one or more embodiments disclosed herein. For example, the holder device 1180 may be the same as or similar in certain respects to the holder device 1880 described herein with reference to FIG. 12 and/or other holder devices, components, assemblies, etc. (e.g., 771, 871, 1380) described elsewhere herein. The holder component 1180 can comprise one or more features or components designed to allow for a cylindrical holder and/or component of a target or implant device to be secured thereto. For example, the holder 1180 may allow for securing of a cylindrical holder and/or component of the implant device in such a manner as to provide radial symmetry for precise positioning thereof. In certain embodiments, the holder 1180 comprises a plurality of jaw or clamp forms 1135, which may be arranged in a radially symmetrical pattern about a circumference of the holder 1180. The jaws 1135 may be configured to be tightened to hold the cylindrical holder and/or target or implant device component, or may comprise one or more other mechanisms for securing the cylindrical holder and/or target or implant device about a central hub component 1139. For example, the jaw forms 1135 may comprise one or more apertures for utilizing set screws therein, which may be configured to grip or secure the cylindrical holder and/or target or implant device component.

Certain embodiments disclosed herein provide for holding and/or positioning of an implant device that is the subject of a suturing procedure using a gimbal-type holder assembly 1380, as shown in FIG. 15. Further, the automated fixture, articulation arm, and/or various actuators of the automated fixture can also or alternatively be configured to function similar to a gimbal. While certain embodiments of implant device holder components as disclosed herein may generally present one end of the implant device and/or circumferential surfaces or features of the device to the operator, certain of such embodiments may not allow for free operation by the operator about both front and back ends of the implant device and/or holder device. For example, one end of the implant or holder device may be secured at least in part to a component of an articulation arm and/or other holder device. The valve holder device of FIG. 15 and/or other portions of the automated fixture can provide a mount that allows for operational access at multiple ends of an implant device, and may essentially be configurable to float or rotate to the proper position for manufacturing, thereby relieving the operator of the burden of removing the implant device from the holder and rotating and re-securing the implant device in order to have access to both ends of the implant device during a suturing procedure or other procedure.

The gimbal assembly 1380 and/or other gimbal-like arrangements of an automated fixture can be configured to articulate a heart valve or other target or implant device to substantially any desired orientation for ease of access and use for an operator. For example, the gimbal assembly 1380 can comprise a three-axis gimbal allowing for three degrees of freedom. Furthermore, where the gimbal assembly 1380 is mounted to an articulation arm and/or device, additional degrees of freedom may be provided. For example, the combination of the gimbal assembly 1380 with the associated automated suture fixture can provide six degrees of freedom of manipulation. In certain embodiments, the gimbal assembly 1380 may be a two-axis gimbal.

When having secured thereto a target or implant device, such as a transcatheter heart valve or surgical valve implant device, the gimbal assembly 1380 and/or other gimbal-like arrangement of an automated fixture can be configured to position the target or implant device accurately in multiple orientations. For example, the gimbal assembly 1380 can be configured to execute circumferential rotation of a heart valve, while maintaining the outer surface (or a desired portion of the outer surface) of the target or implant device or valve within a focal plane or depth of field of an associated camera and/or magnification system.

The gimbal assembly 1380 includes a cylindrical implant holder 1385 having disposed thereon a surgical implant device 1310, which may represent a suturing target implant in accordance with certain embodiments. However, although a cylindrical implant holding form 1385 is illustrated in FIG. 15, it should be understood that, in certain embodiments, the gimbal assembly 1380 may not include the cylindrical implant holding form 1385, and can instead be configured to hold a different holder component (e.g., a rigid cylindrical or otherwise-shaped component) or to directly hold a heart valve or other target or implant device or portion thereof, such as a cylindrical wireframe of a transcatheter heart valve as described herein. A different holder component or target or implant device could be held where the cylindrical holder 1385 is shown. For purposes of discussion, the illustrated component or cylinder 1385 may be referred to below as a holder component and/or as the target or implant device (or valve) itself, indicating that the target or implant device to be sutured, or otherwise engaged, can be disposed and/or secured in the same position shown by the disposition of the cylinder 1385 in FIG. 15. Descriptions of the component 1385 apply to any holder or target device held in the position of component 1385, regardless of whether it is referred to as a component, device, holder, valve, etc. in the description.

Rotation of the target or implant device or valve 1385 may be implemented by rotating a hub component 1382, which can be attached or associated with a rotating servo head of an articulation arm or actuator (not shown in FIG. 15), wherein the hub component 1382 can be associated with an arm component 1383 that allows for rotation of the target or implant device or valve 1385 about a central or rotational axis 1301 of the hub component 1382 and the target or implant device 1385. That is, where the target or implant device or valve 1385 is connected to the arm 1383 via a connector form 1388, such as a Y-connector form, it may be desirable for the connector form 1388 to be adjusted such that the central or longitudinal axis of the target or implant device is aligned or substantially aligned with the rotational axis 1301 of the hub component 1382. When the target or implant device 1385 and the hub component 1382 are thus aligned, rotation of the hub component may be possible while maintaining coaxial alignment of the target or implant device 1385 with the hub 1382, thereby allowing for consistent presentation of an outer surface or region of the target or implant device 1385 in the depth of field of the associated visualization system (e.g., camera). Therefore, the target or implant device 1385 can be circumferentially rotated without moving the target or implant device, or target suture position thereof, out of focus of the camera system.

The connector form or Y-connector 1388 can be configured to nest in a base portion of the arm 1383 and can further be adjustable and provide an indexing feature to allow for movement in and out of the base component 1389 to thereby allow for precise positioning of the target or implant device 1385. In certain embodiments, the hub component 1382 may be coupled magnetically with an associated articulation arm or actuator of an automated fixture. Optionally, the connector form or Y-connector can be rotatable within the base component 1389 to provide for more degrees of movement and positioning possibilities (e.g., to allow the target device to be flipped toward or away from the hub component 1382 and/or rotated to any angle with respect to the axis 1301. The base component 1389 may include a motor or be a motorized actuator to cause movement or rotate the connector form or Y-connector 1388, e.g., so the system can be programmed or scripted to move automatically to a desired position/rotation for a procedure.

The automated fixtures and/or holders described herein can be configured such that a point (e.g., a centermost point) within a target device can remain fixed/stationary while the target device is rotated or repositioned to expose different portions of the target device for a particular operation/step in a procedure.

While various other multi-axis gimbal devices may not be designed to have manufacturing done to them, the gimbal assembly 1380 shown in FIG. 15 can advantageously provide for precise positioning of the distal end of the connector form or arm 1388 and the target or implant device 1385 in order for manufacturing to be performed thereon. Furthermore, with one or two side points of attachment 1386, multiple degrees of freedom can be presented by the gimbal assembly 1380, thereby providing convenience and ease-of-use for the operator. With the multiple-axis (e.g., three-axis) functionality of the gimbal assembly 1380 or other gimbal arrangement of the automated fixture, the target or implant device can be allowed freedom to move to a wide variety of positions and angles to make it easier for the operator to engage with (e.g., suture, inspect, etc.) the target or implant device or valve and to maneuver fingers or other items at a desired location thereon. The multiple-axis (e.g., three-axis) functionality can also make it easier for an operator to view from one side through to the other side of the target or implant device 1385 without substantial obstruction.

Figure 26:
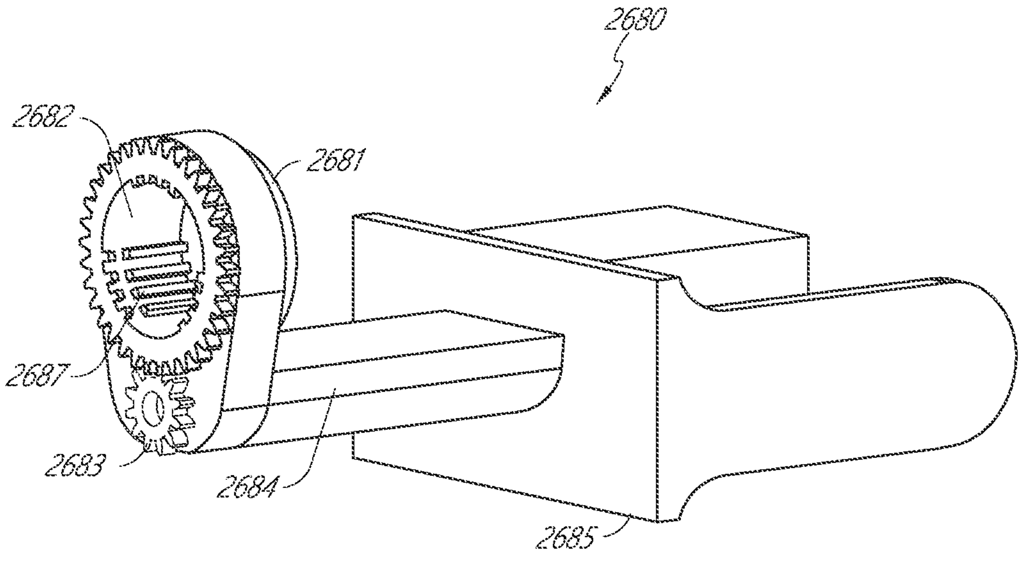
FIG. 26 illustrates a perspective view of a mount or holder device/assembly in accordance with one or more embodiments.

FIG. 26 illustrates an exemplary mount or holder assembly 2680 that can be used with the assist systems, automated fixtures, gimbal assemblies or arrangements, etc. disclosed herein. The holder device 2680 can be attached or connected to another holder and/or to a motorized actuator (e.g., the same as or similar to those discussed or shown elsewhere herein), e.g., at a proximal end, distal end, back end, end opposite the rotating portion or ring, etc. The holder assembly 2680 can comprise a motor and/or motorized actuator (e.g., a rotational motor/motorized actuator). The holder assembly 2680 can include a portion 2681 or mechanism configured to hold and rotate a target device (e.g., heart valve).

Figure 27:
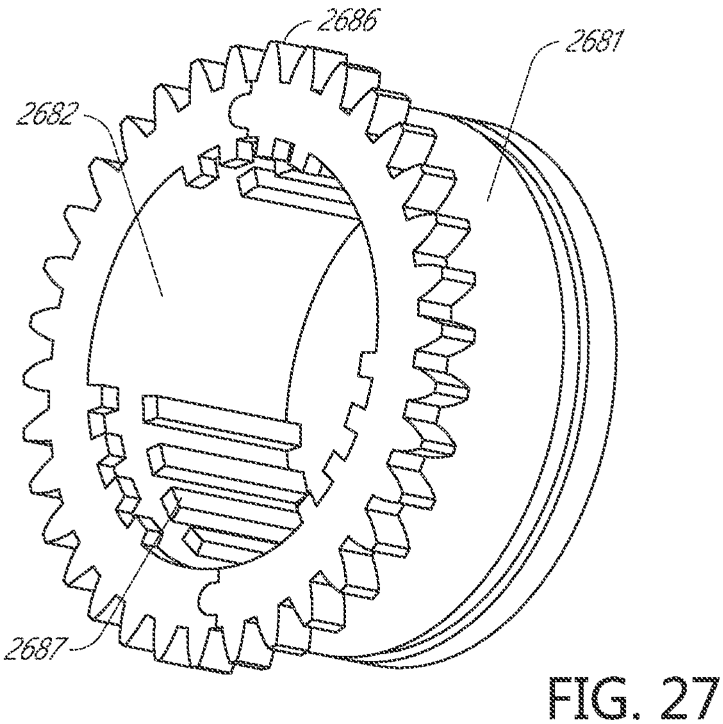
FIG. 27 illustrates a perspective view of a holder ring that can be used to hold and rotate a target device in accordance with one or more embodiments.

FIG. 27 illustrates an exemplary holder ring 2681 that can be used to hold and to rotate a target device (e.g., a heart valve). The holder ring 2681 can include a geared portion 2686 (e.g., with gear teeth) or other interlocking or friction-engaging portion, etc. that can interact with another gear 2683, interlocking component, friction-engaging component, etc. to cause rotation of the holder ring 2681. The other gear 2683, interlocking component, friction-engaging component, etc. can be connected to a drive shaft (not shown). The drive shaft can connect between a motor and the other gear 2683, interlocking component, friction-engaging component, etc. such that the motor can cause the gear, interlocking component, friction-engaging component, etc. to rotate. Rotation of the gear 2683, interlocking component, friction-engaging component, etc. can cause the holder ring 2681 to rotate.

The holder ring 2681 can include an inner surface 2682 configured to hold and engage the target device. Though, in one embodiment, the outer surface can be configured to hold and engage the target device with the target device fitting over and around the outer surface. Features 2687 can be included on the inner surface 2682 (or outer surface) to improve the hold or better secure the target device. The holder ring 2681 (and/or its inner surface 2682) can be configured to cover only a small surface area of the target device, e.g., to leave portion of the target device to be operated on, treated, sutured, etc. open and unobstructed. The interior of the target device can beneficially be left accessible and open from both ends to allow an operator access from either end to the interior of the target device. Using a rotating holder assembly 2680 allows an automated fixture to rotate a target device without having to rotate the entire holder assembly. This allows the automated fixture to keep the target device (e.g., a portion of the target device or surface thereof) within a depth of field of a visualization system (e.g., a camera) throughout 360-degree rotation of the target device without requiring movement of the visualization system or adjustment of the focus, and without ever having an arm or other portion of the holder assembly 2680 rotate into the visualization system's (e.g., camera's) view. Similarly, this allows the automated fixture to move the target device in such a way as to not require the vision assist system to re-adjust its position to achieve desired localization of a visual indicator on the target device.

While an exemplary implementation is shown in FIGS. 26 and 27, other implementations of the concepts described are also possible that may include additional elements or components, different elements or components, or not include some elements or components.

Figure 31:
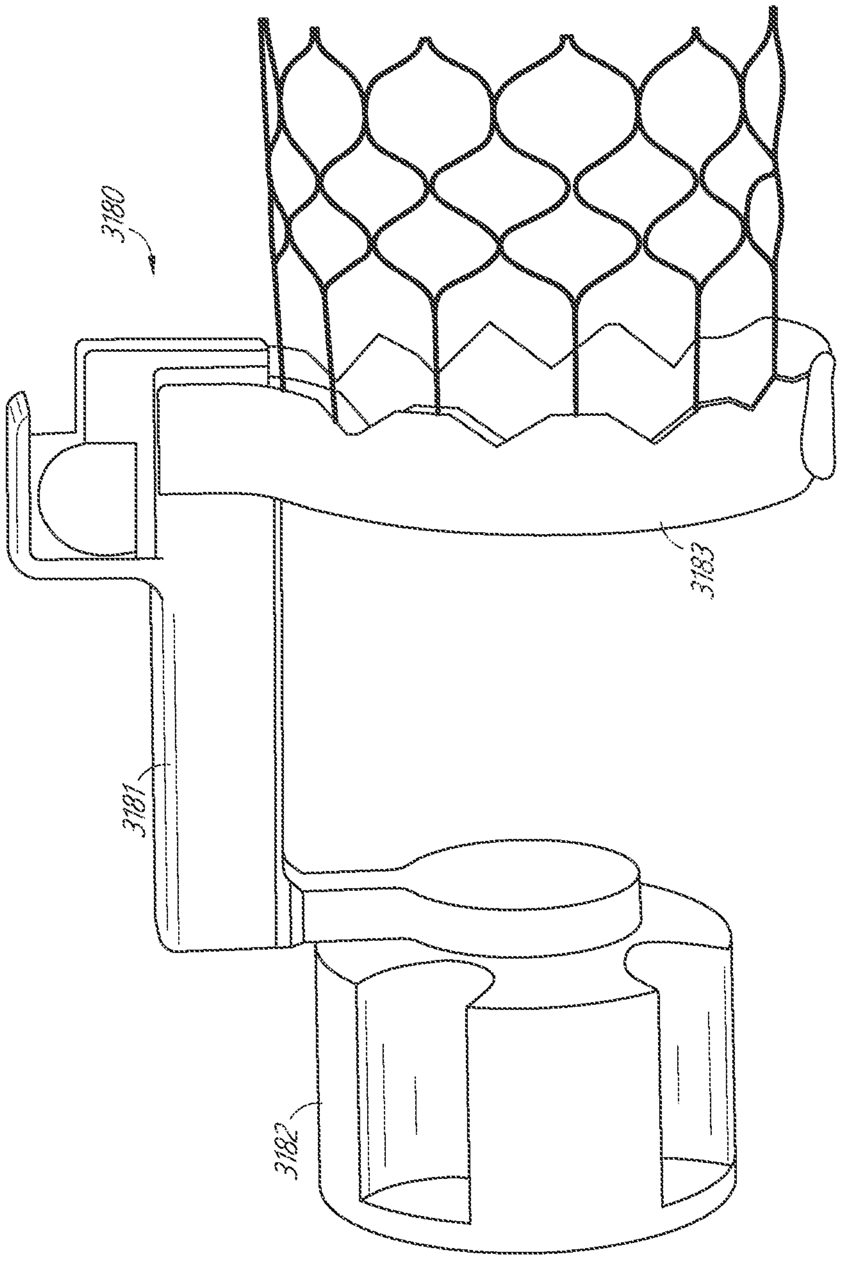
FIG. 31 illustrates an exemplary holder assembly that extends distally from an articulation arm to allow access to an internal portion of a target device from an in-flow or out-flow approach.

FIG. 31 illustrates another example holder or holder assembly 3180 that extends distally from an articulation arm to allow access to an internal portion of a target device (e.g., a valve) from both an in-flow end and an out-flow end of the target device. In other words, the holder assembly is configured such that it does not block or leaves open the ends. The holder assembly 3180 includes a support arm 3181 that extends from a base 3182 that couples to an articulation arm, examples of which are described herein. In some embodiments, the articulation arm and/or base 3182 are configured to rotate about a central or longitudinal axis of a support 3183 (e.g., a cylinder support) of the holder assembly 3180. The support 3183 is coupled to the support arm 3181 and is configured to secure the target device to the holder assembly 3180 in the same or similar manner as other holder assemblies described herein.

Suture and/or Inspection Assistance Using Vision Assist Systems

Embodiments disclosed herein provide for systems, devices, and methods for providing point-by-point assistance (e.g., point-by-point suture assisting) functionality in connection with procedures (e.g., the suturing of implant devices, inspection, or other procedures). For example, a suture assistance system in accordance with the present disclosure may provide point-by-point (e.g., step-by-step) assistance to an operator through the use of an automated suture fixture and a vision assist system which may also include a visualization system (e.g., a microscope and/or magnification system, and/or an image display system), and/or other associated systems, devices, or components.

Figure 14:
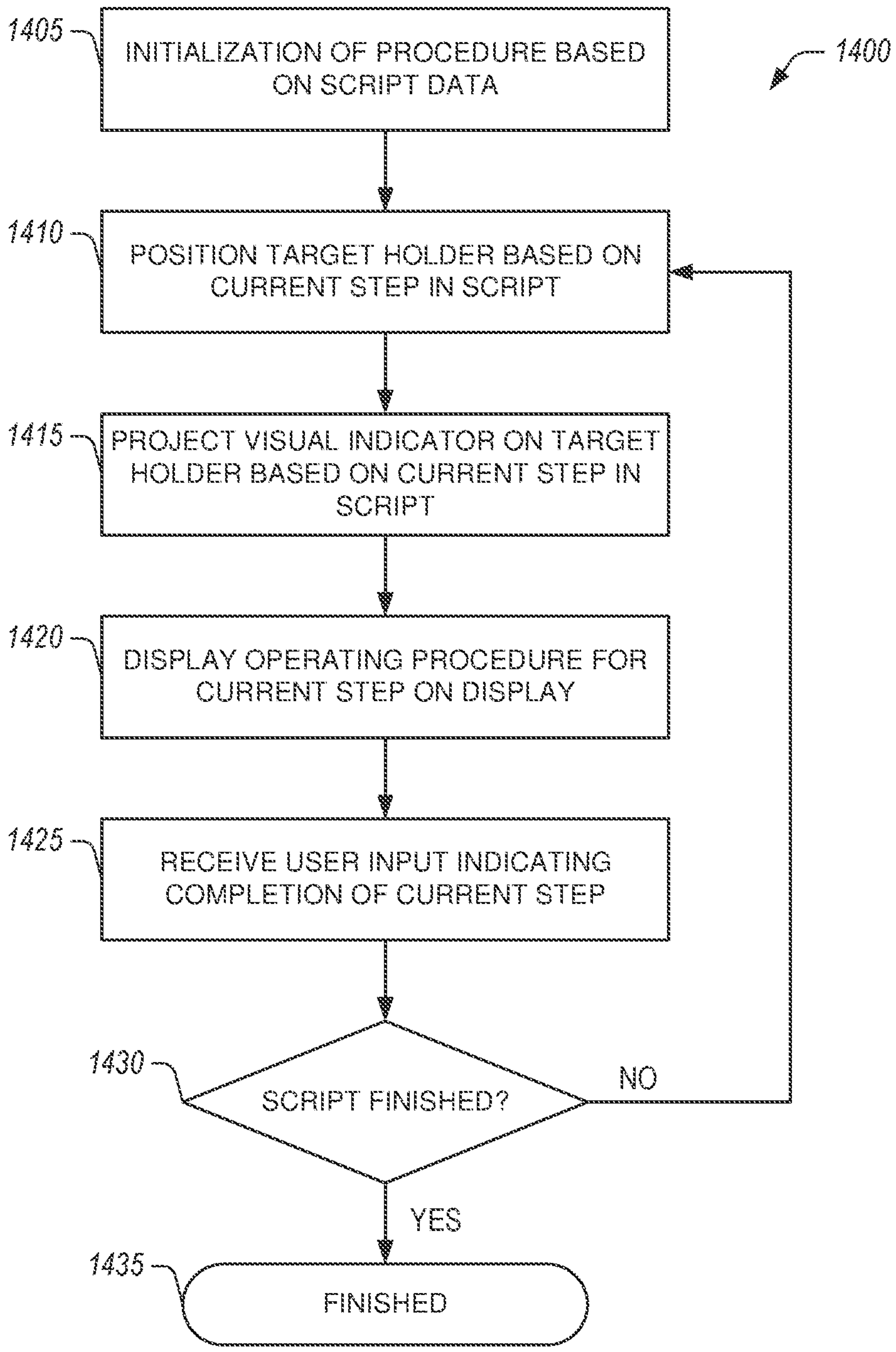
FIG. 14 illustrates a flow chart of an example method of performing a scripted procedure on a target device using an assistance system.

FIG. 14 illustrates a flow diagram of an example method 1400 of performing a scripted procedure on a target device using an assistance system. While described in terms of a suturing procedure, similar steps can be used for other procedures (e.g., for inspection procedures, other treatment or processing procedures, etc.). For example, the method 1400 can be performed after a suture assistance system has been preprogrammed with a certain procedure, program, or script. One or more computer components, such as one or more processors and/or memory devices, can be utilized to store and execute a procedure-directing script or program, such that a procedure script or program can be played back for an operator on-demand. In certain embodiments, moving from one step of the process 1400 to another can be triggered through user input (e.g., through the use of a foot pedal or operator-input triggered device, voice commands, and/or other electronic input).

At block 1405, the method includes loading a pre-programmed suturing process script or program. The script can be based on script data, as described herein with respect to FIG. 7A. The script can be loaded in various ways, e.g., by providing input to the system or a computer of the system to load the desired script from storage or memory (e.g., stored memory, internal memory, external memory, portable memory, disk, thumb drive, download, etc.), loading the script from an external source, inputting or providing a code (e.g., scanning a barcode on the target device or materials associated with the target device) such that the system automatically loads the correct script for the target device (e.g., based on the input code, scanned barcode, etc.), providing voice commands to load a script, and other ways of loading the script. In certain embodiments, the method 1400 involves selectively loading either a right-handed or left-handed version of the process script based on a preference of the operator or based on an operator profile, or applying operator information to a script to adjust the script to individual operator preferences (e.g., to flip the script positioning for left vs. right handed operators, to adjust positioning for other operator characteristics, for example, size, height, etc.). In certain embodiments, the operator may alternate between right- and left-handed versions as desired, even mid-procedure, which may beneficially allow the operator to rest a fatigued hand, for example. This could be done by applying different information or parameters to the script at different times.

At block 1410, the method includes positioning a target holder of an automated fixture to a current process position associated with a current step of the suturing procedure or other procedure. Initiation of the positioning of the target holder can be based on a triggering event in the script data or received from user input. For example, the operator can activate a foot pedal, other switch, physical trigger button, mechanism, voice command, and/or electronic input (e.g., a touchscreen icon/button, etc.) to initiate movement of the automated fixture.

At block 1415, the method includes identifying a target suture position or other position (e.g., inspection position, other treatment or processing position, etc.) and projecting a visual indicator on that target position. For example, the visual indicator can be projected using a light source so that a pattern or spot of light is visible on a surface of the target device at the location relevant to the current step in the procedure (e.g., based on information from the loaded script program). In some embodiments, identifying the target suture position and providing the visual indicator can be accomplished using the method 1600 described herein with reference to FIG. 16.

At block 1420, the method includes displaying an operating procedure for the current step on a display. The displayed operating procedure can include any suitable combination of images, video, text, and the like to indicate to the operator operations to be performed for the current step. In some embodiments, the display can include a live image of the target device and can indicate a target suture position or other target position relative to the live image. Indication of the target suture position may be achieved using instructions, or other visual overlays, examples, and/or guidance displayed on the display. The target position can be identified by the operator (e.g., by clicking on a target position, dragging a visual aid to the target position, entering coordinates, or in other ways), and/or the target position can be identified by the script or program automatically to sense and/or indicate where the next step, operation, suture, inspection, etc. should occur.

At block 1425, the method includes receiving user input indicating completion of the current step. As described herein, user input can be received through any suitable means including a foot pedal, touchscreen, voice commands, and the like. Completion of the current step can include performance of a suturing or inspection operation.

In addition or as an alternative, at block 1425 the method includes determining completion of the current step. This may occur without receiving user input indicating completion of the current step or it may occur prior to receiving user input indicating completion of the current step. Upon completion of the step, as determined by the assistance system or based on user input, the assistance system can signal completion by providing an audible and/or visual cue. For example, a beep or other audio clue can be provided upon completion of the step. As another example, the assistance system can change the color (or other property such as persistence) of the visual indicator to signal completion. The visual indicator can be made to change color from red to green to signal that the assistance system has determined that the step has been completed. Similarly, the visual indicator can be made to blink with a particular cadence to signal completion of the step. This can be used to signal to the operator that it is appropriate to move to the next step of the procedure.

Once the suturing step or other step has been indicated as being complete at block 1425, the assistance system determines if the script is complete. If the completed suturing operation or other operation represents a final operation of the procedure, the process 1400 ends as shown at block 1435. If additional steps of the procedure remain, the process 1400 returns to block 1410, where a subsequent step of the procedure is triggered, such that the process 1400 completes one or more subsequent steps.

In certain embodiments, the process 1400 may involve verifying that the step has been performed correctly prior to advancing to the next step in the script. The method 1700 represents an example of such a method and is described herein with respect to FIG. 17. In some embodiments, the process 1400 may include capturing an image of the suture target prior to the repositioning of the automated fixture. For example, image capture can be triggered by user input or other event indicating the completion of a step of the process 1400. Such captured images can be used for a variety of purposes including training and inspection. Optionally, the entire procedure can be recorded (e.g., as a video) for training, inspection, quality control, and/or other purposes. Bookmarks or indicators can be stored at times when a step is completed to allow an operator, supervisor, or other person to jump through the video to key times or frames, e.g., for inspection, training, or other purposes. Additionally, the images, video, frames, etc. can be sent or transmitted and graphically displayed on another device (e.g., phone, computer, mobile device, etc.). For example, images or video can be sent to a device of a manager and/or quality control person for review.

Where the suture assistance system has been programmed to implement, or direct the implementation of, a suturing procedure or other procedure, such procedure may be repeatable over many iterations, thereby providing improved efficiency and completion of procedures (e.g., improved suturing of implant devices).

In certain embodiments, the process 1400 can allow for the operator to make modifications at a given step of the suturing procedure. This can be done to allow the operator to modify the positioning of the automated suture fixture and/or vision assist system in order to customize the current step. In certain embodiments, such altering by the operator can be programmed back into the procedural script executed by the suture assistance system in connection with the particular procedure, such that future execution of the procedure can incorporate the modifications implemented by the operator during the process 1400. Furthermore, in certain embodiments, the process 1400 can allow for the operator to temporarily pause the process 1400 prior to completion thereof. For example, the operator may wish to step away from the operating environment, such as for a break or other purpose, wherein the process 1400 can allow for the operator to reinsert themselves into a stage of the process at which the process was paused. Therefore, such availability of pausing and reentering the process may allow for the operator to reduce strain or burden associated with prolonged engagement with the suture assistance system.

In various embodiments, the assistance system implementing the process 1400 can include the ability to track the time or duration of individual steps in the procedure. The assistance system can be configured to track the duration of individual steps in individual procedures for individual operators. This enables a comparison to be made between operators to identify an operator that is taking longer than average to complete a step. This may be used to signal a supervisor that the operator may need assistance in completing the step. Time tracking may also be used to generate operator analytics to assist in assessing operator performance and/or to identify when an operator is at pace, ahead of pace, or behind pace. The timing information can be used for manufacturing line management, coaching, training, etc.

Certain suturing procedures (or other procedures) may involve suturing (or other processing, treatment, etc.) of implant devices that have certain requirements with respect to moisture and/or other parameters associated with one or more components of the implant device. For example, with respect to prosthetic heart valves, suturing operations or other operations associated with valve leaflets may require that such leaflets not become dried out, because drying out can adversely affect the physical properties thereof. For example, where the valve leaflets comprise biological material, such as pericardial leaflets, it may be necessary or desirable to periodically expose such leaflets to moisture, such as in the form of a liquid solution, gas, or the like. In certain embodiments, the process 1400, and/or other processes or procedures disclosed herein, can be implemented in connection with a mechanism for allowing the operator or system (e.g., an automated portion of the system) to periodically, or on an as-needed basis, moisturize one or more components of the implant device being sutured. For example, the system can allow the operator to immerse or otherwise saturate or cover at least a portion of the implant device in, for example, glutaraldehyde, or other or liquid. In certain embodiments, an articulation arm in a suture assistance system can be configured to implement, as part of an automated procedure, the dipping or immersion, spraying, or other means of exposure, of an implant device or portion thereof in a moisturizing solution. For example, such immersion or other type of moistening of the implant device can be performed substantially automatically and may or may not require engagement by the operator. In certain embodiments, a timer can be implemented in connection with a suturing procedure in accordance with the present disclosure, wherein the timer indicates and/or notifies an operator of moisturizing requirements for an implant device being operated on. For example, with respect to the process 1400 of FIG. 14, an interrupt routine may be implemented which is designed to interrupt the operator and/or the process executed by the suture assistance system when it is determined that it is necessary or desirable for the operator to moisturize the implant device or portion thereof. In some implementations, the assistance system can track the time since the last moisturizing event. If the time reaches a threshold, the assistance system can initiate a moisturizing event (e.g., dipping the target device into liquid). In certain implementations, the assistance system can calculate the expected duration of the next step in the procedure and if that duration causes the target device to be outside of the time limit for submersion or moisturizing, the assistance system can initiate a moisturizing event prior to beginning (or allowing the operator to begin) the next step in the procedure. The assistance system can incorporate a safety buffer to make sure the maximum exposure time to air is not exceeded. In certain embodiments, sensors, light, lasers, and/or other techniques can be used to detect the moisture level or other characteristics of the target or implant device or leaflets. In certain embodiments, the process 1400 may not continue until the operator has performed the moisturizing step, or alternatively the articulation positioning device that holds the implant device may execute the moisturizing operation in response to the interrupt routine.

Figure 16:
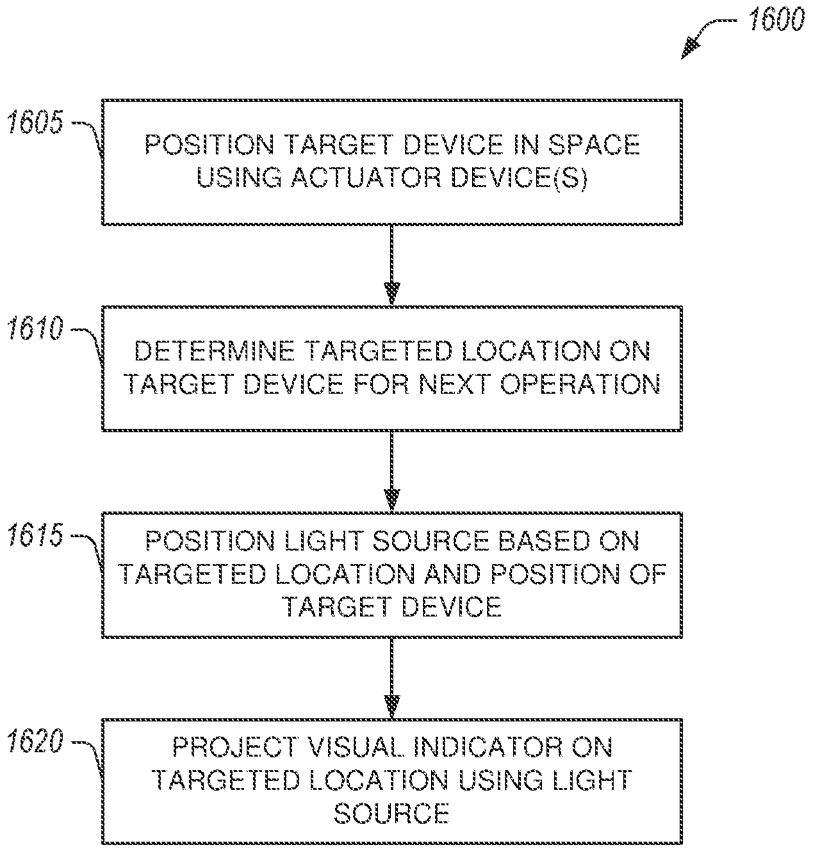
FIG. 16 illustrates a flow diagram of an example method of producing a visual indicator on a target device.

FIG. 16 illustrates a flow diagram of an example method 1600 of producing a visual indicator on a target device. The method 1600 can be used as a subroutine of the method 1400 to produce the visual indicator during a suturing or inspection process.

At block 1605, the method includes positioning the target device in space using actuators and a target holder of an automated fixture. The position and orientation of the target device is determined based on script data. Actuators of the automated fixture move and rotate to position the target device in a suitable position to allow the operator to perform the next step in the procedure.

At block 1610, the method includes determining a targeted location on the target device for the current step in the procedure. The targeted location can include the location of the suture to be stitched on the target device, the location of a stitch to be inspected, or other such location. The location on the target device can be retrieved from the script data.

At block 1615, the method includes positioning a light source of the vision assist system based at least in part on the targeted location and the position of the target device. The vision assist system can be configured to determine the targeted location on the target device based at least in part on the positioning of the target device by the automated fixture and the location on the target device that is the targeted location. Combining this data, the vision assist data can determine the point in space that represents the targeted location. Furthermore, the vision assist system can determine a position and orientation of the light source than enables the light source to produce a visual indicator on the target device at the targeted location. This can include analyzing a three-dimensional model of the target device stored in a data store, as described herein with respect to FIG. 7A. In some embodiments, the positioning of the light source can be manually adjusted and stored as part of the procedure script so that during subsequent similar procedures, the light source will be automatically positioned as determined or adjusted by the operator.

At block 1620, the method includes projecting a visual indicator in the targeted location using the light source of the vision assist system. The light source of the vision assist system can generate a color of light that is solid or flashing, that is rapidly scanned to form a pattern, or that forms an image, shape, or animation at the targeted location, wherein the light on the targeted device forms the visual indicator. The visual indicator can have any of the properties described herein and can change based on feedback received from a visualization system and/or an operator.

Figure 17:
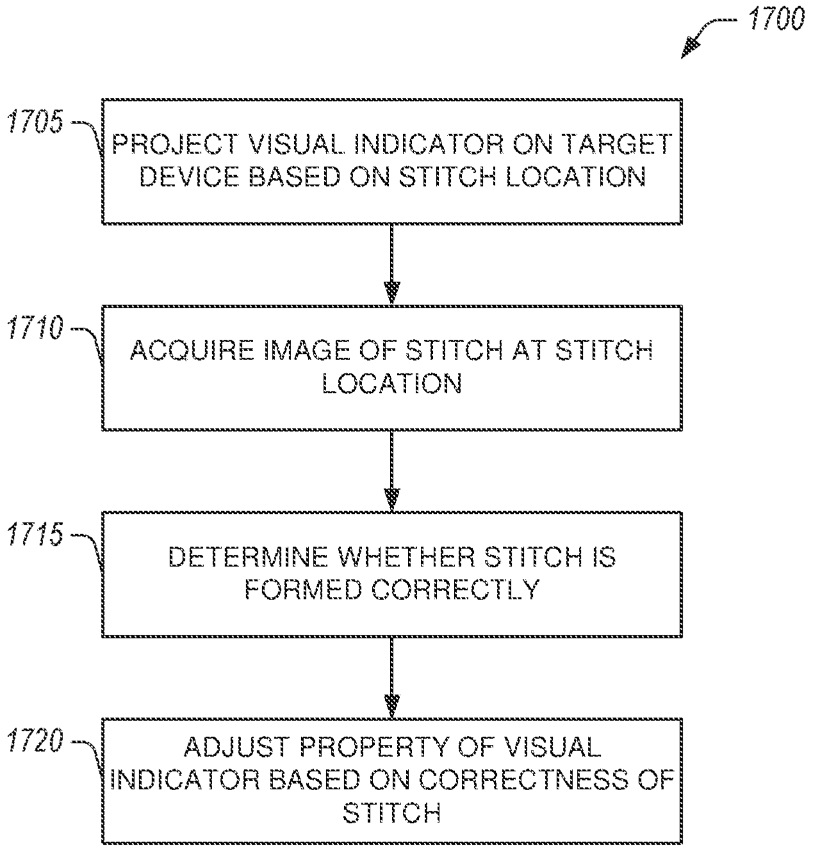
FIG. 17 illustrates a flow diagram of an example method of using a visual indicator in conjunction with inspecting a stitch on a target device.
Figure 18:
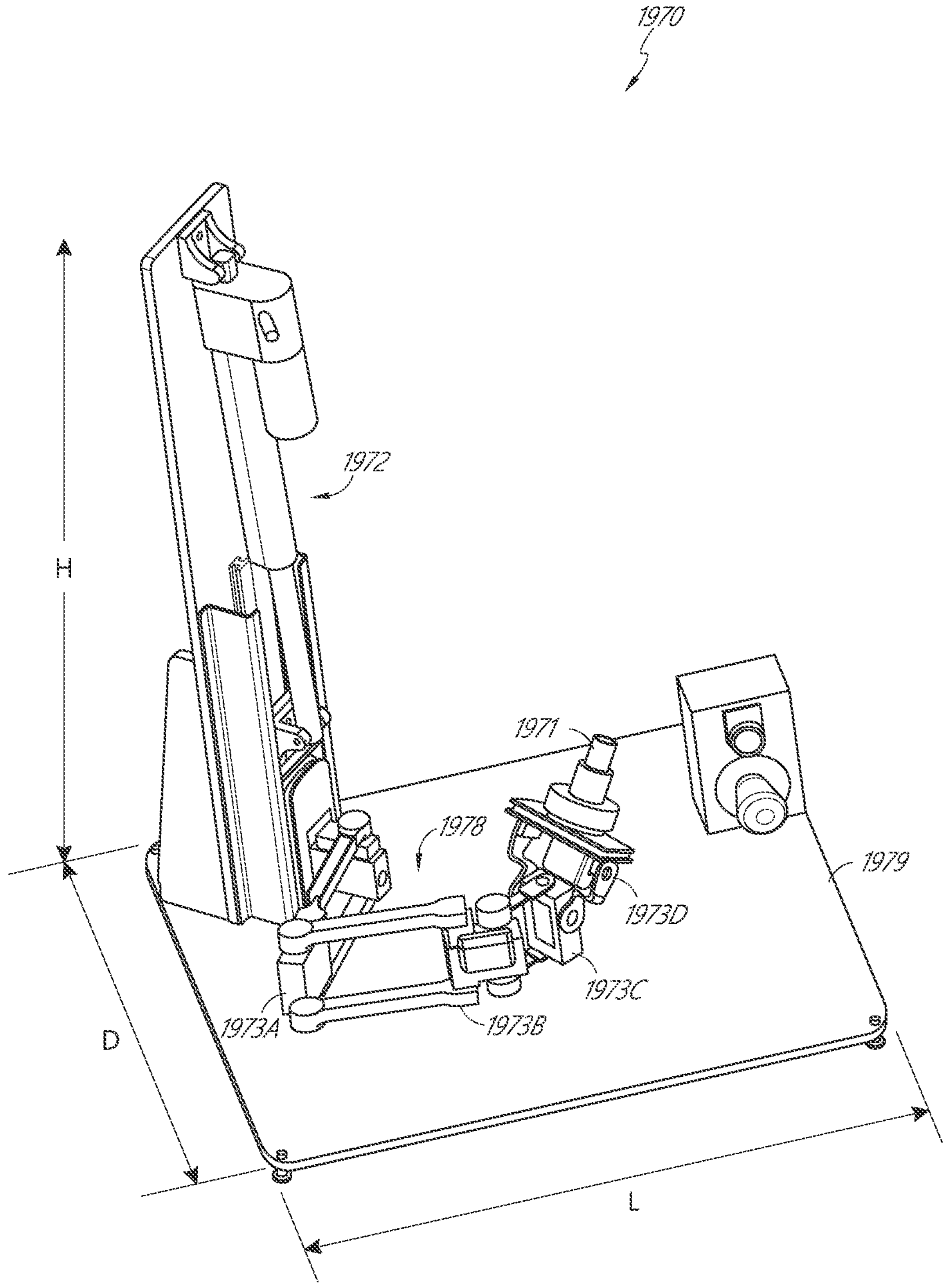
Figure 25:
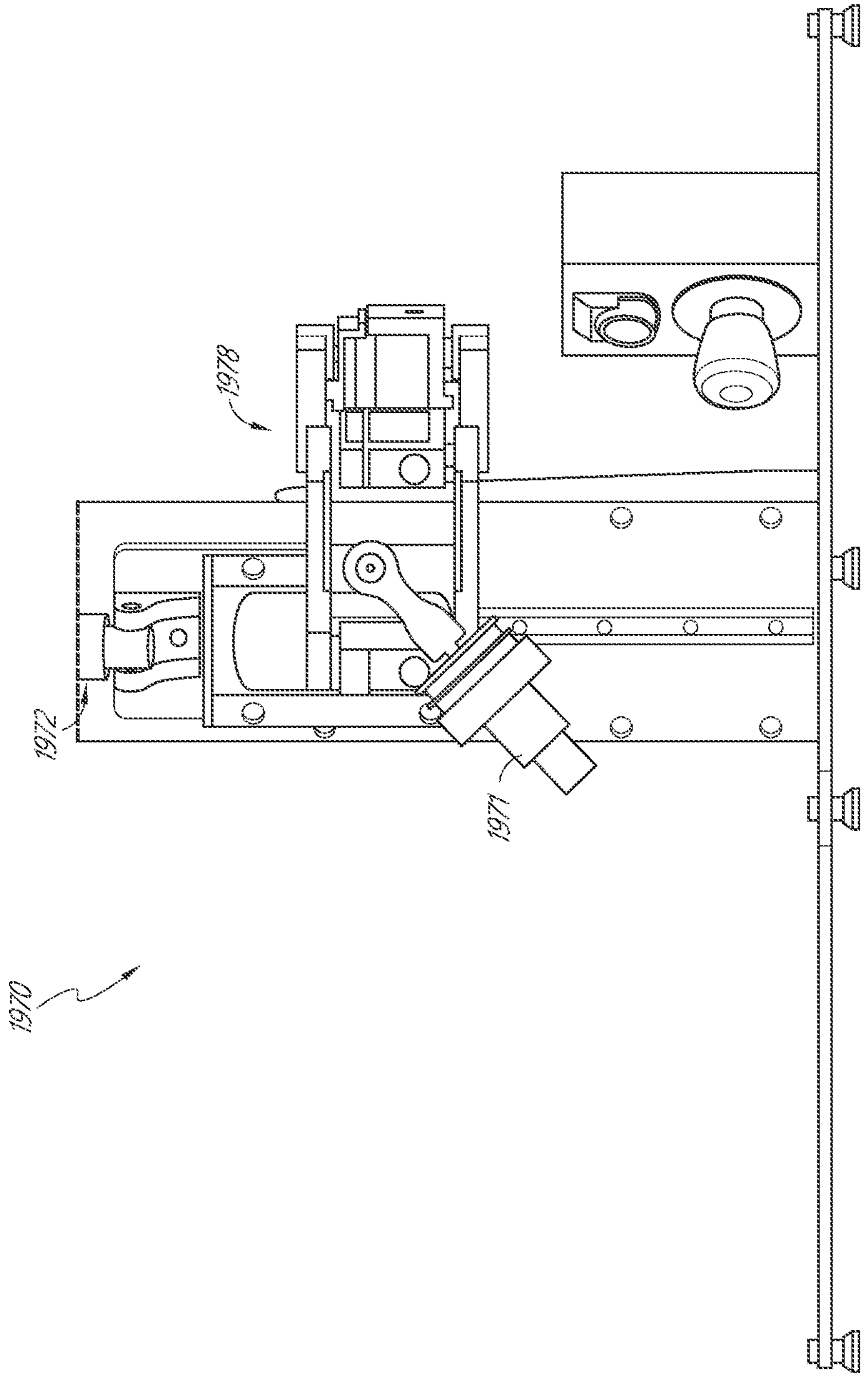

FIG. 17 illustrates a flow diagram of an example method 1700 of using a visual indicator in conjunction with inspecting a stitch on a target device. The method 1700 can be used as a subroutine of the method 1400 to verify satisfactory performance of a step in a procedure prior to proceeding to a next step in the procedure.

At block 1705, the method includes projecting a visual indicator on the target device based at least in part on a stitch location. This can be similar to what is described herein, particularly with respect to the method 1600.

At block 1710, the method includes acquiring an image of the stitch at the stitch location. The image can be acquired with a visualization system that includes one or more imagers (e.g., cameras).

At block 1715, the method includes determining whether the stitch is performed correctly. Determination of the correctness of the stitch can involve comparing the acquired image(s) to a library of images of correct and/or incorrect stitches. Machine vision algorithms can be utilized to compare the acquired images to the images in the image library to determine deviation from correct stitches, compliance with correct stitches, similarities to incorrect stitches, or the like. Based on these comparisons, the method can return a result indicating whether the stitch is correctly formed.

At block 1720, the method includes adjusting a property of the visual indicator based at least in part on the determination of the correctness of the stitch. In some embodiments, the visual indicator can have a first set of properties while analyzing the stitch and can switch to a second set of properties if the stitch is determined to be incorrect or to a third set of properties if the stitch is determined to be correct. Properties of the visual indicator projected onto the target device can include any of the properties described herein. The properties can include, for example and without limitation, any one or more of the following: color, shape, pattern, brightness, intensity, persistence (e.g., solid or flashing), or the like.

Figure 32:
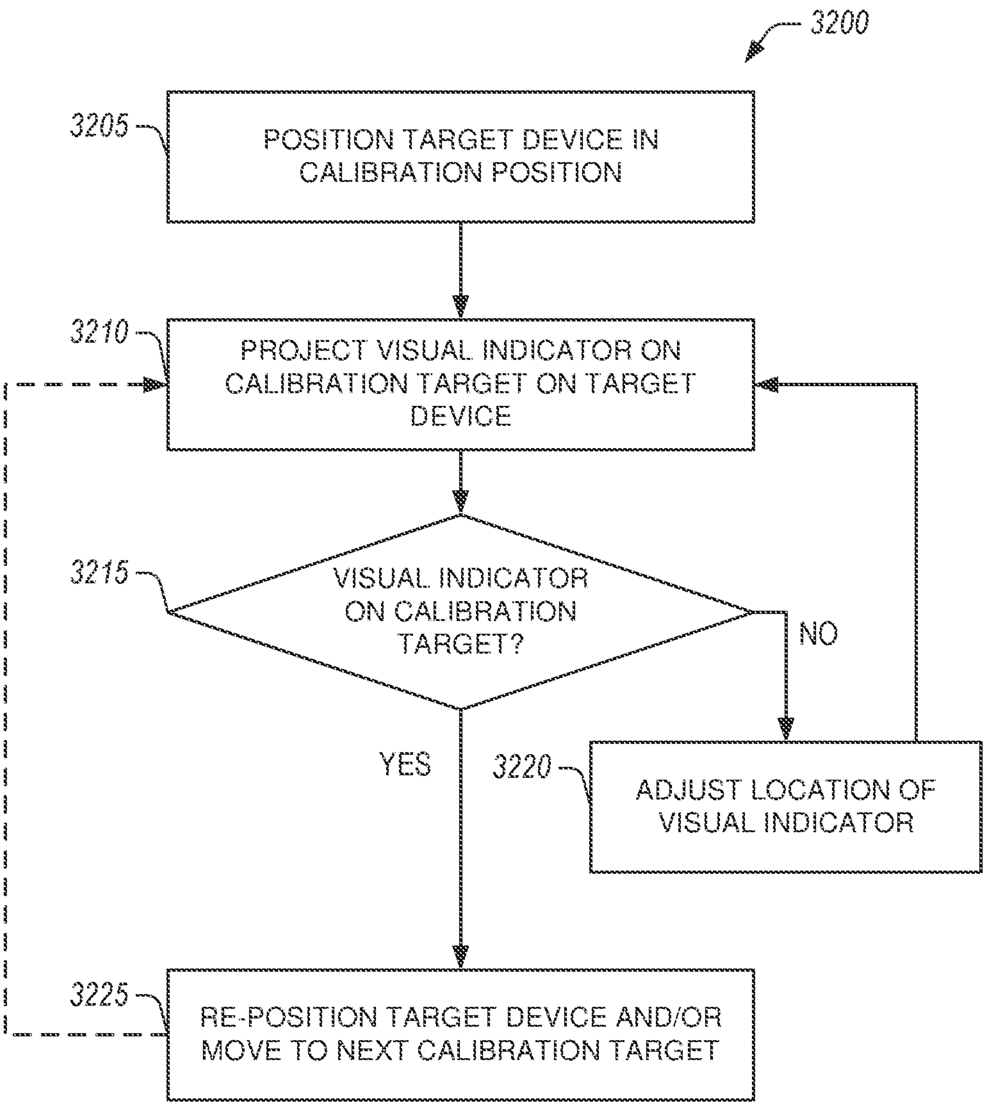
FIG. 32 illustrates a flow chart of an example calibration procedure for a vision assist system of a suturing system.

FIG. 32 illustrates a flow diagram of an example method 3200 of calibrating a vision assist system, examples of which are disclosed herein. One or more computer components, such as one or more processors and/or memory devices, can be utilized to store and execute a calibration script or program and to store calibration data acquired during the procedure. In certain embodiments, moving from one step of the process 3200 to another can be triggered through the use of a foot pedal, other operator-input triggered device, voice commands, and/or other electronic input.

At block 3205, the calibration procedure includes positioning a target device in a first or initial calibration position. The target device can be a valve or other component, as described herein. The target device may also be a specially-configured calibration device designed for the calibration procedure. The target device can include one or more markings indicating one or more corresponding calibration targets. The calibration targets can be circles or other shapes or indicators. The calibration procedure can include calibration script, the calibration script including a sequence of calibration targets. The calibration script can also include corresponding positions and/or orientations of the target device.

At block 3210, the calibration procedure includes projecting a visual indicator on a calibration target of the target device. The visual indicator can be projected using any suitable component or device described herein. In some embodiments, the visual indicator is projected from a laser pointer or other similar device. The calibration script can also include corresponding positions and/or orientations of a vision assist system to project the visual indicator on or within a calibration target.

At block 3215, the calibration procedure includes verifying that the visual indicator is projected onto (or within) the calibration target. Verifying that the visual indicator is on or within the calibration target can be accomplished by an operator using a user input device or it can be accomplished by a visualization system that includes image recognition capabilities, as described herein. In some embodiments, the calibration target is a circle or other shape and the visual indicator is considered calibrated when it is within the circle or otherwise contacting the calibration target.

If the visual indicator is not on the calibration target, at block 3220 the calibration procedure includes adjusting a location of the visual indicator. This can be done using articulating arms, optics, or the like to adjust the projection of the visual indicator. This may also include adjusting the position and/or orientation of the target device. The adjustments made to the visual indicator and/or the target device can be based on operator feedback and/or image analysis feedback. The feedback can be provided in real time so that the visual indicator can be iteratively adjusted so that it approaches the calibration target. This is represented by the arrow returning to block 3210, where the visual indicator is again projected to attempt to contact or fall within the calibration target.

Adjustments made to the visual indicator and/or the target device can be stored as calibration data. The calibration data can be used to adjust properties of stored procedure scripts, examples of which are described herein. The calibration data can be tracked over time to track performance of the associated suturing system and components.

If the visual indicator is on the calibration target, at block 3225 the calibration procedure moves onto the next calibration step. This may be accomplished by re-positioning the target device, in some implementations. This may also be accomplished by adjusting a position of one or more components of the suturing system (e.g., the vision assist system) to target the next calibration target. This procedure can be repeated for any suitable number of calibration targets (e.g., 1, 2, 3, 4, 5, 6, etc.).

In some embodiments, the calibration data acquired during the calibration procedure 3200 can be stored and updated for individual types of target devices, individual operator setups or configurations, individual script procedures, and the like.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

While many of the specific examples and embodiments described herein focus on suturing assist systems, automated suture fixtures, suturing operations/steps/procedures, etc. the invention is not limited to suturing applications and the same or similar systems, fixtures, devices, features, components, principles, operations/steps/procedures, etc. to those discussed with respect to suturing can be used for other operations/steps/procedures/treatments, etc. For example, the system may be used to apply material to a frame using sputtering, electrospinning, rivets, staples, fasteners, fastener guns, clamps, or in other ways without involving suturing. While much of the discussion focuses on implant devices (e.g., human prosthetic heart valve implants) or other specific examples, the same or similar systems, fixtures, devices, features, components, principles, operations/steps/procedures, etc. to those discussed with respect to the examples above can be applied to other types of target devices.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments do include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Components, aspects, features, etc. of the systems, assemblies, devices, apparatuses, methods, etc. described herein may be implemented in hardware, software, or a combination of both. Where components, aspects, features, etc. of the systems, assemblies, devices, apparatuses, methods, etc. described herein are implemented in software, the software may be stored in an executable format on one or more non-transitory machine-readable mediums. Further, the software and related steps of the methods described above may be implemented in software as a set of data and instructions. A machine-readable medium includes any mechanism that provides (e.g., stores and/or transports) information in a form readable by a machine (e.g., a computer). For example, a machine-readable medium includes read only memory (ROM); random access memory (RAM); magnetic disk storage media; optical storage media; flash memory devices; DVD's, electrical, optical, acoustical or other forms of propagated signals (e.g., carrier waves, infrared signals, digital signals, EPROMs, EEPROMs, FLASH, magnetic or optical cards, or any type of media suitable for storing electronic instructions. Information representing the units, systems, and/or methods stored on the machine-readable medium may be used in the process of creating the units, systems, and/or methods described herein. Hardware used to implement the invention may include integrated circuits, microprocessors, FPGAs, digital signal controllers, stream processors, and/or other components.

What is claimed is:

1. A suturing assistance system comprising:

an automated fixture comprising a plurality of actuator devices coupled to a target holder, the automated fixture being configured to maneuver a target device mounted to the target holder; and a vision assist system comprising a source of light and an optical fiber with a light-emitting end and a light-receiving end optically coupled to the source of light, the vision assist system configured to use the light-emitting end of the optical fiber to project a visual indicator on a targeted location of the target device, wherein the light-emitting end of the optical fiber is positioned within the target device and the visual indicator is generated by backlighting the target device with light generated by the source of light and emerging from the light-emitting end of the optical fiber, wherein the source of light and the light-receiving end of the optical fiber remain fixed relative to the vision assist system and the target holder, wherein the plurality of actuator devices of the automated fixture is configured to move and to orient the light-emitting end of the optical fiber to change a location of the visual indicator.

2. The system of claim 1, wherein the target device is a heart valve.

3. The system of claim 1 further comprising a controller configured to direct the automated fixture and the vision assist system to perform a pre-programmed suturing procedure.

4. The system of claim 1, wherein the vision assist system further includes one or more optical elements configured to change a location or characteristic of the visual indicator.

5. The system of claim 1, wherein the vision assist system further includes a second optical fiber configured to generate two or more simultaneous visual indicators on the target device.

6. A suturing system comprising:

an automated suture fixture comprising a plurality of actuator devices and a suture target holder, the automated suture fixture being configured to position a target device mounted to the suture target holder;

a vision assist system comprising a source of light and an optical fiber with a light-emitting end and a light-receiving end optically coupled to the source of light, the vision assist system configured to use the light-emitting end of the optical fiber to project a visual indicator on a targeted location of the target device;

a data store storing suturing procedure script data, the suturing procedure script data including a first data set representing a plurality of positions of the automated suture fixture and the suture target holder for a suturing procedure, the data store further storing target device data including a second data set representing the target device shape in three-dimensional space; and a controller configured to access the suturing procedure script data and the target device data, to provide position control signals to the automated suture fixture and to the vision assist system based at least in part on the suturing procedure script data and the target device data, wherein the light-emitting end of the optical fiber is positioned within the target device and the visual indicator is generated by backlighting the target device with light generated by the source of light and emerging from the light-emitting end of the optical fiber, wherein the source of light and the light-receiving end of the optical fiber remain fixed relative to the vision assist system and the target holder, wherein the plurality of actuator devices of the automated fixture is configured to move and to orient the light-emitting end of the optical fiber to change a location of the visual indicator.

7. The suturing system of claim 6, wherein the target device is a prosthetic human heart valve implant device.

8. The suturing system of claim 6, wherein the controller is further configured to select the first data set from among a plurality of data sets of the suturing procedure script data.

9. The suturing system of claim 6, wherein the controller is configured to generate a three-dimensional topological map of the target device based on the target device data.

10. The suturing system of claim 6, wherein, in the transition between two or more steps of the suturing procedure, the light-emitting end of the optical fiber is configured to remain stationary and the automated fixture is configured to adjust a position or orientation of the target device.

11. The suturing system of claim 6, wherein, in the transition between two or more steps of the suturing procedure, the light source source of light is configured to change a characteristic of the visual indicator to indicate information regarding differences between the two or more steps of the suturing procedure.

12. The system of claim 1, wherein the optical fiber passes through a lumen formed by the target holder.

13. The system of claim 1, wherein a light-emitting end of the optical fiber is surrounded by the target device attached to the target holder.

14. The system of claim 1, wherein the optical fiber is held by one or more components of the target holder.

15. The suturing system of claim 6, wherein the optical fiber passes through a lumen formed by the suture target holder.

16. The suturing system of claim 6, wherein a light-emitting end of the optical fiber is surrounded by the target device attached to the suture target holder.

17. The suturing system of claim 6, wherein the optical fiber is held by one or more components of the suture target holder.

18. The system of claim 1, wherein the source of light comprises an LED optically coupled to the light-receiving end of the optical fiber.

19. The suturing system of claim 6, wherein the source of light comprises an LED optically coupled to the light-receiving end of the optical fiber.

* * * * *